US011325930B2

(12) United States Patent
Canales et al.

(10) Patent No.: US 11,325,930 B2
(45) Date of Patent: May 10, 2022

(54) COT MODULATORS AND METHODS OF USE THEREOF

(71) Applicant: Gilead Sciences, Inc., Foster City, CA (US)

(72) Inventors: Eda Y. Canales, San Mateo, CA (US); Manoj C. Desai, Foster City, CA (US); Eric Gorman, Hayward, CA (US); Jiayao Li, Foster City, CA (US); Roland D. Saito, San Mateo, CA (US); James G. Taylor, Burlingame, CA (US); Nathan E. Wright, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/162,754

(22) Filed: Jan. 29, 2021

(65) Prior Publication Data
US 2021/0147454 A1 May 20, 2021

Related U.S. Application Data

(60) Division of application No. 16/994,889, filed on Aug. 17, 2020, now Pat. No. 10,947,259, which is a continuation of application No. 16/898,981, filed on Jun. 11, 2020.

(60) Provisional application No. 62/861,390, filed on Jun. 14, 2019.

(51) Int. Cl.
*C07D 401/14* (2006.01)
*C07F 9/6558* (2006.01)

(52) U.S. Cl.
CPC ........ *C07F 9/65583* (2013.01); *C07D 401/14* (2013.01)

(58) Field of Classification Search
CPC .................................................. C07D 401/14
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 7,297,795 B2 | 11/2007 | Sutherland et al. |
| 7,432,279 B2 | 10/2008 | Green et al. |
| 7,741,354 B2 | 6/2010 | Thormann et al. |
| 8,008,481 B2 | 8/2011 | Ericsson et al. |
| 9,815,818 B2 | 11/2017 | Bacon et al. |
| 9,878,995 B2 | 1/2018 | Bacon et al. |
| 9,878,996 B2 | 1/2018 | Silverman |
| 10,059,695 B2 | 8/2018 | Balan et al. |
| 10,316,017 B2 | 6/2019 | Bacon et al. |
| 10,577,352 B2 | 3/2020 | Balan et al. |
| 10,947,259 B2 | 3/2021 | Canales et al. |
| 10,974,259 B2 * | 4/2021 | Rong .................... B05B 1/1636 |
| 11,066,414 B2 | 7/2021 | Bacon et al. |
| 2005/0043537 A1 | 2/2005 | Sutherland et al. |
| 2006/0264460 A1 | 11/2006 | Green et al. |
| 2013/0116206 A1 | 5/2013 | Pisaneschi et al. |
| 2013/0225579 A1 | 8/2013 | Zhang et al. |
| 2015/0297573 A1 | 10/2015 | Dalle et al. |
| 2017/0008873 A1 | 1/2017 | Bacon et al. |
| 2017/0152240 A1 | 6/2017 | Bacon et al. |
| 2017/0268069 A1 | 9/2017 | Garraway et al. |
| 2017/0362201 A1 | 12/2017 | Bacon et al. |
| 2018/0002316 A1 | 1/2018 | Balan et al. |
| 2018/0237455 A1 | 8/2018 | Bacon et al. |
| 2019/0016705 A1 | 1/2019 | Balan et al. |
| 2020/0123172 A1 | 4/2020 | Bacon et al. |
| 2020/0392170 A1 | 12/2020 | Canales et al. |
| 2021/0061831 A1 * | 3/2021 | Canales ............... C07D 401/14 |

FOREIGN PATENT DOCUMENTS

| | | | |
|---|---|---|---|
| WO | WO 1998/043960 | 10/1998 | |
| WO | WO 2000/018740 | 4/2000 | |
| WO | WO 2005/019201 | 3/2005 | |
| WO | WO 2005/028443 | 3/2005 | |
| WO | WO-2005019201 A2 * | 3/2005 | ........... C07D 495/04 |
| WO | WO 2005/082891 | 9/2005 | |
| WO | WO 2006/124692 | 11/2006 | |
| WO | WO 2008/055950 | 5/2008 | |
| WO | WO 2017/007689 | 1/2017 | |
| WO | WO 2017/007694 | 1/2017 | |
| WO | WO 2018/005435 | 1/2018 | |
| WO | WO 2020/252151 | 12/2020 | |

OTHER PUBLICATIONS

Akriviadis et al., "Treatment of alcoholic hepatitis: is this a "dead-end"?" Ann Gastroenterol., 2016, 29(2): 236-237.
Chemical Abstract Registry No. 1092351-39-7, dated Dec. 31, 2008, retrieved on Mar. 25, 2020.
Chemical Abstract Registry No. 1349435-18-2, indexed in the Registry File on STN CAS Online Dec. 6, 2011.
Chemical Abstract Registry No. 1415564-65-6, dated Dec. 27, 2012, retrieved on Mar. 25, 2020.
Cohen et al., "Targeting protein kinases for the development of anti-inflammatory drugs", Curr Opin Cell Biol., 2009, 21:317-24.
Costa Rican Office Action in Patent Application No. 2017-0599, dated Apr. 13, 2021, 22 pages (with English translation).
Cusack et al., "Identification of a selective thieno[2,3-c]pyridine inhibitor of COT kinase and TNF-α production" Bioorganic & Medicinal Chemistiy Letters, 2009, 19:1722-25.
Detz et al., "Enantioselective Copper-Catalyzed Propargylic Amination" Angew. Chem. Int. Ed., 2008, 47:3777-3780.
Eisenberg et al., "Why can't we find a new treatment for SLE?", J Autoimmun, 2009, 32:223-30.

(Continued)

*Primary Examiner* — John S Kenyon
(74) *Attorney, Agent, or Firm* — Fish & Richardson P.C.

(57) ABSTRACT

The present disclosure relates generally to modulators of Cot (cancer Osaka thyroid) and methods of use and manufacture thereof.

4 Claims, 2 Drawing Sheets

(56) References Cited

OTHER PUBLICATIONS

Exam Report dated Dec. 21, 2018 for New Zealand Appl. No. 738525, 1 page.
Exam Report dated Jul. 25, 2019 for Indian Appl. No. 201817004204, 6 pages (with English translation).
Exam Report dated Oct. 24, 2019 for Australian Appl. No. 2019203122, 6 pages.
Exam Report in Pakastani Appln. No. 401/2016, dated Nov. 30, 2019, 2 pages.
Foster, "Deuterium Isotope Effects in Studies of Drug Metabolism," Trends Pharmacol. Sci., 1984, 5(12):524-527.
Gantke et al., "Regulation and function of TPL-2, an lkB kinase-regulated MAP kinase kinase kinase", Cell Res., 2010, 21 (1):131-45.
Garofalo et al., "Discovery of 4-alkylamino-7-aryl-3-cyanoquinoline LRRK2 kinase inhibitors", Bioorganic & Medicinal Chemistry Letters, 2013, 23:1974-1977.
Gavrin et al., "Inhibition of Tpl2 kinase and TNF-oc production with 1,7-naphthyridine-3-carbonitriles: Synthesis and structure-activity relationships" Bioorganic & Medicinal Chemistry Letters, 2005, 15:5288-5292.
GenBank Accession No. NP_004985, "matrix metalloproteinase-9 preproprotein [*Homo sapiens*]," Jul. 4, 2020, 3 pages.
George et al., "Discovery of thieno[2,3-c]pyridines as potent COT inhibitors" Bioorganic & Medicinal Chemistiy Letters, 2008, 18:4952-4955.
George et al., "Cot/Tpl-2 Protein Kinase as a Target for the Treatment of Inflammatory Disease", Current Topics in Medicinal Chemistiy, 2009, 9:611-622.
Gianatassio et al., "Strain Release Amination", Science, 2016, 351(6270):241-246.
Glatthar et al., "Discovery of Imidazoquinolines as a Novel Class of Potent, Selective, and in Vivo Efficacious Cancer Osaka Thyroid (COT) Kinase Inhibitors", Journal of Medicinal Chemistry, 2016, 59:7544-7560.
Goyal et al., "Models for anti-inflammatory activity of 8-substituted-4-anilino-6-aminoquinoline-3-carbonitriles", Med Chem Res, 2011, 21:1044-55.
Green et al., "Inhibitors of Tumor Progression Loci-2 (Tpl2) Kinase and Tumor Necrosis Factor oc (TNF-oc) Production: Selectivity and in Vivo Antiinflammatory Activity of Novel 8-Substituted-4-anilino-6-aminoquinoline-3-carbonitriles", J. Med. Chem., 2007, 50:4728-4745.
Gu et al., "A highly specific inhibitor of matrix metalloproteinase-9 rescues laminin from proteolysis and neurons from apoptosis in transient focal cerebral ischemia," The Journal of Neuroscience, 2005, 25(27):6401-6408.
Gupta et al., "Homolytic displacement at carbon. Part 3. First example of alpha-attack on the allenyl-and prop-2-ynyl-cobaloximes" J. Chem. Soc., Perkin Trans. 2, 1988, 1377-1383.
Guyatt et al., "A new measure of health status for clinical trials in inflammatory bowel disease," Gastroenterology, 1989, 96:804-810.
Hall et al., "Pharmacologic Inhibition of Tpl2 Blocks Inflammatory Responses in Primary Human Monocytes, Synoviocytes, and Blood", The Journal of Biological Chemistry, 2007, 282(46): 33295-33304.
Hirata et al., "Inhibition of tumor progression locus 2 protein kinase decreases lipopolysacchande-induced tumor necrosis factor alpha production due to the inhibition of the tip-associated protein induction in RAW264.7 cells", Biol Pharm Bull, 2010, 33(7):1233-7.
Hu et al., "Inhibition of Tpl2 kinase and TN Fa production with quinoline-3-carbonitriles for the treatment of rheumatoid arthritis", Bioorqanic & Medicinal Chemistiy Letters, 2006, 16:6067-6072.
Hu et al., "Discovery of indazoles as inhibitors of Tpl2 kinase", Bioorganic & Medicinal Chemistry Letters, 2011, 21(16): 4758-4761.
Kaila et al., "Identification of a novel class of selective Tpl2 kinase inhibitors: 4-Alkvlamino-fl, 7lnaohthvridine-3-carbonitriles", Bioorganic & Medicinal Chemistry, 2007, 15:6425-6442.

Kitamura et al., "A reagent for safe and efficient diazo-transfer to primary amines: 2-azido-1,3-dimethylimidazolinium hexafluorophosphate", Org. Biomol. Chem., 2014, 12:4397-4406.
McMahon et al., "VEGF Receptor Signaling in Tumor Angiogensis", The Oncologist, 2000, 5:3-10.
Mexican Office Action in Patent Application No. MX/a/2020/000232, dated Mar. 25, 2021, 9 pages (with partial English translation).
Nathubhai et al., "N3-alkylation during formation of quinazolin-4-ones from condensation of anthranilamides and orthoamides," Organic and Biomolecular Chemistry, 2011, 9(17):6089-6099.
Notice of Allowance dated Jun. 9, 2017 for U.S. Appl. No. 15/199,779, 11 pages.
Notice of Allowance dated Oct. 15, 2017 for U.S. Appl. No. 15/429,086, 10 pages.
Notice of Allowance dated Apr. 26, 2018 for U.S. Appl. No. 15/634,314, 5 pages.
Notice of Allowance dated Mar. 14, 2019 for U.S. Appl. No. 15/697,755, 12 pages.
Office Action dated Mar. 23, 2017 for U.S. Appl. No. 15/429,086, 19 pages.
Office Action dated Jun. 30, 2017 for U.S. Appl. No. 15/429,086, 15 pages.
Office Action dated Sep. 7, 2017 for U.S. Appl. No. 15/199,534, 37 pages.
Office action dated Oct. 18, 2017 for Taiwan Appl. No. 105121281, 3 pages (with English translation).
Office Action dated Dec. 18, 2017 for U.S. Appl. No. 15/634,314, 10 pages.
Office Action dated Jul. 5, 2018 for U.S. Appl. No. 15/697,755, 54 pages.
Office Action dated Feb. 14, 2019 for Chilean Appl. No. 201703356, 23 pages (with English translation).
Office Action dated Apr. 25, 2019 for Panamanian Appl. No. 91923, 8 pages (with English translation).
Office Action dated Jun. 19, 2019 for U.S. Appl. No. 16/045,518, 12 pages.
Office Action dated Aug. 2, 2019 for Mexican Appl No. MX/a/2017/004737, 6 pages (with English translation).
Office Action dated Aug. 7, 2019 for Taiwanese Appl No. 107117905, 4 pages.
Office Action dated Aug. 22, 2019 for U.S. Appl. No. 16/391,673, 7 pages.
Office Action dated Aug. 26, 2019 for India Appl. No. 201817004197, 7 pages (with English translation).
Office Action dated Sep. 27, 2019 for European Appl. No. 16741446.5, 4 pages.
Office Action dated Oct. 4, 2019 for U.S. Appl. No. 15/891,163, 24 pages.
Office Action dated Mar. 12, 2020 for Ukranian Appl. No. a2O1712984, 6 pages (with English translation).
Office Action in AR Appln. No. 20160102051, dated Jun. 1, 2020, 7pages (with English translation).
Office Action in ARIPO Appln. No. AP/P/2017/010402, dated Jun. 16, 2020, 5 pages.
Office Action in CN Appln. No. 201910292757.5, dated Dec. 23, 2020, 15 pages (with English translation).
Office Action in CR Appln. No. 2017-0599, dated Oct. 28, 2020, 17 pages (with English translation).
Office Action in DO Appln. No. 2017-0311, dated Aug. 24, 2020, 5 pages (with English translation).
Office Action in EP Appln. No. 18186568.4, dated May 5, 2020, 4 pages.
Office Action in GC Appln. No. 2016-31644, dated May 6, 2020, 3 pages.
Office Action in JP Appln. No. 2018-171794, dated Jun. 23, 2020, 6 pages (with English translation).
Office Action in JP Appln. No. 2019-137759, dated Jun. 16, 2020, 4 pages (with English translation).
Office Action in MX Appln. No. MX_a_2020-000232, dated Oct. 8, 2020, 5 pages.
Office Action in PH Appln. No. 1-2018-500031, dated Jun. 23, 2020, 4 pages.

(56) References Cited

OTHER PUBLICATIONS

Office Action in SA Appln. No. 517381350, dated Sep. 20, 2020, 7 pages (with English translation).
Office Action for Colombian Appl. No. NC2017/0013351, 6 pages.
PCT International Search Report and Written Opinion in International Appln. No. PCT/US2016/040552, dated Sep. 23, 2016, 9 pages.
PCT International Search Report and Written Opinion in International Appln. No. PCT/US2017/039418, dated Sep. 20, 2017, 9 pages.
PCT International Search Report and Written Opinion in International Appln. No. PCT/US2020/037214, dated Aug. 25, 2020, 13 pages.
PCT International]I Search Report and Written Opinion in International Appln. No. PCT/US2016/040520, dated Aug. 16, 2018, 11 pages.
Perugorria et al., "Tumor progression locus 2/Cot is required for activation of extracellular regulated kinase in liver injury and toll-like receptor-induced TIMP-1 gene transcription in hepatic stellate cells in mice," Hepatology, 2013, 57:1238-1249.
Pinedo et al., "Translational Research: The Role of VEGF in Tumor Angiogenesis", The Oncologist, 2000,5:1-2.
Preliminary Rejection dated Jun. 17, 2019 for Korean Appl. No. 10-2018-7003220, 12 pages (with English translation).
PubChem Database (2006) 4-Chloro-3-cyano-7-ethoxy-6-nitroquinoline, CID11011305, 14 pages.
PubChem Database (2006) 4-Chloro-6-nitro-quinoline-3-carbonitrile, CID11085690, 20 pages.
PubChem Database (2006) 4-Chloro-7-methoxy-6-nitroquinoline-3-carbonitrile, CID11139975, 20 pages.
PubChem Database (2006) 4-Chloro-8-methoxy-6-nitro-quinoline-3-carbonitrile, CID11129151, 20 pages.
PubChem Database (2007) 4,8-Dichloro-6-nitroquinoline-3-carbonitrile, CID17759323, 20 pages.
PubChem Database (2007) 4-Chloro-8-methyl-6-nitro-3 quinolinecarbonitrile, CID22466621, 20 pages.
PubChem Database (2013) 4-Chloro-7-[3-(morpholin-4-yl)propoxy]-6-nitroquinoline-3-carbonitrile, CID71425067, 9 pages.
Restriction Requirement dated Feb. 16, 2017 for U.S. Appl. No. 15/199,534, 13 pages.
Restriction Requirement dated Mar. 8, 2017 for U.S. Appl. No. 15/199,779, 10 pages.
Restriction Requirement dated Aug. 11, 2017 for U.S. Appl. No. 15/634,314, 6 pages.
Restriction Requirement dated Mar. 26, 2018 for U.S. Appl. No. 15/697,755, 6 pages.
Restriction Requirement dated Jun. 29, 2018 for U.S. Appl. No. 15/891,163, 12 pages.
Restriction Requirement dated Feb. 8, 2019 for U.S. Appl. No. 16/045,518, 5 pages.
Search Report dated Feb. 5, 2019 for European Appl. No. 18186568.4, 5 pages.
Teli et al., "Pharmacophore generation and atom-based 3D-QSAR of novel quinoline-3-carbonitrile derivatives as Tpl2 kinase inhibitors", Journal of Enzyme Inhibition and Medicinal Chemistry, 2012, 27(4): 558-570.

Truelove et al., "Cortisone in ulcerative colitis; final report on a therapeutic trial," Br Med J., 1955, 2(4947):1041-1048.
Vyrla et al., "TPL2 Kinase Is a Crucial Signaling Factor and Mediator of NKT Effector Cytokine Expression in Immune-Mediated Liver Injury," The Journal of Immunology, 2016, 196(10):4298-310.
Wissner et al., "Syntheses and EGFR kinase inhibitory activity of 6-substituted-4-anilino [1,7] and [1,8] naphthyridine-3-carbonitriles", Bioorg. Med. Chem. Lett, 2004, 14(6):1411-6.
Wu et al., "Selective inhibitors of tumor progression loci-2 (Tpl2) kinase with potent inhibition of TNF-α production in human whole blood", Bioorganic & Medicinal Chemistry Letters, 2009, 19:3485-3488.
Zhu et al., "Anti-TNF-alpha therapies in systemic lupus erythematosus", J Biomed Biotechnol., 2010, 8 pages.
U.S. Appl. No. 15/199,779, filed Jun. 30, 2016, Elizabeth M. Bacon.
U.S. Appl. No. 15/697,755, filed Sep. 7, 2017, Elizabeth M. Bacon.
U.S. Appl. No. 16/717,074, filed Dec. 17, 2019, Elizabeth M. Bacon.
U.S. Appl. No. 16/045,518, filed Jul. 25, 2018, Gayatri Balan.
U.S. Appl. No. 15/634,314, filed Jun. 27, 2017, Gayatri Balan.
Ghosh, "Anti-TNF therapy in Crohn's disease," Inflammatory Bowel Disease: Crossroads of Microbes, Epithelium and Immune Systems, Novartis Foundation Symposium, Nov. 2004, 263:193-205.
Gisbert et al., "Vedolizumab en el tratamiento de la enfermedad de Crohn," Gastroenterologia y Hepatologia, Jan. 2015, 38(5): 338-348 (with English abstract).
Gonzalez-Cabrera et al., "SIP signaling: new therapies and opportunities," F1000Prime Reports, Dec. 2014, 6(109):1-7.
Marshall et al., "Selective Allosteric Inhibition of MMP9 Is Efficacious in Preclinical Models of Ulcerative Colitis and Colorectal Cancer," PLoS One, May 2015, 10(5): pp. 1-26.
Nunes et al., "Oral locally active steroids in inflammatory bowel disease," Journal of Crohn's and Colitis, Apr. 2013, 7(3): 183-191.
Smith et al., "Vedolizumab: An α4β7 Integrin Inhibitor for Inflammatory Bowel Diseases", Annals of Pharmacotherapy, Sep. 2014, 7 pages.
Exam Report dated Jul. 12, 2021 for Indian Appl. No. 201817004204, 3 pages.
Office Action in BR Appln. No. BR102016015656-4, dated Mar. 30, 2021, 4 pages (English Translation Only).
Office Action in CN Appln. No. 201910292757.5, dated Jul. 27, 2021, 12 pages (with English translation).
Office Action in DO Appln,. No. P2017-0311, dated Jul. 7, 2021, 6 pages (with English Translation).
Office Action in GC Appln No. 39905, dated Aug. 8, 2021, 4 pages.
Office Action in MX Appln. No. MX/a/2020/000232, dated Mar. 25, 2021, 9 pages (with partial English translation).
Office Action in MX Appln. No. MX/a/2020/000232, dated Sep. 28, 2021, 20 pages (with English translation).
Office Action in PE Appln. No. 002804-2017/DIN, dated Jun. 30, 2021, 14 pages (with English translation).
Office Action in TW Appln No. 109119416, dated Aug. 11, 2021, 20 pages (with English translation).

* cited by examiner

COT MODULATORS AND METHODS OF USE THEREOF

CROSS REFERENCE TO RELATED APPLICATIONS

This application is a divisional of U.S. application Ser. No. 16/994,889, filed on Aug. 17, 2020, which is a continuation of U.S. application Ser. No. 16/898,981, filed on Jun. 11, 2020, which claims the benefit of U.S. Provisional Application No. 62/861,390 filed on Jun. 14, 2019, the disclosure of each of these applications is hereby incorporated by reference in its entirety

FIELD

The present disclosure relates generally to modulators of Cot (cancer Osaka thyroid) and methods of use and manufacture thereof.

BACKGROUND

Cot (cancer Osaka thyroid) protein is a serine/threonine kinase that is a member of the MAP kinase kinase kinase (MAP3K) family. It is also known as "TPL2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

Agents and methods that modulate the expression or activity of Cot, therefore, may be useful for preventing or treating such diseases.

SUMMARY

The present disclosure provides compounds that modulate the expression or activity of Cot. The disclosure also provides compositions, including pharmaceutical compositions, kits that include the compounds, and methods of using (or administering) and making the compounds. The compounds provided herein can be useful in treating diseases, disorders, or conditions that are mediated by Cot. The disclosure also provides compounds for use in therapy. The disclosure further provides compounds for use in a method of treating a disease, disorder, or condition that is mediated by Cot. Moreover, the disclosure provides uses of compounds in the manufacture of a medicament for the treatment of a disease, disorder or condition that is mediated by (or mediated, at least in part, by) Cot.

In one aspect, provided is a compound having structure of Formula I:

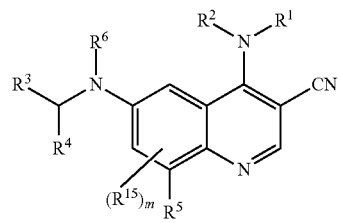

(I)

wherein
$R^1$ is hydrogen, —O—$R^7$, —N($R^8$)($R^9$), —C(O)—$R^7$, —S(O)$_2$—$R^7$, —C$_{1-9}$ alkyl, C$_{2-6}$ alkenyl, C$_{2-6}$ alkynyl, C$_{3-15}$ cycloalkyl, heterocyclyl, aryl, or heteroaryl;
  wherein each C$_{1-9}$ alkyl, C$_{2-6}$ alkenyl, C$_{2-6}$ alkynyl, C$_{3-15}$ cycloalkyl, heterocyclyl, aryl, and heteroaryl may be optionally substituted with one to four $Z^1$;
$R^2$ is hydrogen, —C(O)—$R^7$, —C(O)O—$R^7$, —C(O)N($R^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^2$;
or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;
$R^4$ is aryl, heterocyclyl or heteroaryl, wherein each aryl, heterocyclyl, or heteroaryl is optionally substituted with one to four $Z^4$;
$R^5$ is hydrogen, halo, —CN, —NO$_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, and heteroaryl may be optionally substituted with one to four $Z^5$;
$R^6$ is —C(O)O—$R^{16}$—OP(O)(O$R^{12}$)$_2$—C(O)—$R^{16}$—OP(O)(O$R^{12}$)$_2$, —$R^{16}$—OP(O)(O$R^{12}$)$_2$, —C(O)O—$R^{16}$—O$R^{17}$, —C(O)O—$R^{16}$—OH; —C(O)O—$R^{16}$—OC(O)$R^{17}$; —C(O)—C(O)O$R^{12}$, or —C(O)O—$R^{16}$—OC(O)$R^{17}$NH$_2$;
each $R^7$ is independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^7$;
$R^8$ and $R^9$ at each occurrence are independently hydrogen, —S(O)$_2R^{10}$, —C(O)—$R^{10}$, —C(O)O—$R^{10}$, —C(O)N($R^{10}$)($R^{11}$), C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl may be optionally substituted with one to four $Z^8$;
$R^{10}$ and $R^{11}$ at each occurrence are independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$, and $Z^8$ is independently hydrogen, oxo, halo, —$NO_2$, —$N_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)+, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —$CH_2$P(O)O$R^{12}$)$_2$, —O$CH_2$P(O)(O$R^{12}$)$_2$, —C(O)O$CH_2$P(O)(O$R^{12}$)$_2$, —P(O)($R^{12}$)(O$R^{12}$), —OP(O)($R^{12}$)(O$R^{12}$), —$CH_2$P(O)($R^{12}$)(O$R^{12}$), —O$CH_2$P(O)($R^{12}$)(O$R^{12}$), —C(O)O$CH_2$P(O)($R^{12}$)(O$R^{12}$), —P(O)(N($R^{12}$)$_2$)$_2$, —OP(O)(N($R^{12}$)$_2$)$_2$, —$CH_2$P(O)(N($R^{12}$)$_2$)$_2$, —O$CH_2$P(O)(N($R^{12}$)$_2$)$_2$, —C(O)O$CH_2$P(O)(N($R^{12}$)$_2$)$_2$, —P(O)(N($R^{12}$)$_2$)(O$R^{12}$), —OP(O)(N($R^{12}$)$_2$)(O$R^{12}$), —$CH_2$P(O)(N($R^{12}$)$_2$)(O$R^{12}$), —O$CH_2$P(O)(N($R^{12}$)$_2$)(O$R^{12}$), —C(O)O$CH_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —$CH_2$P(O)($R^{12}$)(N($R^{12}$)$_2$), —O$CH_2$P(O)($R^{12}$)(N($R^{12}$)$_2$), —C(O)O$CH_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)+, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $R^{15}$ is independently halo, —CN, —$NO_2$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;

$R^{16}$ is —$C_{1-3}$ alkyl or cyclopropyl optionally substituted with one to four $C_{1-3}$ alkyl or cyclopropyl;

$R^{17}$ is $C_{1-9}$ alkyl, cycloalkyl, or heterocyclyl optionally substituted with one to three $R^{16}$;

and each $Z^1$, $Z^2$, $Z^4$, $Z^5$, $Z^7$, and $Z^8$ is independently hydrogen, oxo, halo, —$NO_2$, —$N_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O) O—$R^{12}$, —C(O)—N($R^{13}$)($R^{14}$), —N($R^{13}$)($R^{14}$), —N($R^{13}$)$_2$ ($R^{14}$)+, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —$CH_2$P(O)O$R^{12}$)$_2$, —O$CH_2$P(O)(O$R^{12}$)$_2$, —C(O)O$CH_2$P (O)(O$R^{12}$)$_2$, —P(O)($R^{12}$)(O$R^{12}$), —OP(O)($R^{12}$)(O$R^{12}$), —$CH_2$P(O)($R^{12}$)(O$R^{12}$), —O$CH_2$P(O)($R^{12}$)(O$R^{12}$), —C(O)O$CH_2$P(O)($R^{12}$)(O$R^{12}$), —P(O)(N($R^{12}$)$_2$)$_2$, —OP (O)(N($R^{12}$)$_2$)$_2$, —$CH_2$P(O)(N($R^{12}$)$_2$)$_2$, —O$CH_2$P(O)(N ($R^{12}$)$_2$)$_2$, —C(O)O$CH_2$P(O)(N($R^{12}$)$_2$)$_2$, —P(O)(N($R^{12}$)$_2$) (O$R^{12}$), —OP(O)(N($R^{12}$)$_2$)(O$R^{12}$), —$CH_2$P(O)(N($R^{12}$)$_2$) (O$R^{12}$), —O$CH_2$P(O)(N($R^{12}$)$_2$)(O$R^{12}$), —C(O)O$H_2$P(O)(N ($R^{12}$)$_2$)(O$R^{12}$), —P(O)($R^{12}$)(N($R^{12}$)$_2$), —OP(O)($R^{12}$)(N ($R^{12}$)$_2$), —$CH_2$P(O)($R^{12}$)(N($R^{12}$)$_2$), —O$CH_2$P(O)($R^{12}$)(N ($R^{12}$)$_2$), C(O)O$H_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

$Z^9$ is hydrogen, halo, —CN, or —O—$R^{12}$;

each $Z^{1a}$ is independently oxo, halo, thioxo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$) ($R^{14}$), —N($R^{13}$)($R^{14}$), —N($R^{13}$)$_2$($R^{14}$)+, —N($R^{12}$)—C(O) $R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC (O)—N($R^{13}$)($R^{14}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, aryl, heteroaryl or heterocyclyl is optionally substituted with one to four $Z^{1b}$ groups;

each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH (aryl), —NH(heteroaryl), —NH(heterocyclyl), —N($C_{1-9}$ alkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O) ($C_{1-8}$ haloalkyl), —C(O)(aryl), —C(O)(heteroaryl), —C(O) (heterocyclyl), —C(O)O$C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH ($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N ($C_{2-6}$ alkenyl)$_2$, —C(O)N($C_{2-6}$ alkynyl)$_2$, —C(O)

N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof. Some embodiments provide a method of using (or administering) the compounds of Formula I, or additional Formula(s) described throughout, in the treatment of a disease or condition in a mammal, such as a human, that is amenable to treatment by a Cot modulator.

In certain embodiments, the disclosure provides pharmaceutical compositions comprising a therapeutically effective amount of a compound of the disclosure (e.g. a compound of Formula I or additional Formula(s) described throughout), and at least one pharmaceutically acceptable excipient.

DETAILED DESCRIPTION

Figure 1:
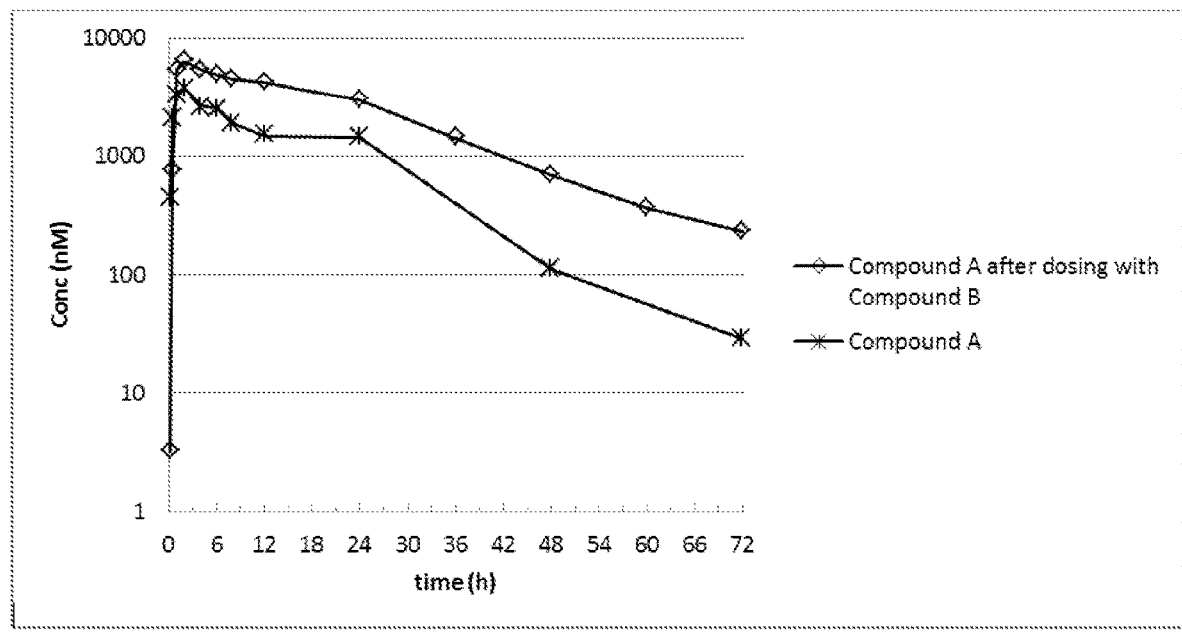
FIG. 1 depicts plasma concentration over time of Compound A following oral administration of Compound B to dogs compared to oral administration of Compound A over time.

The present disclosure relates to inhibitors of Cot, or TPL2. The disclosure also relates to compositions and methods relating to inhibitors of TPL2 and the use of such compounds for treatment and prophylaxis of diseases and conditions through binding of TPL2 with said compounds. The disclosure also relates to compositions and methods for treating and preventing cancer, diabetes, inflammatory disease, or liver disease including a TPL2 inhibitor in combination with one or more additional therapeutic agents.

A number of Cot inhibitors are known and are being investigated in connection with a number of physiological conditions, including for example inflammatory diseases. Cot, or TPL2, has been shown to regulate oncogenic and inflammatory pathways. TPL2 was identified by its oncogenic transforming activity in cells and has been shown to regulate oncogenic and inflammatory pathways. TPL2 is expressed in a broad range of immune cells and regulates ERK-mediated gene expression downstream of multiple stimuli, including for example bacterial products, such as LPS and bacterial peptidoglycans, TNFα, and IL-1β. In inflammatory bowel disease, for instance, intestinal inflammation reflects the loss of a homeostatic relationship between intestinal microbiota and the host immune system. In IBD, the homeostatic response to commensal bacteria can be replaced by sustained and exacerbated immune signaline. TPL2 inhibition can provide an opportunity to restor immune homeostasis, for example, in IBD patients by attenuating exacerbated inflammatory signaling.

Embodiments of the present disclosure provide compounds that provide inhibition of TPL2. In some embodiments, compounds disclosed herein exhibit desirable pharmacokinetic properties. In some embodiments, compounds disclosed herein are cleaved, for example intestinally-cleaved, to provide compounds that inhibit TPL2. In some embodiments, compounds disclosed herein have improved solubility in comparison with known inhibitors of TPL2. In some embodiments, compounds disclosed herein provide improved systemic exposure of TPL2 inhibitors relative to known compounds.

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed thus, for example, "butyl" includes n-butyl (i.e. —$(CH_2)_3CH_3$), sec-butyl. (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Amidino" refers to —C(NH)(NH$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthylenyl, fluorenyl, and anthracenyl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to —N$_3$.

"Carbamoyl" refers to both an "0-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond), As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Guanidino" refers to —NHC(NH)(NH$_2$).

"Hydrazino" refers to —NHNH$_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and judo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single ring or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or Spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Oxo" refers to the group (=O) or (O).

"Nitro" refers to the group —NO$_2$.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Alkylsulfonyl" refers to the group —S(O)$_2$R, where R is alkyl.

"Alkylsulfinyl" refers to the group —S(O)R, where R is alkyl.

"Thiocyanate"—SCN.

"Thiol" refers to the group —SR, where R is alkyl, haloalkyl, heterocyclyl, cycloalkyl, heteroaryl, or aryl.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last-mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$F), $^{32}$F), $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, such as a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a certain isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In some cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazine, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Compounds

Provided herein are compounds that function as modulators of Cot. In one aspect, provided is a compound having structure of Formula I:

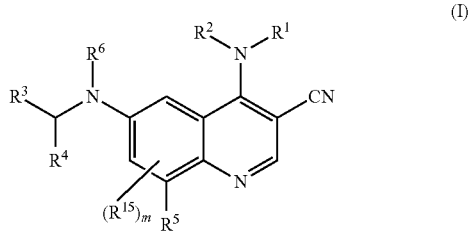

(I)

wherein
$R^1$ is hydrogen, $-O-R^7$, $-N(R^8)(R^9)$, $-C(O)-R^7$, $-S(O)_2-R^7$, $C_{1-9}$ alkyl, $C_{2-6}$ alkenyl, $C_{2-6}$ alkynyl, $C_{3-15}$ cycloalkyl, heterocyclyl, aryl, or heteroaryl;
  wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;
$R^2$ is hydrogen, $-C(O)-R^7$, $-C(O)O-R^7$, $-C(O)N(R^7)_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;
or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;
$R^4$ is aryl, heterocyclyl or heteroaryl, wherein each aryl, heterocyclyl, or heteroaryl is optionally substituted with one to four $Z^4$;
$R^5$ is hydrogen, halo, $-CN$, $-NO_2$, $-O-R^7$, $-N(R^8)(R^9)$, $-S(O)-R^7$, $-S(O)_2R^7$, $-S(O)_2N(R^7)_2$, $-C(O)R^7$, $-OC(O)-R^7$, $-C(O)O-R^7$, $-OC(O)O-R^7$, $-OC(O)N(R^{10})(R^{11})$, $-C(O)N(R^7)_2$, $-N(R^7)C(O)(R^7)$, $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is $-C(O)O-R^{16}-OP(O)(OR^{12})_2$ $-C(O)-R^{16}-OP(O)(OR^{12})_2$, $-R^{16}-OP(O)(OR^{12})_2$, $-C(O)O-R^{16}-OR^{17}$; $-C(O)O-R^{16}-OH$; $-C(O)O-R^{16}-OC(O)R^{17}$; $-C(O)-C(O)OR^{12}$, or $-C(O)O-R^{16}-OC(O)R^{17}NH_2$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;
$R^8$ and $R^9$ at each occurrence are independently hydrogen, $-S(O)_2R^{10}$, $-C(O)-R^{10}$, $-C(O)O-R^{10}$, $-C(O)N(R^{10})(R^{11})$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;
$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;
each $Z^1$, $Z^2$, $Z^3$, $Z^4$, $Z^5$, $Z^6$, $Z^7$, and $Z^8$ is independently hydrogen, oxo, halo, $-NO_2$, $-N_3$, $-CN$, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^{12}$, $-C(O)-R^{12}$, $-C(O)O-R^{12}$, $-C(O)-N(R^{13})(R^{14})$, $-N(R^{13})(R^{14})$, $-N(R^{13})_2(R^{14})+$, $-N(R^{12})C(O)-R^{12}$, $-N(R^{12})C(O)O-R^{12}$, $-N(R^{12})C(O)N(R^{13})(R^{14})$, $-N(R^{12})S(O)_2(R^{12})$, $-NR^{12}S(O)_2N(R^{13})(R^{14})$, $-NR^{12}S(O)_2O(R^{12})$, $-OC(O)R^{12}$, $-OC(O)-N(R^{13})(R^{14})$, $-P(O)$ (OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four Z$^{1a}$ groups;

each Z$^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)+, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups;

each R$^{15}$ is independently halo, —CN, —NO$_2$, —O—R$^7$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R$^7$)C(O)(R$^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl;

R$^{16}$ is —C$_{1-3}$ alkyl or cyclopropyl optionally substituted with one to four C$_{1-3}$ alkyl or cyclopropyl;

R$^{17}$ is C$_{1-9}$ alkyl, cycloalkyl, or heterocyclyl optionally substituted with one to three R$^{16}$; and each Z$^1$, Z$^2$, Z$^4$, Z$^5$, Z$^7$, and Z$^8$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)+, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$. —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four Z$^{1a}$ groups;

Z$^9$ is hydrogen, halo, —CN, or —O—R$^{12}$;

each Z$^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)+, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four Z$^{1b}$ groups;

each Z$^{1b}$ is independently oxo, thioxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH (heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof. Some embodiments provide a method of using (or administering) the compounds of Formula I, or additional Formula(s) described throughout, in the treatment of a disease or condition in a mammal, such as a human, that is amenable to treatment by a Cot modulator.

In one aspect, provided is a compound having structure of Formula IA:

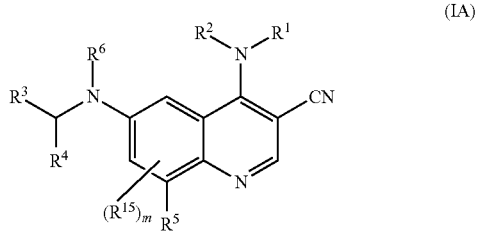

(IA)

wherein
$R^1$ is hydrogen, —O—$R^7$, —N($R^8$)($R^9$), —C(O)—$R^7$, —S(O)$_2$—$R^7$, —$C_{1-9}$ alkyl, $C_{2-6}$ alkenyl, $C_{2-6}$ alkynyl, $C_{3-15}$ cycloalkyl, heterocyclyl, aryl, or heteroaryl;
wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;
$R^2$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;

or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;
$R^4$ is aryl, heterocyclyl or heteroaryl, wherein each aryl, heterocyclyl, or heteroaryl is optionally substituted with one to four $Z^4$;
$R^5$ is hydrogen, halo, —CN, —NO$_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is —C(O)O—$R^{16}$—OP(O)(O$R^{12}$)$_2$—C(O)—$R^{16}$—OP(O)(O$R^{12}$)$_2$, —C(O)O—$R^{16}$—OP(O)(O$R^{12}$)$_2$, —$R^{16}$—OP(O)(O$R^{12}$)$_2$, —C(O)O—$R^{16}$—O$R^{17}$; —C(O)O—$R^{16}$—OH; —C(O)O—$R^{16}$—OC(O)$R^{17}$; or —C(O)O—$R^{16}$—OC(O)$R^{17}$NH$_2$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;
$R^8$ and $R^9$ at each occurrence are independently hydrogen, —S(O)$_2R^{10}$, —C(O)—$R^{10}$, —C(O)O—$R^{10}$, —C(O)N($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;
$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;
each $Z^1$, $Z^2$, $Z^3$, $Z^4$, $Z^5$, $Z^6$, $Z^7$, and $Z^8$ is independently hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)+, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —CH$_2$P(O)(O$R^{12}$)$_2$, —OCH$_2$P(O)(O$R^{12}$)$_2$, —C(O)CH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$). —C(O)OCH$_2$P(O)($R^{12}$)(O$R^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$. —C(O)OCH$_2$P(O)(N($R^{12}$)$_2$)$_2$. —P(O)(N($R^{12}$)$_2$)(O$R^{12}$), —OP(O)(N($R^{12}$)$_2$)(O$R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$). —C(O)OCH$_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four $Z^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or R$^{13}$ and R$^{14}$ together with the nitrogen to which they are attached form a heterocyclyl, wherein said heterocyclyl is optionally substituted with one to four $Z^{1b}$ groups;

each R$^{15}$ is independently halo, —CN, —NO$_2$, —O—R$^7$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R$^7$)C(O)(R$^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl;

R$^{16}$ is —C$_{1-2}$ alkyl optionally substituted with one to four C$_{1-2}$ or cyclopropyl;

R$^{17}$ is C$_{1-9}$ alkyl, cycloalkyl, or heterocyclyl optionally substituted with one to three R$^{16}$;

and each $Z^1$, $Z^2$, $Z^4$, $Z^5$, $Z^7$, and $Z^8$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —OCH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)CH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four $Z^{1a}$ groups;

$Z^9$ is hydrogen, halo, —CN, or —O—R$^{12}$;

each $Z^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four $Z^{1b}$ groups;

each $Z^{1b}$ is independently oxo, thioxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof.

In certain embodiments, the compound of Formula I is represented by Formula IB:

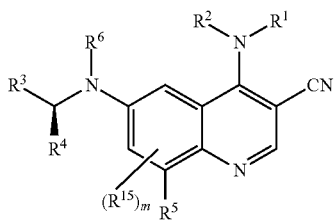

(IB)

wherein $R^1$-$R^6$, $R^{15}$ and m are as described herein.

In certain embodiments, the compound of Formula I is represented by Formula IC:

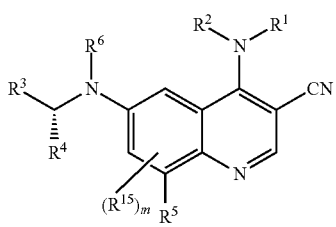

(IC)

wherein $R^1$-$R^6$, $R^{15}$ and m are as described herein.

In certain embodiments, m is 0. In certain embodiments, $R^2$ is hydrogen.

In certain embodiments, the compound of Formula I is represented by Formula II:

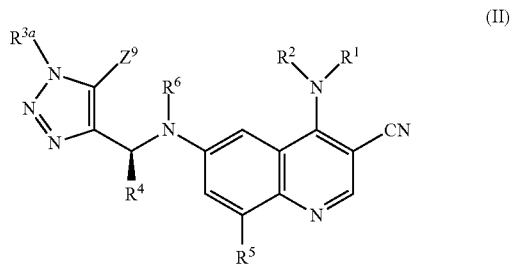

(II)

wherein $R^1$ is hydrogen, —O—$R^7$, —N($R^8$)($R^9$), —C(O)—$R^7$, —S(O)$_2$—$R^7$, —$C_{1-9}$ alkyl, $C_{2-6}$ alkenyl, $C_{2-6}$ alkynyl, $C_{3-15}$ cycloalkyl, heterocyclyl, aryl, or heteroaryl;
wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;

$R^2$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;

or $R^1$ and $R^2$ together with the nitrogen to which they are attached form a heterocyclyl or heteroaryl, wherein each heterocyclyl or heteroaryl is optionally substituted with one to four $Z^2$;

$R^{3a}$ is hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —NR$^{12}$S(O)$_2$N($R^{13}$)($R^{14}$), —NR$^{12}$S(O)$_2$O($R^{12}$), —OC(O)R$^{12}$, —OC(O)—N($R^{13}$)($R^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four $Z^{1a}$ groups;

$R^4$ is aryl, heterocyclyl or heteroaryl, wherein each aryl, heterocyclyl, or heteroaryl is optionally substituted with one to four $Z^4$;

$R^5$ is hydrogen, halo, —CN, —NO$_2$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R$^7$)C(O)(R$^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

$R^6$ is —C(O)O—$R^{16}$—OP(O)(O$R^{12}$)$_2$;

each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2$R$^{10}$, —C(O)—R$^{10}$, —C(O)O—R$^{10}$, —C(O)N(R$^{10}$)(R$^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

$R^{16}$ is —$C_{1-2}$ alkyl optionally substituted with one to four $C_{1-2}$ or cyclopropyl;

and each $Z^1$, $Z^2$, $Z^4$, $Z^5$, $Z^7$, and $Z^8$ is independently hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)+, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four $Z^{1a}$ groups;

$Z^9$ is hydrogen, halo, —CN, or —O—R$^{12}$;

each $Z^{1a}$ is independently oxo, halo, thioxo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)+, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four $Z^{1b}$ groups;

each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), haloalkyl), —O(aryl), —O(heteroaryl), —O(heterocyclyl), or —O($C_{1-9}$ alkyl);

or a pharmaceutically acceptable salt, stereoisomer, mixture of stereoisomers, or deuterated analog thereof.

In certain embodiments, $R^{3a}$ is hydrogen, $C_{1-9}$ alkyl, $C_{3-15}$ cycloalkyl, heterocyclyl, aryl, or heteroaryl, wherein said $C_{1-9}$ alkyl, $C_{3-15}$ cycloalkyl, aryl, or heterocyclyl, may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, Si($R_{12}$)$_3$, $C_{1-9}$ alkyl, $C_{1-8}$ haloalkyl, $C_{3-15}$ cycloalkyl, aryl, heterocyclyl, and heteroaryl; and wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In some embodiments, $R^{3a}$ is hydrogen or $C_{1-9}$ alkyl; wherein said $C_{1-9}$ alkyl may be optionally substituted with one to four substituents independently selected from the group consisting of cyano, halo, —O—$R^{12}$, —C(O)—$R^{12}$, —OC(O)O—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R_{12}$, —Si($R^{12}$)$_3$, $C_{1-8}$ haloalkyl, $C_{3-15}$ cycloalkyl, aryl, heterocyclyl, and heteroaryl; and wherein said $C_{3-15}$ cycloalkyl, aryl, heterocyclyl, or heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl, or a pharmaceutically acceptable salt thereof.

In certain embodiments, $R^{3a}$ is $C_{3-15}$ cycloalkyl, heterocyclyl, aryl, or heteroaryl; wherein said $C_{1-9}$ alkyl, $C_{3-15}$ cycloalkyl, aryl, or heterocyclyl, may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R_{12}$, —Si($R^{12}$)$_3$, $C_{1-9}$ alkyl, $C_{1-8}$ haloalkyl, $C_{3-15}$ cycloalkyl, aryl, heterocyclyl, and heteroaryl; and wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In some embodiments, $R^{3a}$ is $C_{3-15}$ cycloalkyl optionally substituted with one to four substituents independently selected from the group consisting of cyano, halo, —O—$R^{12}$, —C(O)O—$R^{12}$, —OC(O)—$R^{12}$, N($R^{13}$)$_2$($R^{14}$), —N($R^{13}$)($R^{14}$)$^+$, $C_{1-9}$ alkyl, $C_{1-8}$ haloalkyl, heterocyclyl, and heteroaryl.

In certain embodiments, $R^4$ is aryl optionally substituted with one to three substituents independently selected from the group consisting of CN, halo, —O—$R^{12}$, —C(O)—$R^{12}$, —C(O)O—$R^{12}$, —S(O)$_2$—$R^{12}$, —N($R^{12}$)C(O)—$R^{12}$, —N($R^{12}$)S(O)$_2$$R^{12}$, —C(O)N($R^{13}$)($R^{14}$), —N($R^{13}$)($R^{14}$), $C_{1-9}$ alkyl, $C_{3-15}$ cycloalkyl, heterocyclyl, aryl, and heteroaryl; wherein said $C_{1-9}$ alkyl, $C_{3-15}$ cycloalkyl, or heteroaryl may be optionally substituted with one to three substituents independently selected from the group consisting of halo, —CN, —O—$R^{12}$, —N($R^{13}$)($R^{14}$), $C_{1-9}$ alkyl, and heterocyclyl.

In some embodiments, $R^4$ is

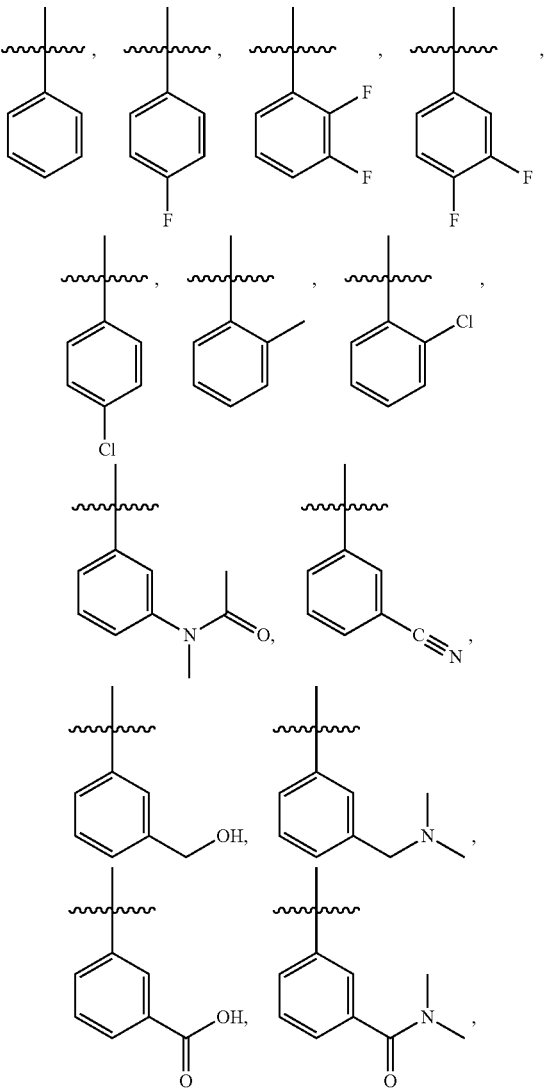

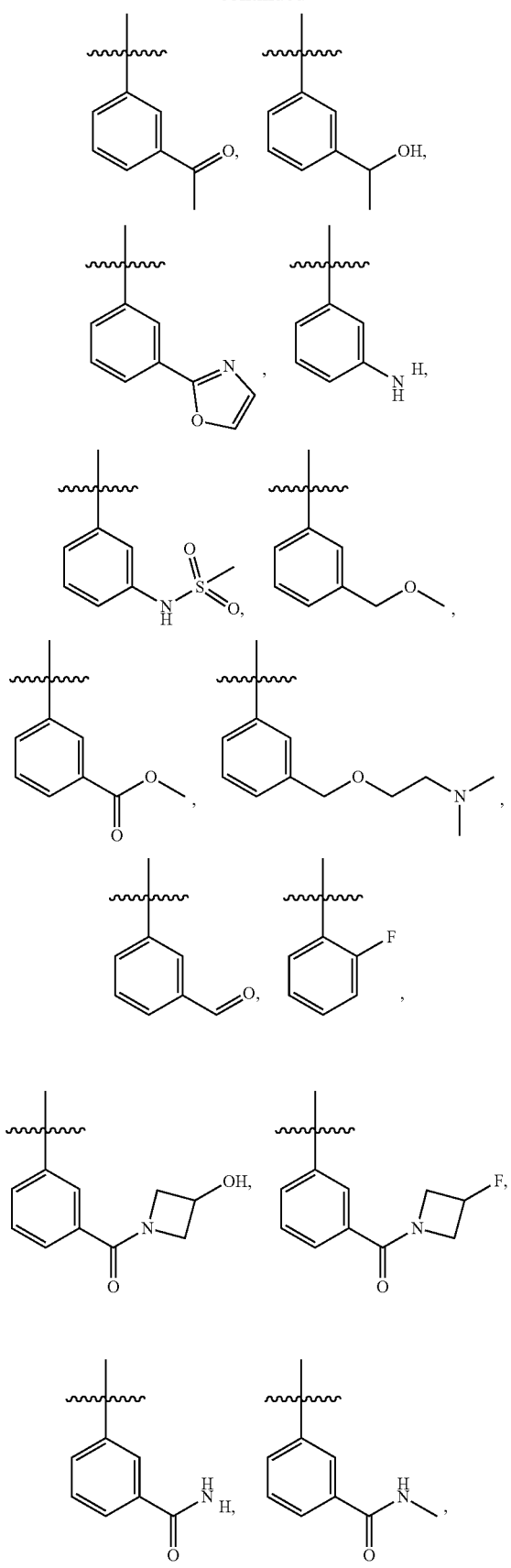
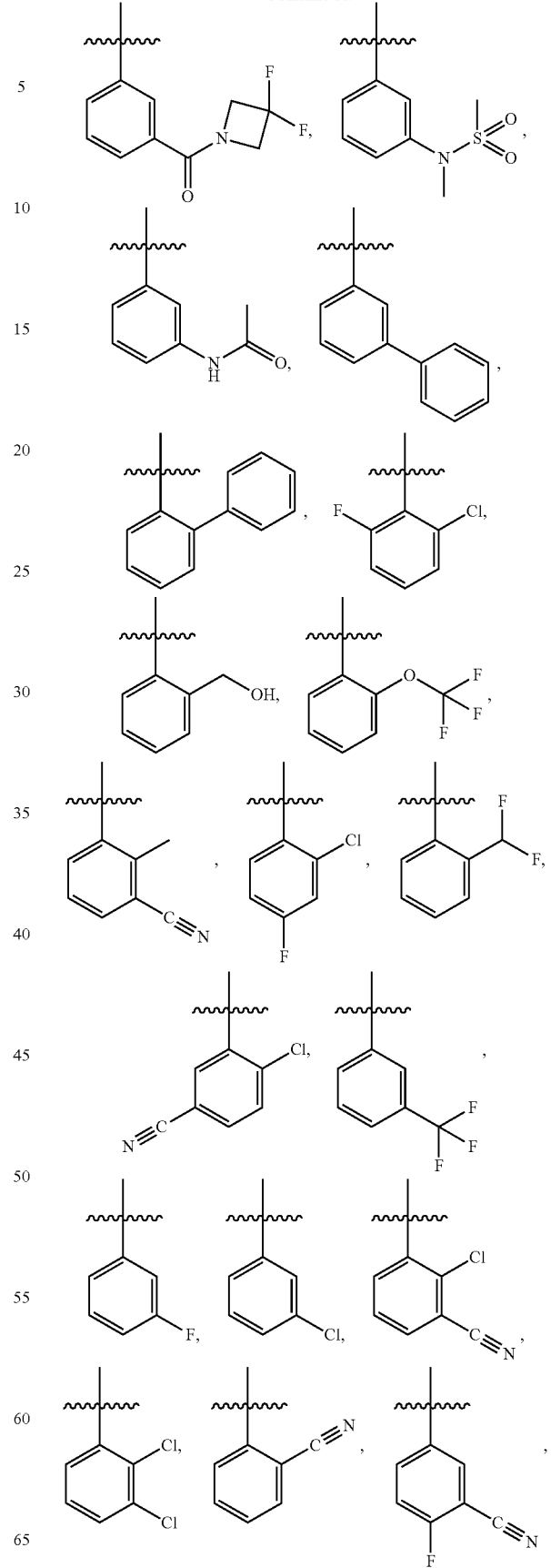

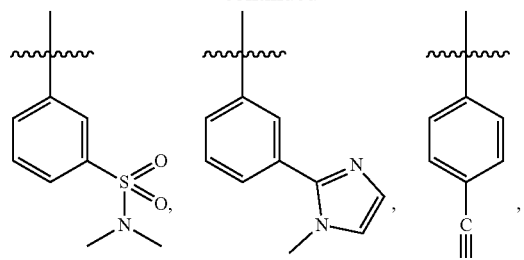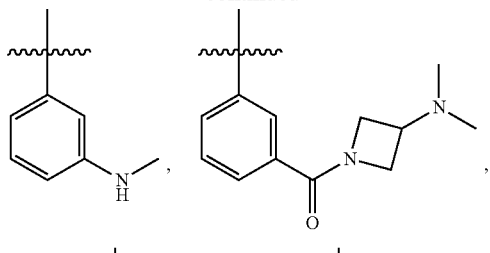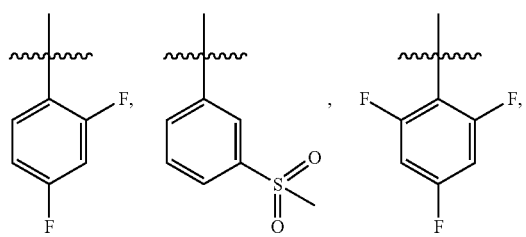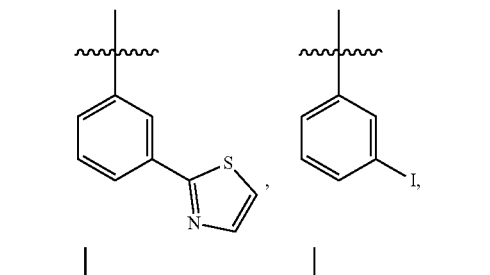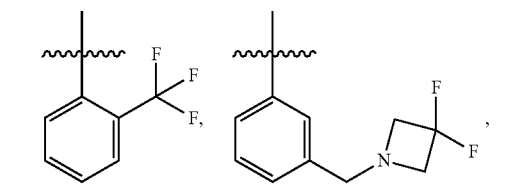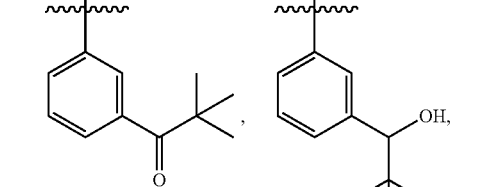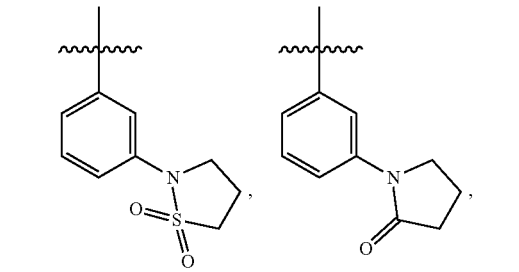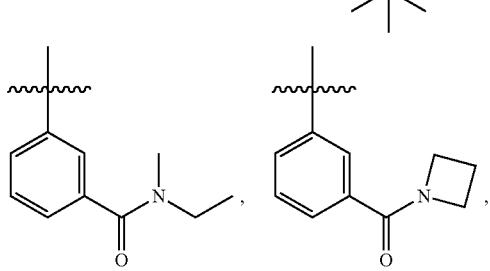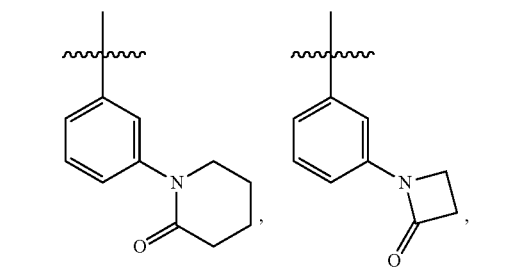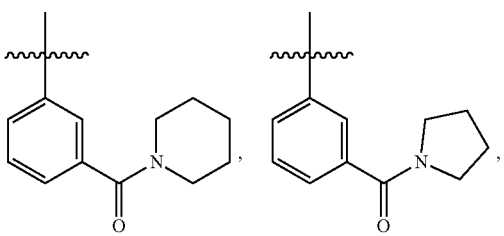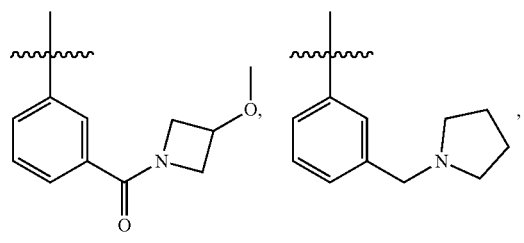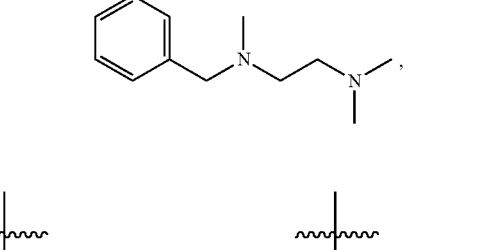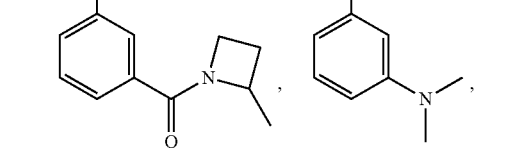

-continued
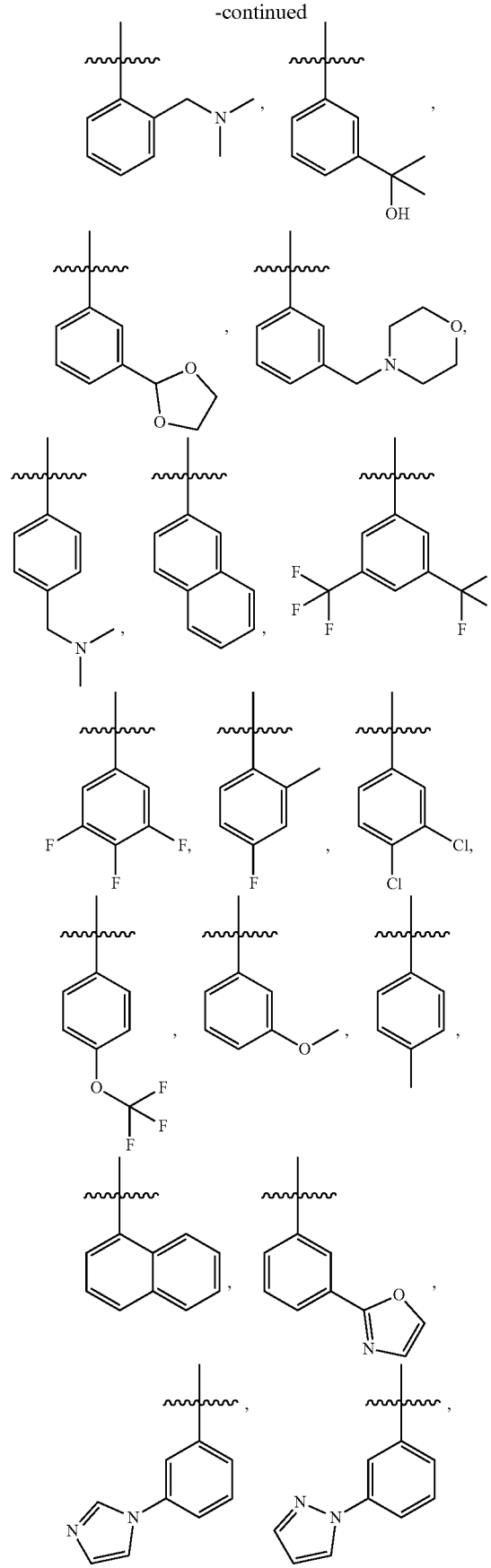
-continued
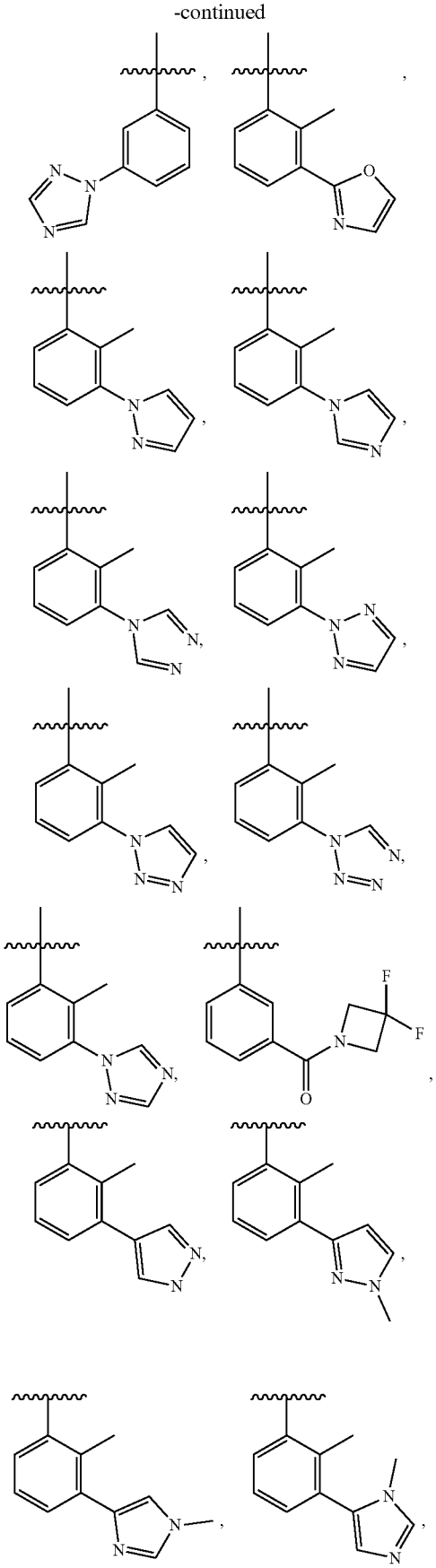

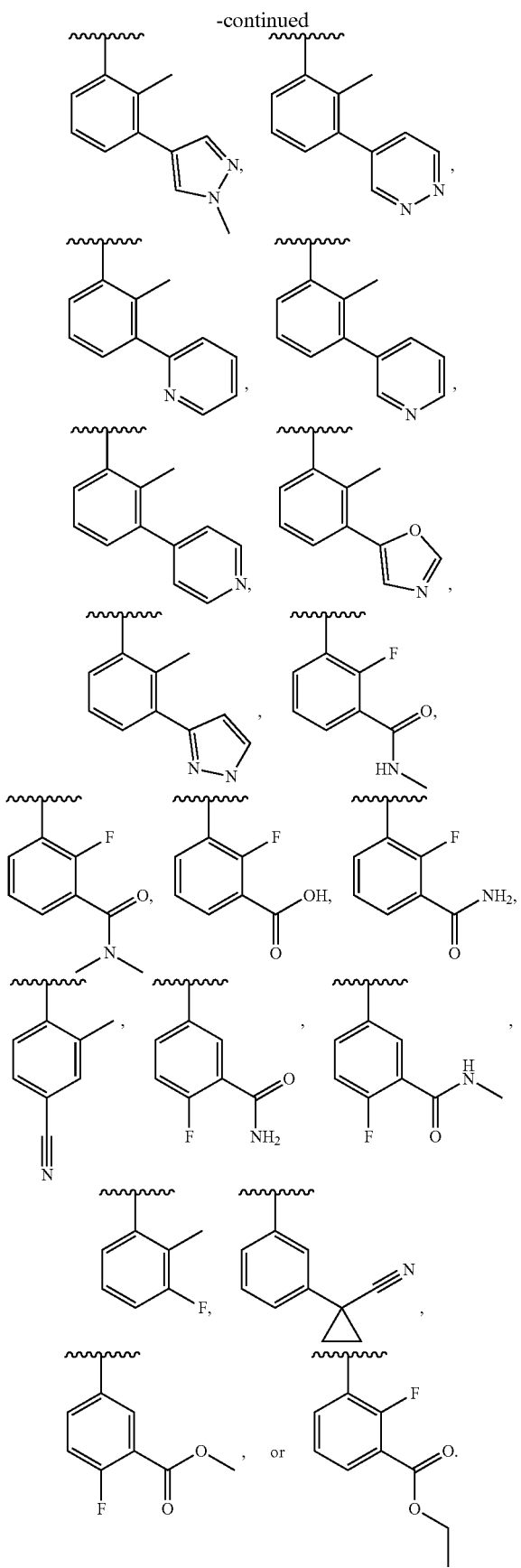

In some embodiments, R[4] is heterocyclyl, or heteroaryl optionally substituted with one to three substituents independently selected from the group consisting of cyano, halo and $C_{1-9}$ alkyl.

In certain embodiments, R[4] is heterocyclyl or heteroaryl; and said heterocyclyl or heteroaryl is optionally substituted with one to three substituents independently selected from the group consisting of —CN, halo, —O—R[12], —C(O)—R[12], —N(R[13])(R[14]), $C_{1-9}$ alkyl, $C_{1-8}$ haloalkyl, and heterocyclyl.

In certain embodiments, R[4] is heteroaryl optionally substituted with one to three substituents independently selected from the group consisting of —CN, halo, —O—R[12], —C(O)—R[12], —N(R[13])(R[14]), $C_{1-9}$ alkyl, $C_{1-8}$ haloalkyl, and heterocyclyl.

In some embodiments, R[4] is heterocyclyl optionally substituted with one to three substituents independently selected from the group consisting of —CN, halo, —O—R[12], —C(O)—R[12], —N(R[13])(R[14]), $C_{1-9}$ alkyl, $C_{1-8}$ haloalkyl, and heterocyclyl, or a pharmaceutically acceptable salt thereof.

In some embodiments, R[4] is

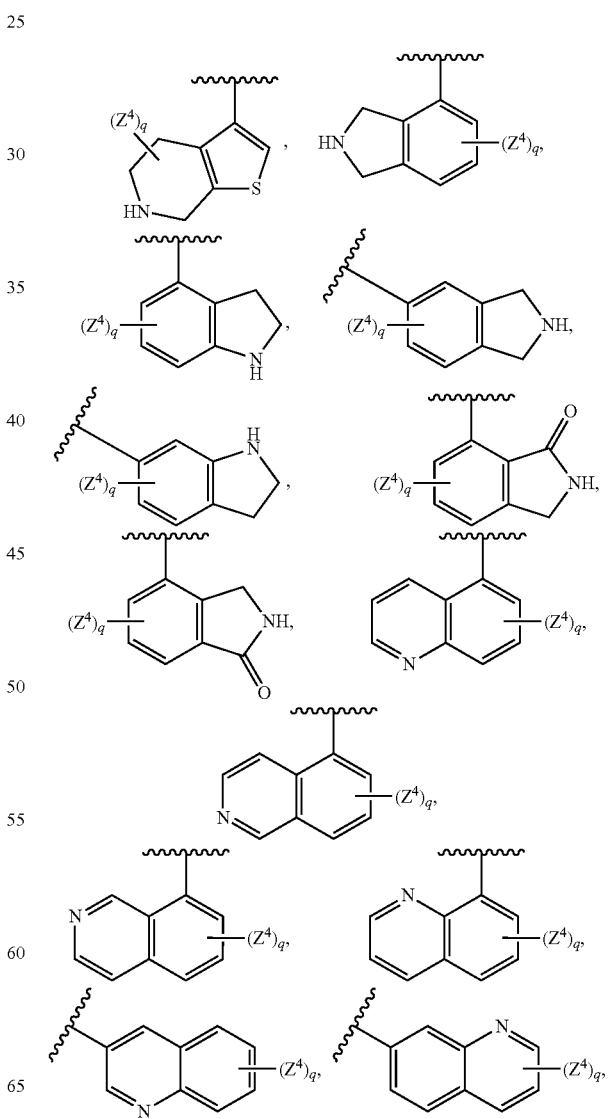

-continued

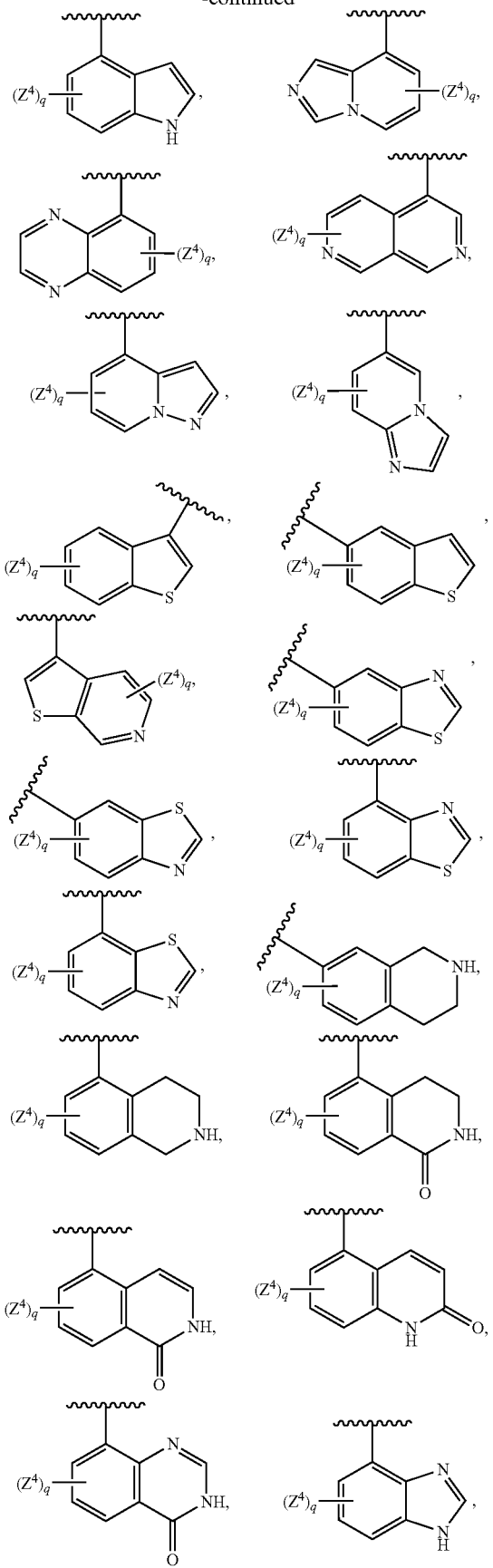

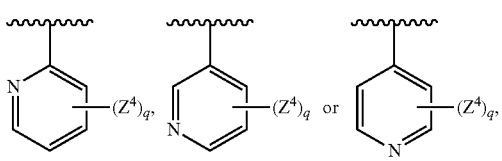

and q is 0, 1, 2, 3 or 4, and wherein $Z^4$ is independently selected from the group consisting of —CN, halo, —O—$R^{12}$, —C(O)—$R^{12}$, —N($R^{13}$)($R^{14}$), $C_{1-9}$ alkyl, $C_{1-8}$ haloalkyl, and heterocyclyl.

In some embodiments, $R^4$ is

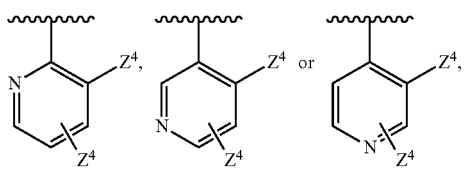

and q is 0, 1, 2, 3 or 4, and wherein $Z^4$ is independently selected from the group consisting of —CN, halo, —O—$R^{12}$, —C(O)—$R^{12}$, —N($R^{13}$)($R^{14}$), $C_{1-9}$ alkyl, $C_{1-8}$ haloalkyl, and heterocyclyl.

In some embodiments, $R^4$ is wherein $Z^4$ is independently selected from the group consisting of —CN, halo, —O—$R^{12}$, —C(O)—$R^{12}$, —N($R^{13}$)($R^{14}$), $C_{1-9}$ alkyl, $C_{1-8}$ haloalkyl, and heterocyclyl.

In certain embodiments, $R^4$ is

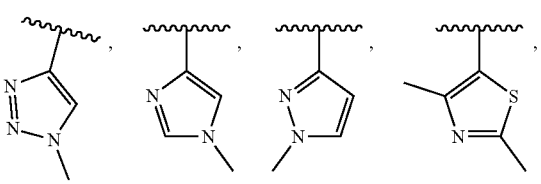

-continued
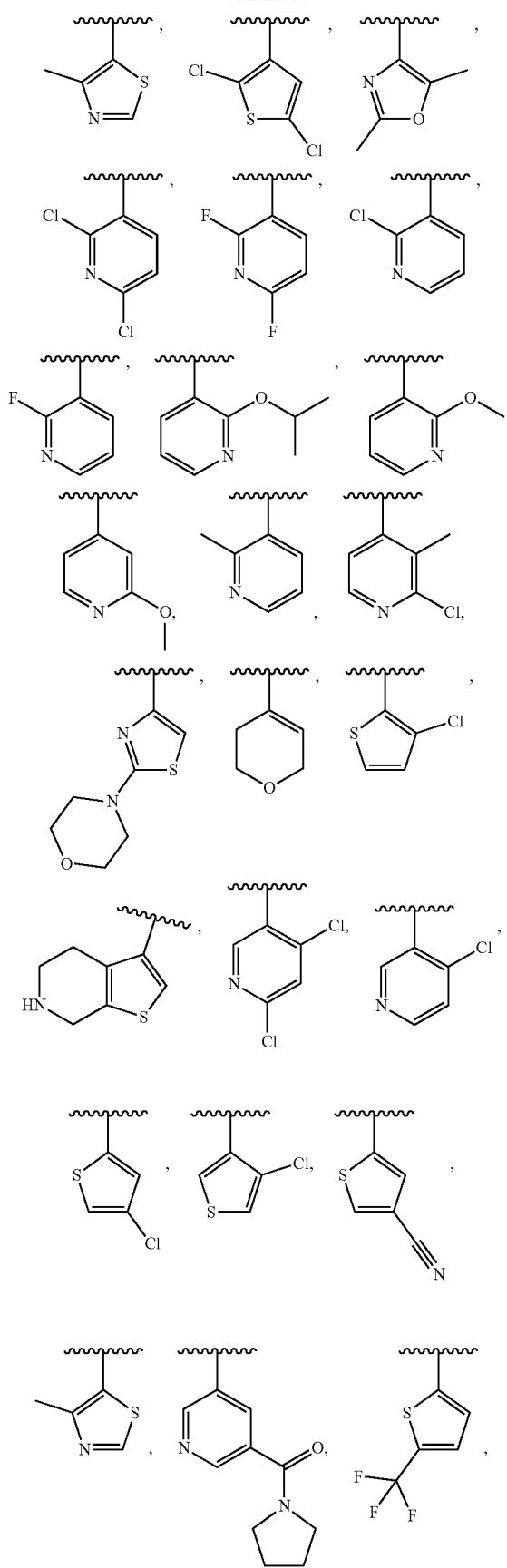
-continued
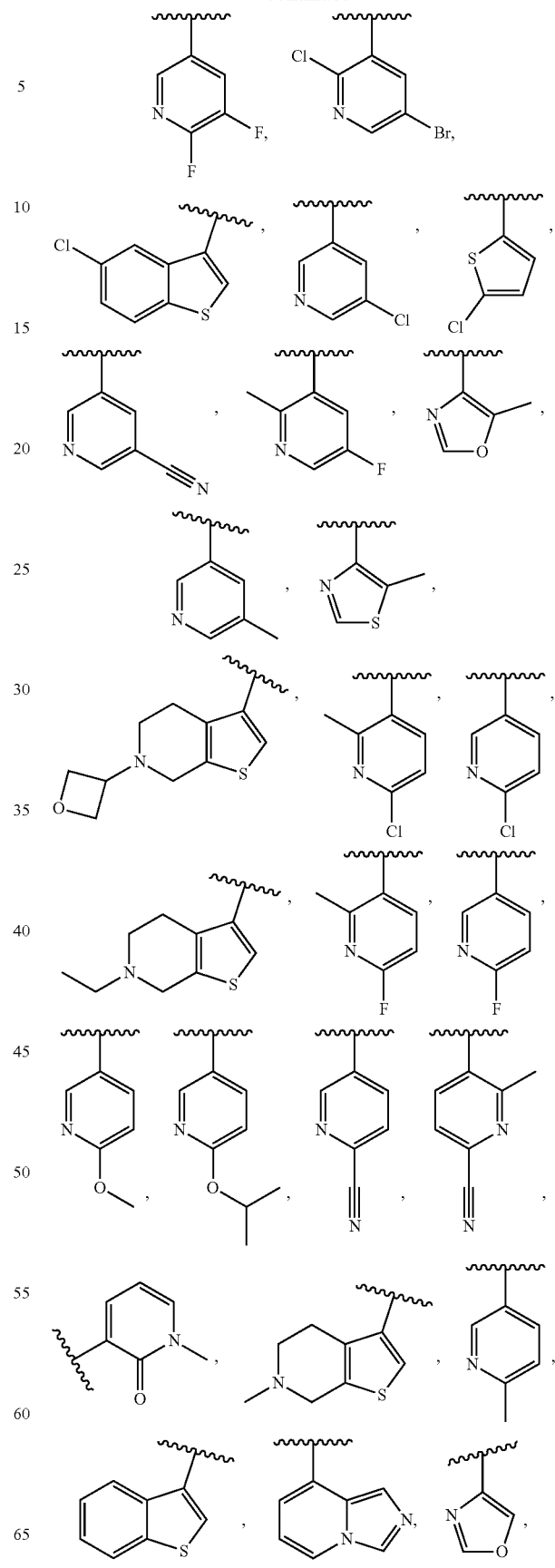

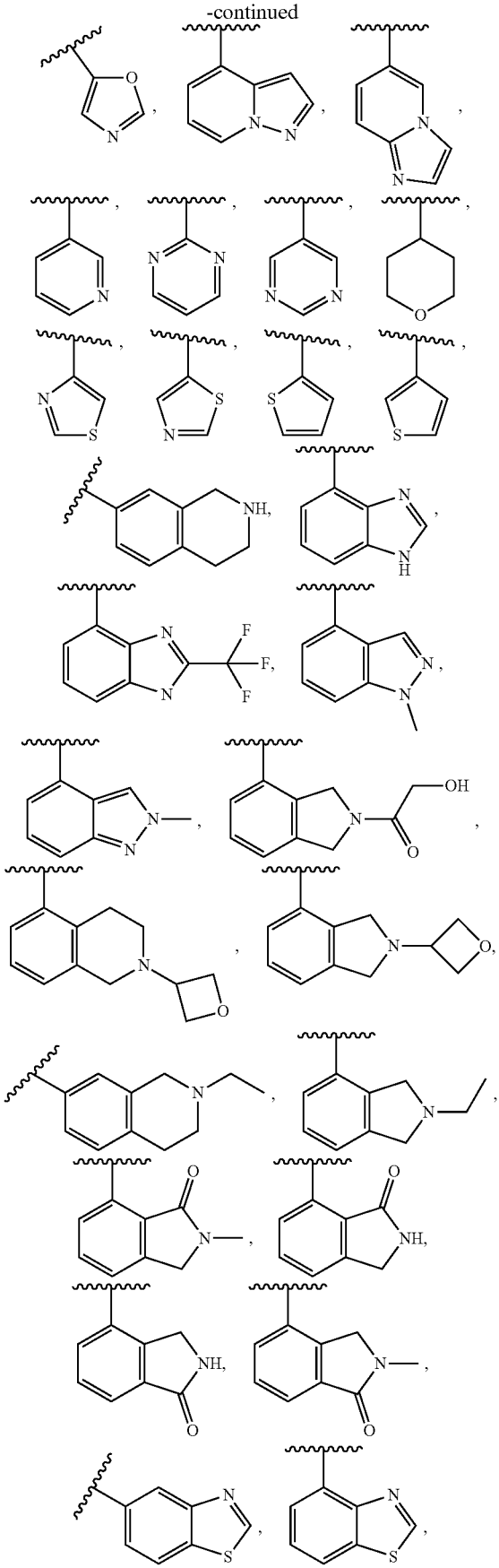
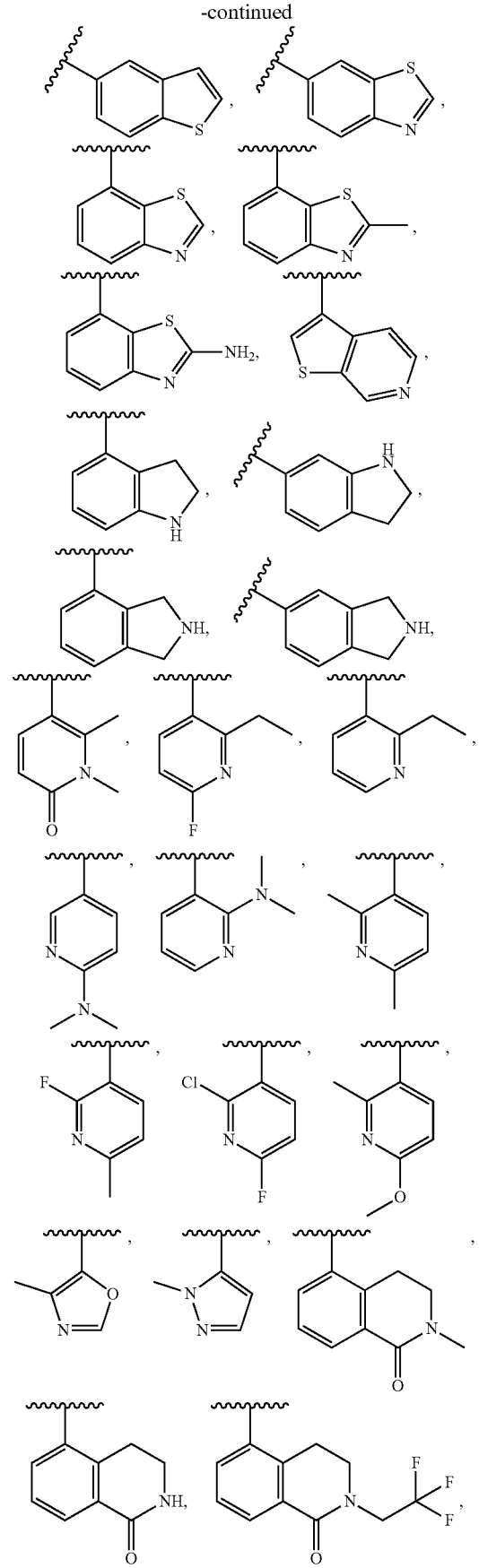

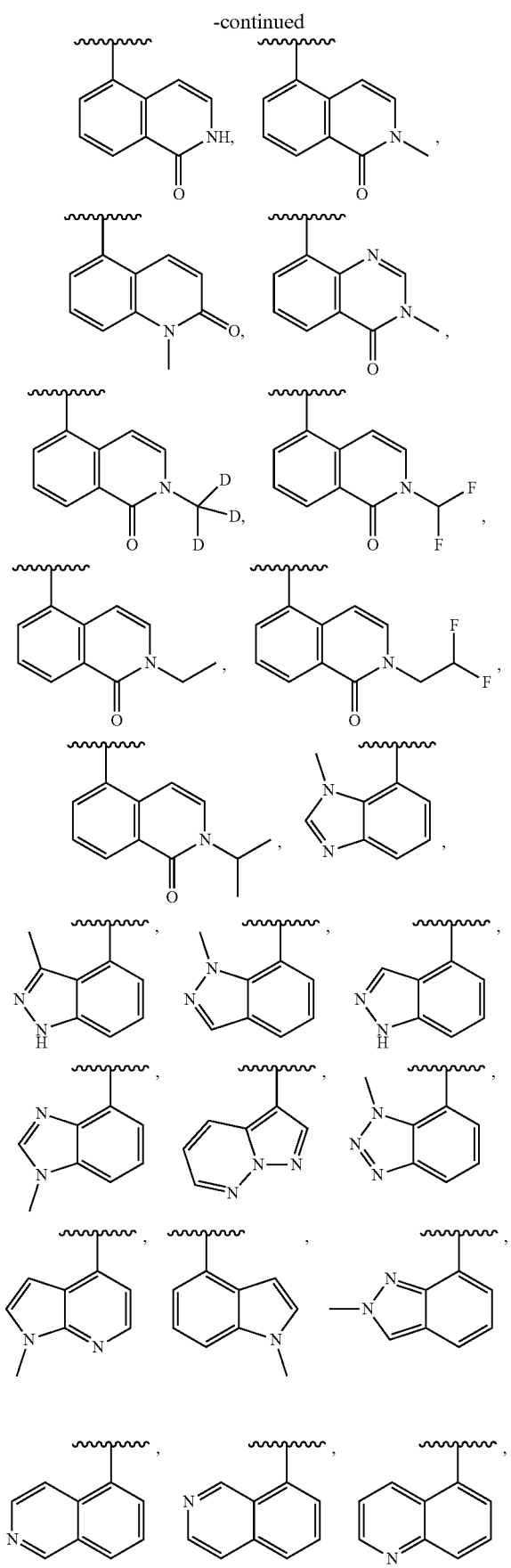
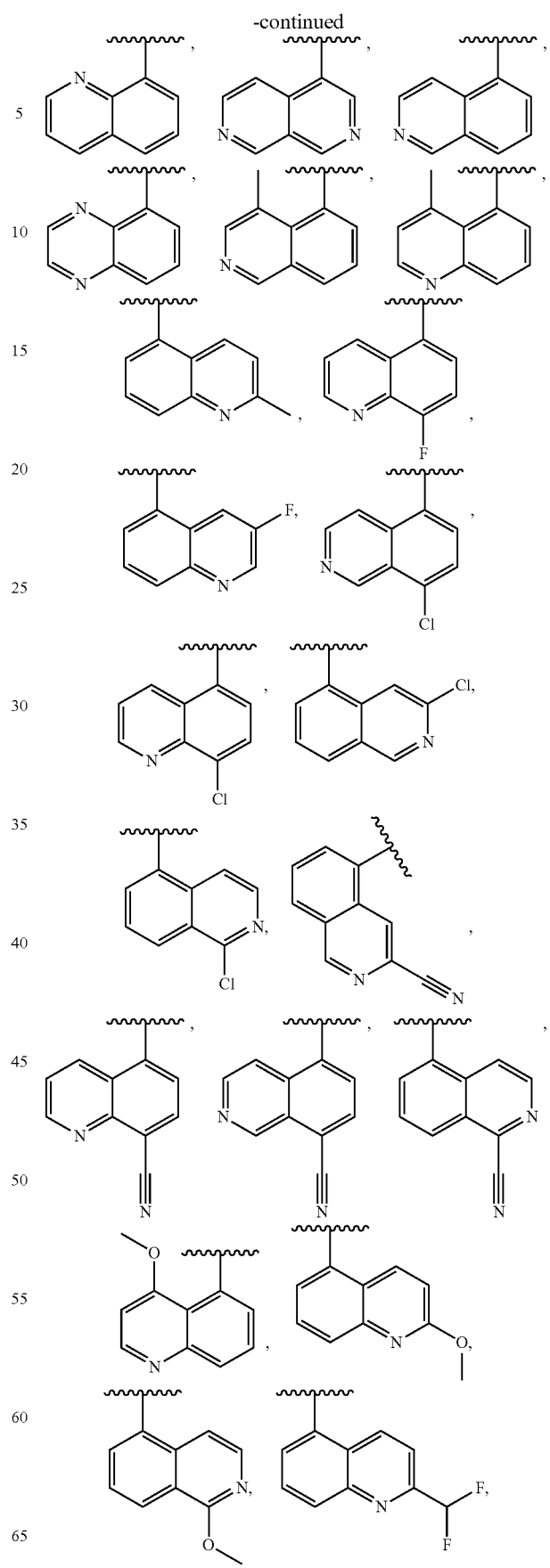

-continued

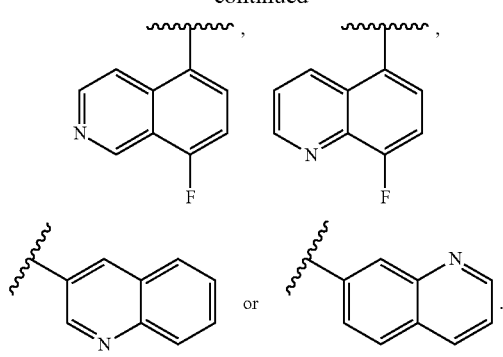

In certain embodiments, $R^5$ is hydrogen, halo, —CN, —O—$R^7$, —S(O)—$R^7$, —S(O)$_2R^7$, —S(O)$_2$N($R^7$)$_2$, —C(O)$R^7$, —C(O)N($R^7$)$_2$, $C_{1-9}$ alkyl, $C_{2-6}$ alkenyl, $C_{2-6}$ alkynyl, $C_{3-15}$ cycloalkyl, aryl, heterocyclyl, or heteroaryl; wherein each $C_{1-9}$ alkyl, $C_{2-6}$ alkenyl, $C_{2-6}$ alkynyl, $C_{3-15}$ cycloalkyl, aryl, heterocyclyl, and heteroaryl may be optionally substituted with one to four $Z^5$.

In certain embodiments, $R^5$ is hydrogen, halo, —CN, —C(O)$R^7$, or heteroaryl. In one embodiment, $R^5$ is —CN, halo or —O—$R^7$. In certain embodiments, $R^5$ is hydrogen, halo, —CN, —C(O)$R^7$, —O—$R^7$, —S(O)$_2R^7$ or heteroaryl. In one embodiment, $R^5$ is halo.

In certain embodiments, $R^5$ is 1H-pyrazol-4-yl, 1-hydroxyethyl, 1-methyl-1H-pyrazol-4-yl, 4-(acetylamino)phenyl, 6-fluoropyridin-3-yl, methyl acetyl, bromo, chloro, cyano, cyclopropyl, dimethylaminocarbonyl, ethynyl, fluoro, iodo, methoxy, methyl, hydroxyl, phenyl, pyridin-3-yl, pyridin-4-yl, pyrimidin-5-yl, acetyl, methylsulfonyl or trifluoromethyl. In one embodiment, $R^5$ is chloro.

In some embodiments, $R^6$ is —C(O)O—$R^{16}$—OP(O)(OH)$_2$.

In some embodiments, $R^6$ is

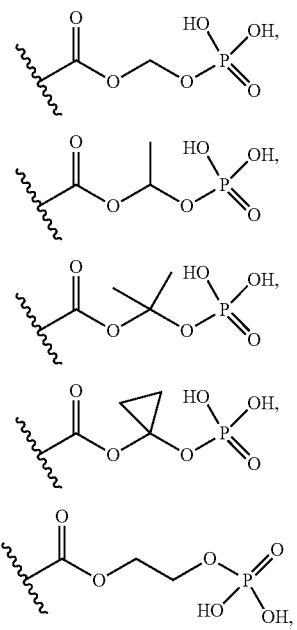

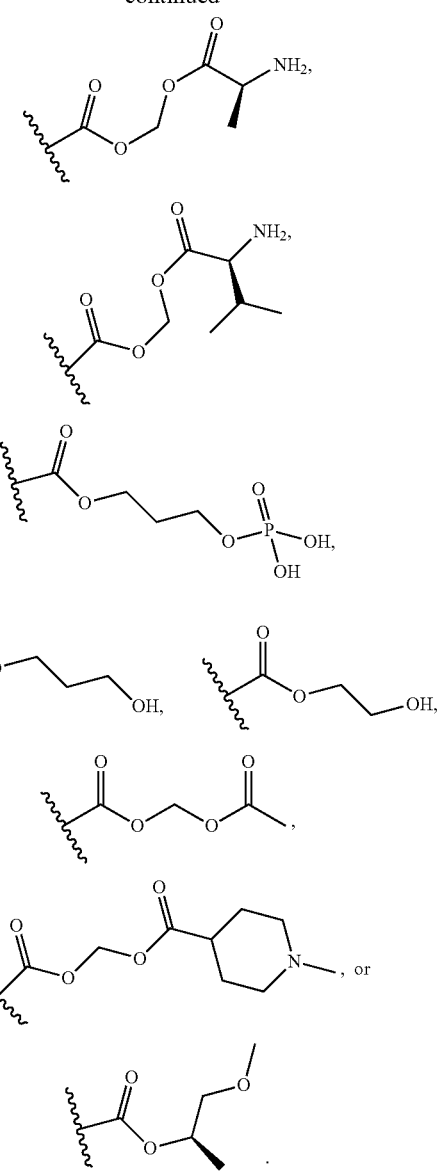

In some embodiments, $R^6$ is

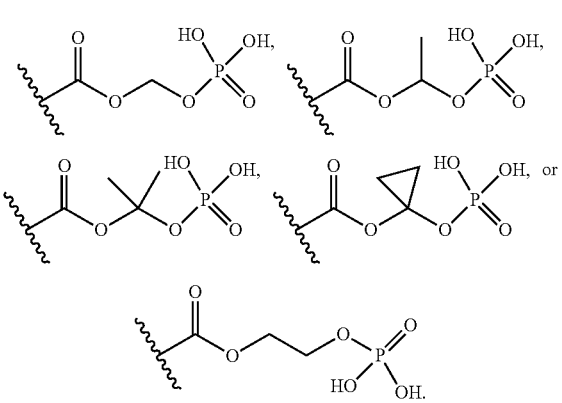

In some embodiments, $R^6$ is

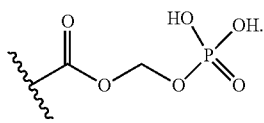 [SMILES: *C(=O)OCOP(=O)(O)O]

In some embodiments, $R^6$ is

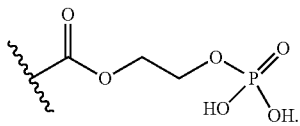 [SMILES: *C(=O)OCCOP(=O)(O)O]

In some embodiments, $R^{16}$ is $C_{2-3}$ alkyl. In some embodiments, $R^{16}$ is methyl. In some embodiments, $R^{16}$ is ethyl. In some embodiments, $R^{16}$ is unsubstituted. In some embodiments, $R^{16}$ is substituted by one, two, three, or four methyl groups. In some embodiments, $R^{16}$ is substituted by one or two methyl groups. In some embodiments, $R^{16}$ is substituted by one or two cyclopropyl groups.

In some embodiments, $Z^9$ is hydrogen.

Some embodiments provide a compound of formula:

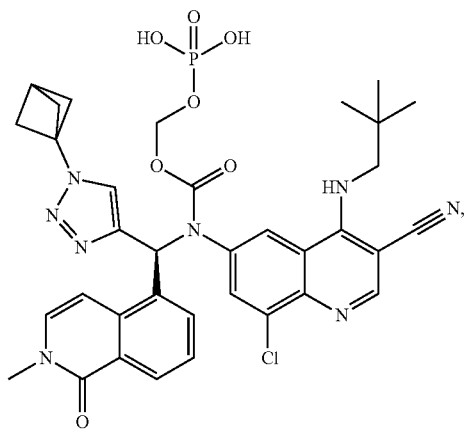

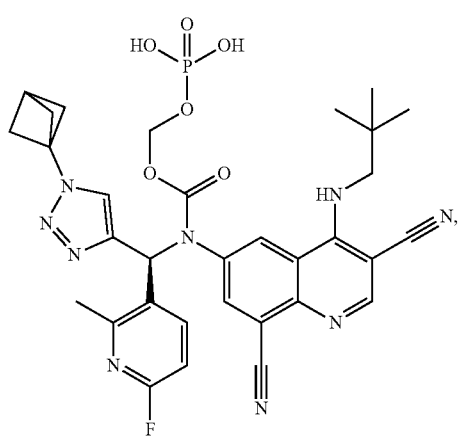

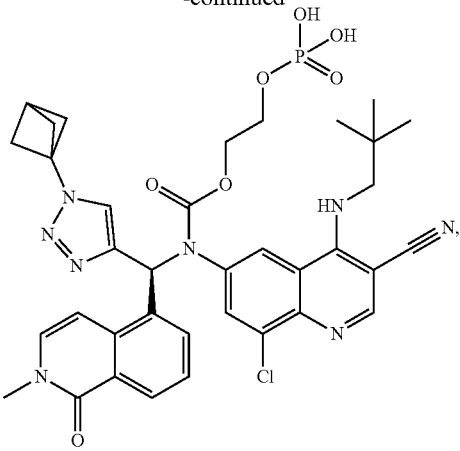

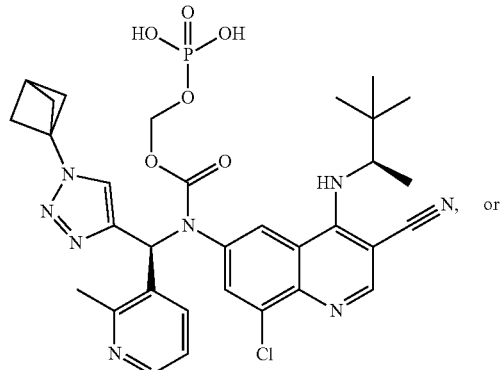

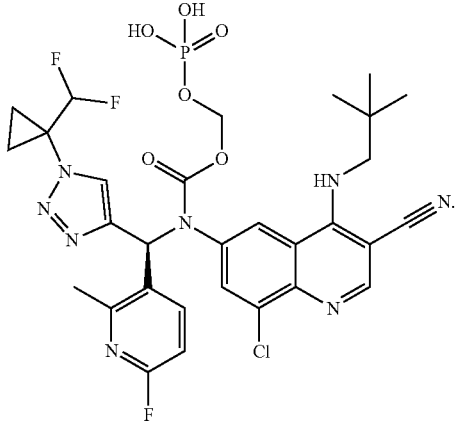

In one embodiment, is 0. In another embodiment, in is 1.

Some embodiments of the disclosure include compounds of the following Formula III:

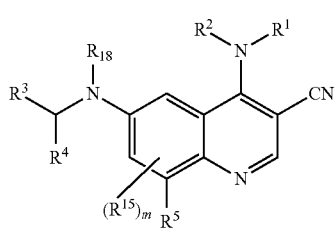

III wherein

R¹, R², R³, R⁴, R⁵, R¹⁵, and m are as described herein, and R¹⁸ is hydrogen, —C(O)—R⁷, —C(O)O—R⁷, —C(O)N(R⁷)₂, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

or a pharmaceutically acceptable salt, tautomer, stereoisomer, mixture of stereoisomers, prodrug, or deuterated analog thereof.

In general, the specific compounds exemplified herein are named using ChemBioDraw Ultra. However, it is understood that other names may be used to identify compounds of the same structure. For example, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein can include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

A composition comprising a mixture of enantiomers (or diastereomers) of a compound described herein or a pharmaceutically acceptable salt thereof, is also provided herein. In some embodiments, the composition comprises a single enantiomer of the compound and is substantially free of the other enantiomer. In certain embodiments, the compound of Formula I (or another Formula as described herein) contains one or more additional stereogenic atom(s) (e.g., at R¹ and/or R³). In such instances, the composition may contain a mixture of diastereomers. In some embodiments, the composition comprises a single enantiomer of the compound and is substantially free (i.e., having less than or about 40%, 30%, 25%, 20%, 15%, 10%, 5%, 1%, 0.05%, or 0.01%) of one or more diastereomers.

Accordingly, in certain embodiments, provided is a composition comprising a mixture of Formula IA-1, or a pharmaceutically acceptable salt thereof, and Formula IB-1, or a pharmaceutically acceptable salt thereof.

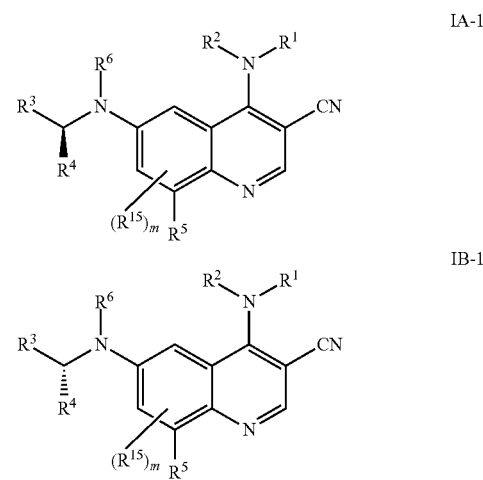

wherein m, R¹, R², R³, R⁴, R⁵, R⁶ and R¹⁵ are as defined herein.

In one embodiment, the mixture is a racemic mixture. In other embodiments, the composition comprises a mixture of Formula IA-1, or a pharmaceutically acceptable salt thereof, and Formula IB-1, or a pharmaceutically acceptable salt thereof, wherein Formula IA-1 is present in excess of over Formula IB-1, or a pharmaceutically acceptable salt thereof. In certain embodiments, provided is a composition substantially free of Formula IB-1, having less than or about 40%, 30%, 25%, 20%, 15%, 10%, 5%, 1%, 0.05%, or 0.01% of compounds of Formula IB-1.

In other embodiments, the mixture comprises compounds of Formula IA-1 and IB-1 in a a molar ratio of at least or about 3:1, at least or about 4:1, at least or about 5:1, at least or about 6:1, at least or about 7:1, at least or about 8:1, at least or about 9:1, at least or about 10:1, at least or about 11:1, at least or about 12:1, at least or about 20:1, at least or about 30:1, at least or about 40:1, at least or about 80:1, at least or about 160:1, or at least or about 320:1, respectively.

In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Cot" or variants thereof refers to a decrease in activity in Cot as a direct or indirect response to the presence of a compound of the present application relative to the activity Cot in the absence of the compound of the present application. "Inhibition of Cot" refers to a decrease in Cot activity as a direct or indirect response to the presence of a compound described herein relative to the activity of Cot in the absence of the compound described herein. In some embodiments, the inhibition of Cot activity may be compared in the same subject prior to treatment, or other subjects not receiving the treatment.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds and compositions described herein may be used for a variety of purposes, including therapeutic and experimental purposes. For example, the compounds and compositions described herein may be used ex vivo to determine the optimal schedule and/or dosing of administration of a Cot inhibitor for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds disclosed herein are useful for the treatment of diseases or conditions mediated by Cot. Non-limiting examples of diseases or conditions mediated by Cot include, without limitation, cancer, diabetes, and inflammatory diseases such as rheumatoid arthritis (RA), multiple sclerosis (MS), inflammatory bowel disease (IBD), sepsis, psoriasis, misregulated TNF expression, graft rejection, and liver disease.

In further embodiments, the methods are provided for alleviating a symptom of a disease or disorder mediated by Cot. In some embodiments, the methods include identifying a mammal having a symptom of a disease or disorder mediated by Cot, and providing to the mammal an amount of a compound as described herein effective to ameliorate (i.e., lessen the severity of) the symptom.

In some embodiments, the disease or condition mediated by Cot is cancer. In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided can be used to treat cancer at various stages. By way of example, the cancer stage includes but is not limited to early, advanced, locally advanced, remission, refractory, reoccurred after remission and progressive.

In some embodiments, the disease or condition mediated by Cot is diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by Cot is an inflammatory disease or LPS induced endotoxin shock. In some embodiments, the disease is an autoimmune disease.

In some embodiments, the inflammatory disease is acid-induced lung injury, Addison's disease, adrenal hyperplasia, adrenocortical insufficiency, adult-onset Still's disease, adult respiratory distress syndrome (ARDS), age-related macular degeneration, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinurla), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, Bacillus anthracis infection, Bechet's disease, bee sting-induced inflammation, Behcet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cyrptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, preperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), spinal cord injury, spinal stenosis, spondyloarthropathies, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, or Whipple disease.

In some embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated by Cot is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behget's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD can vary and can be associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic mueloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lynphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048. Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition. Tp12 can mediate immune related liver diseases or conditions. (Vyrla et. al., The Journal of Immunology, 2016, 196; Perugorria et. al., Hepatology, 2013; 57:1238-1249).

In some embodiments, the disease or condition mediated by Cot is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g. prednisolone) and phosophodiesterase inhibitors (e.g. pentoxifylline) can be used to treat alcoholic hepatitis. The compounds herein can be used as stand-alone treatments or in combination with the current treatments for alcoholic hepatitis.

In some embodiments, the disease or condition mediated by Cot is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

In some embodiments, the disease or condition mediated by Cot is acute or chronic liver failure, acute intrahepatic cholestatic conditions, of obstructive or chronic inflammatory disorders that arise out of improper bile composition, alcohol-induced cirrhosis and associated cholestasis, a cholestatic or fibrotic effect that is associated with alcohol-induced cirrhosis or with a viral-borne form of hepatitis, chemotherapy associated steatohepatitis (CASH), chronic intrahepatic or extrahepatic cholestatic condition, a chronic or obstructive inflammatory disorder of the liver, congenital hepatic fibrosis, a lipid disorder or lipoprotein disorder, liver fibrosis, liver cirrhosis, liver failure or liver ischemia after major liver resection, liver steatosis or an associated syndrome, liver ischemia after major liver resection, a neoplastic disease of the gastrointestinal tract or liver, Non-Alcoholic Fatty Liver Disease (NAFLD), Non-Alcoholic Steatohepatitis (NASH), obstructive or chronic inflammatory disorders of the liver, obesity, Primary Biliary Cirrhosis (PBC), Primary Sclerosing Cholangitis (PSC), progressive familiar cholestatsis, or a metabolic syndrome selected from the group consisting of combined conditions of dyslipidemia, diabetes and abnormally high body-mass index.

In some embodiments, the disease or condition mediated by Cot is diabetic kidney disease (DKD).

Improvements in any of the foregoing response criteria are specifically provided by the methods of the present disclosure.

Combination Therapies

In one embodiment, the compounds disclosed herein may be used in combination with one or more additional therapeutic agents.

In some embodiments, the additional therapeutic agent(s) are being used and/or developed to treat inflammatory disorders (e.g., IBD). The one or more additional therapeutic agents may be Beta adrenoceptor antagonists, Beta-glucuronidase inhibitors, Bradykinin receptor modulators, Calcineurin inhibitors, Calcium channel inhibitors, Cathepsin S inhibitors, CCR3 chemokine antagonists, CD40 ligand receptor antagonists, Chemokine CXC ligand inhibitors, CHST15 gene inhibitors, Collagen modulators, CSF-1 antagonists, Cyclooxygenase inhibitors, Cytochrome P450 3A4 inhibitors, Eotaxin ligand inhibitors, EP4 prostanoid receptor agonists, Fractalkine ligand inhibitors, Free fatty acid receptor 2 antagonists, GATA 3 transcription factor inhibitors, Glucagon-like peptide 2 agonists, Glucocorticoid agonists, Guanylate cyclase receptor agonists, Histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, Integrin alpha-4/beta-1 antagonists, Integrin alpha-4/beta-7 antagonists, Integrin alpha-E antagonists, Integrin antagonists, Integrin beta-7 antagonists, Interleukin ligand inhibitors, Interleukin receptor 17A antagonists, Interleukin-1 beta ligands, Interleukin-1 beta ligand modulators, JAK tyrosine kinase inhibitors, Jak1 tyrosine kinase inhibitors, Jak3 tyrosine kinase inhibitors, LanC like protein 2 modulators, Lipoxygenase modulators, MAdCAM inhibitors, Matrix metalloprotease inhibitors, Melanocortin agonists, Metalloprotease-9 inhibitors, Natriuretic peptide receptor C agonists, Neuregulin-4 ligands, NKG2 D activating NK receptor antagonists, Opioid receptor antagonists, Opioid receptor delta antagonists, Oxidoreductase inhibitors, P2X7 purinoceptor agonists, PDE 4 inhibitors, Phagocytosis stimulating peptide modulators, Potassium channel inhibitors, PPAR alpha agonists, PPAR delta agonists, PPAR gamma agonists, Protein fimH inhibitors, P-selectin glycoprotein ligand-1 inhibitors, RNA polymerase inhibitors, Sphingosine 1 phosphate phosphatase 1 stimulators, Sphingosine 1 phosphate phosphatase modulators, Sphingosine-1-phosphate receptor-1 agonists, Sphingosine-1-phosphate receptor-1 antagonists, Sphingosine-1-phosphate receptor-1 modulators, Sphingosine-1-phosphate receptor-5 modulators, STAT3 gene inhibitors, Stem cell antigen-1 inhibitors, Superoxide dismutase modulators, Superoxide dismutase stimulators, TGF beta 1 ligand inhibitors, thymulin agonists, TLR antagonists, TLR agonists, TNF alpha ligand inhibitors, TNF antagonists, Tumor necrosis factor 14 ligand modulators, Type II TNF receptor modulators, Zonulin inhibitors.

Exemplary additional therapeutic agents include ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184 budesonide; CEQ-508; certolizumab; Clostridium butyricum; ChAdOx2-HAV, dexamethasone sodium phosphate, DNVX-078, etanercept; ETX-201, golimumab; infliximab; mesalazine, HLD-400, LYC-30937 EC; IONIS-JBI1-2.5Rx, JNJ-64304500, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; E-6011; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; RHB-104; rifaximin; tildrakizumab; tralokinumab; brodalumab; laquinimod; plecanatide; or AZD-058.

In some embodiments, the additional thereapeutic agent(s) includes one or more Alpha-fetoprotein modulator, such as ACT-101; Beta adrenoceptor antagonists, such as NM-001; Calcineurin inhibitors, such as tacrolimus; Carbohydrate metabolism modulators, such as ASD-003; Cathepsin S inhibitors, such as VBY-129; CD40 ligand receptor antagonists, such as FFP-104, BI-655064; Chemokine CXC ligand inhibitors, such as LY-3041658; CHST15 gene inhibitors, such as STNM-01; Collagen modulators, such as ECCS-50 (DCCT-10); CSF-1 antagonists, such as JNJ-40346527 (PRV-6527); CX3CR1 chemokine modulator, such as E-6130; Ecobiotic, such as SER-287; Eotaxin ligand inhibitors, such as bertilimumab; EP4 prostanoid receptor agonists, such as KAG-308; FIFO ATP synthase modulator, such as LYC-30937 EC; Fractalkine ligand inhibitors, such as E-6011; Free fatty acid receptor 2 antagonists, such as GLPG-0974; GATA 3 transcription factor inhibitors, such as SB-012; Glucagon-like peptide 2 agonists, such as teduglutide; Glucocorticoid agonists, such as budesonide, beclomethasone dipropionate, dexamethasone sodium phosphate; Guanylate cyclase receptor agonists, such as dolcanatide; HIF prolyl hydroxylase inhibitor, such as DS-1093, AKB-4924; Histone deacetylase inhibitors, such as givinostat; HLA class II antigen modulators, such as HLA class II protein modulators; IL-12 antagonists, such as ustekinumab (IL12/IL23); IL-13 antagonists, such as tralokinumab; IL-22 agonists, such as RG-7880; IL-23 antagonists, such as tildrakizumab, risankizumab (BI-655066), mirikizumab (LY-3074828), brazikumab (AMG-139), PGT-200; IL-6 antagonists, such as olokizumab; IL-8 receptor antagonists, such as clotrimazole; Integrin alpha-4/beta-1 antagonists, such as natalizumab; Integrin alpha-4/beta-7 antagonists, such as etrolizumab (α4β7/αEβ7), vedolizumab, carotegast methyl, TRK-170 (α4β7/α4β1), PTG-100; Integrin antagonists, such as E-6007; Interleukin ligand inhibitors, such as bimekizumab (IL-17A/IL-17E); Interleukin receptor 17A antagonists, such as brodalumab; Interleukin-1 beta ligands, such as K(D)PT; Interleukin 1 like receptor 2 inhibitor, such as BI-655130; IL-6 receptor modulator, such as olamkicept; JAK tyrosine kinase inhibitors, such as tofacitinib (1/3), peficitinib (1/3), TD-3504, TD-1473; Jak1 tyrosine kinase inhibitors, such as upadacitinib (ABT-494), filgotinib, GLPG-0555, PF-06700841 (JAK1/Tyk2); Jak3 tyrosine kinase inhibitors, such as PF-06651600; LanC like protein 2 modulators, such as BT-11; MAdCAM inhibitors, such as SHP-647 (PF-547659); melanin concentrating hormone (MCH-1) antagonist, such as CSTI-100; Melanocortin agonists, such as ASP-3291, PL-8177; Metalloprotease-9 inhibitors, such as GS-5745; Natriuretic peptide receptor C agonists, such as plecanatide; Neuregulin-4 ligands, such as NRG-4; NKG2 D activating NK receptor antagonists, such as JNJ-4500; Opioid receptor antagonists, such as naltrexone, IRT-103; OX40 ligand inhibitor, such as KHK-4083; Oxidoreductase inhibitors, such as olsalazine; P2X7 purinoceptor modulator, such as SGM-1019; PDE 4 inhibitors, such as apremilast; PPAR alpha/delta agonists, such as elafibranor (GFT-1007); PPAR gamma agonists, such as GED-0507-34-Levo; Protein fimH inhibitors, such as EB-8018; P-selectin glycoprotein ligand-1 inhibitors, such as SEL-K2, neihulizumab; Ret tyrosine kinase receptor inhibitor, such as GSK-3179106; RIP-1 kinase inhibitor, such as GSK-2982772; RIP-2 kinase inhibitor, such as GSK-2983559; Sphingosine 1 phosphate phosphatase 1 stimulators, such as etrasimod; Sphingosine-1-phosphate receptor-1 agonists, such as ozanimod, mocravimod (KRP-203), BMS-986166; Sphingosine-1-phosphate receptor-1 antagonists, such as amiselimod (MT-1303); Stem cell antigen-1 inhibitors, such as Ampion (DMI-9523); Superoxide dismutase modulators, such as midismase; TLR-4 antagonists, such as JKB-122; TLR-9 agonists, such as cobitolimod; TNF alpha ligand inhibitors, such as adalimumab, certolizumab, infliximab, golimumab, DLX-105, Debio-0512, HMPL-004, CYT-020-TNFQb, V-565; TNF antagonists, such as AVX-470, tulinercept, etanercept; TPL-2 inhibitor, such as GS-4875; Tumor necrosis factor 14 ligand modulators, such as AEVI-002; Tumor necrosis factor 15 ligand inhibitor, such as PF-06480605; Type I IL-1 receptor antagonist, such as anakinra; and/or Zonulin inhibitors, such as larazotide acetate.

In some embodiments, the one or more additional therapeutic agent may be a α4β7 integrin inhibitor, or an agent that inhibits the expression and/or activity of α4β7 integrin. The inhibitor can be small molecule or biologic. For example, the α4β7 integrin inhibitor can be natalizumab or vedolizumab.

In some embodiments, the one or more additional therapeutic agent may be a steroid, including but not limited to, corticosteroids. Corticosteroids may be administered by various routes, including intravenously (i.e., methylprednisolone, hydrocortisone), orally (i.e., prednisone, prednisolone, budesonide, dexamethasone), or topically (i.e., enema, suppository, or foam preparations).

In some embodiments, the one or more additional therapeutic agent may be an MMP9 inhibitor, or an agent that inhibits the expression and/or activity of MMP9. A representative protein sequence for MMP9 is GenBank Accession No. NP 004985. The inhibitor can be small molecule or biologic. For instance, Gu et al., *The Journal of Neuroscience*, 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

In some embodiments, the one or more additional therapeutic agent may be a Sphingosine 1-Phosphate Receptor (S1P1) inhibitor, or an agent that inhibits the expression and/or activity of S1P1. The inhibitor can be small molecule or biologic. For example, the S1P1 inhibitor can be RPC1063.

In some embodiments, the one or more additional therapeutic agent may be a TNF inhibitor, or an agent that inhibits the expression and/or activity of TNF. The inhibitor can be small molecule or biologic. For example, the TNF inhibitor can be golimumab.

In some embodiments, the one or more additional therapeutic agent is being used and/or developed to treat ulcerative colitis (UC) and/or Crohn disease (CD). The agent can be a biologic or small molecule. In some embodiments, the agent is a modulator (e.g., agonist or antagonist) of alpha-fetoprotein, beta adrenoceptor, calcineurin, carbohydrate metabolism, cathepsin S, S1P1, IL-6, CX3CL1, DHODH, α4, β7, JAK, TNF, CB, IL-12/IL-23, CCL20, TLR9, MAdCAM, CCR9, CXCL10, Smad7, PDE4, MC, VLA-1, GC, GATA-3, Eotaxin, FFA2, LIGHT, FMS, MMP9, CD40, Steroid, 5-ASA, Immunomod, STATS, and/or EP4.

In some embodiments the additional thereapeutic agent(s) are being used and/or developed to treat IBD. Non-limiting examples of agents being used and/or developed to treat IBD include ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; 131-655130, BMS-986184; budesonide; CEQ-508; certolizumab; Clostridium butyricum; ChAdOx2-HAV, dexamethasone sodium phosphate, DNVX-078, etanercept; ETX-201, golimumab; infliximab; mesalazine, HLD-400, LYC-30937 EC; IONIS-JBI1-2.5Rx, JNJ-64304500, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; E-6011; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; RHB-104; rifaximin; tildrakizumab; tralokinumab; brodalumab; laquinimod; plecanatide; and AZD-058.

Non-limiting examples of agents being used and/or developed to treat ulcerative colitis (UC) and Crohn disease (CD) include PF-06410293 (by Pfizer), SAN-300 (VLA-1 modulator, by Salix), SAR252067 (LIGHT modualtor, by Sanofi), PF-00547659 (MAdCAM modualtor, by Pfizer), Eldelumab (Smad7 modulator, by BMS), AMG 181/MEDI-7183 ((37 modulator, by Amgen/Astra7eneca), Etrolizumab (β7 modulator, by Roche), Ustekinumab (IL-12/IL-23 modulator, by J&J), Remicade (TNF modulator, by J&J and Merck), Entyvio (β7 modulator, by Takeda), Humira (TNF modulator, by Abbvie), Infliximab (by Celtrion), PF-06651600 (by Pfizer), GSK2982772 (by GSK), GLPG1205 (FFA2 modulator, by Galapagos), AG014 (by Intrexon) and Vidofludimus (DHODH modulator, by 4SC).

In some embodiments, the one or more additional therapeutic agent may be a JAK inhibitor, such as a JAK-1 selective inhibitor. The inhibitor can be small molecule or biologic. For example, the JAK inhibitor can be Filgotinib, GLPG0634 (JAK modulator, by Galapagos).

In some embodiments, the one or more additional therapeutic agents is/are a(n) ACE inhibitor, Acetaldehyde dehydrogenase inhibitor, Acetyl CoA carboxylase inhibitor, Acetyl CoA carboxylase inhibitor, Diacylglycerol O acyltransferase 2 inhibitor, Adenosine A3 receptor agonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Androgen receptor agonist, Amylin receptor agonist, Angiotensin II AT-1 receptor antagonist, Autophagy protein modulator, Autotaxin inhibitors, Axl tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor, Caveolin 1 inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, Chloride channel stimulator, CNR1 inhibitor, Cyclin D1 inhibitor, Cytochrome P450 7A1 inhibitor, DGAT1/2 inhibitor, Diacylglycerol O acyltransferase 1 inhibitor (DGAT1), Cytochrome P450 2E1 inhibitor (CYP2E1), CXCR4 chemokine antagonist, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, Hypoxia inducible factor-2 alpha inhibitor, IL-10 agonist, IL-17 antagonist, Ileal sodium bile acid cotransporter inhibitor, Insulin sensitizer, Insulin ligand agonist, Insulin receptor agonist, integrin modulator, Integrin Antagonist, intereukin-1 receptor-associated kinase 4 (IRAK4) inhibitor, IL-6 receptor agonist, Jak2 tyrosine kinase inhibitor, Ketohexokinase (KHK) inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-21(miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, Nuclear receptor modulators, P2X7 purinoceptor modulator, PDE 3 inhibitor, PDE 4 inhibitor, PDE 5 inhibitor, PDGF receptor beta modulator, Phenylalanine hydroxylase stimulator, Phospholipase C inhibitor, PPAR alpha agonist, PPAR delta agonist, PPAR gamma agonist, Peptidyl-prolyl cis-trans isomerase A inhibitor, PPAR gamma modulator, Protease-activated receptor-2 antagonist, Protein kinase modulator, Rho associated protein kinase inhibitor, Snitrosoglutathione reductase (GSNOR) enzyme inhibitor, Sodium glucose transporter-2 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator and Zonulin inhibitor.

For example, the additional therapeutic agent(s) may include A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201, NGM-282, NGM-313, NGM-386, NGM-395, NP-160, norursodeoxycholic acid, NVP-022, O-304, obeticholic acid, 25HC3S, olesoxime, PAT-505, PAT-048, PB-4547, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XRx-117, ZGN-839, ZG-5216, ZSYM-008, ZYSM-007.

Kits

Provided herein are also kits that include a compound described herein, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of Formula I (or any other Formula described herein), or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any given subject will depend upon a variety of factors including the activity of the specific compound employed, the age, body weight, general health, sex, diet, time of administration, route of administration, and rate of excretion, drug combination and the severity of the given disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight can be useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day. In some embodiments, a compound a daily dosage of a compound of Formula I, or another formula described herein, is between about 150 mg/day and 1000 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy and are frequently alternated with resting periods of about 1 to 28 days, commonly about 7 days or about 14 days, between cycles. The treatment cycles, in other embodiments, may also be continuous.

In some embodiments, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of Compounds

Compounds disclosed herein may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

Genera/Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the specified reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents are inert organic solvents, and the reactions may carried out under an inert gas, preferably argon or nitrogen.

The term "q.s." means adding a quantity sufficient to achieve a stated function, e.g., to bring a solution to the desired volume (i.e., 100%).

Compounds of Formula I can be prepared by first providing a substituted quinoline core, and optionally further modifying the core as desired to provide the substituents disclosed herein. Scheme 1 shows the preparation of a quinoline core to provide compounds of Formula 1-e, where m, $R^5$ and $R^{15}$ are as defined herein, or are a functional group that can be converted thereto using standard reaction conditions.

Scheme 1

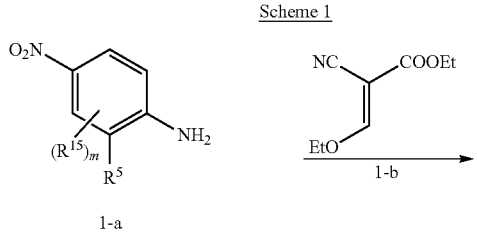

1-a    1-b

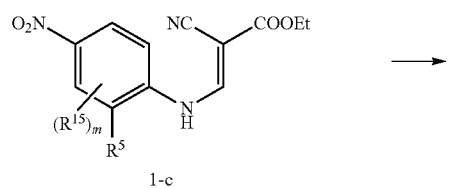

1-c

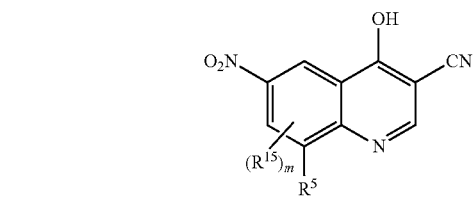

1-d

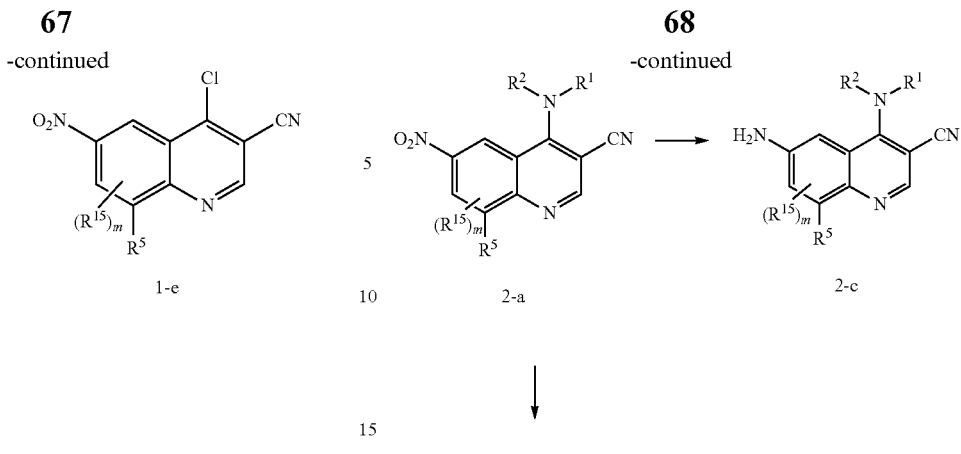

In Scheme 1, suitably substituted 1-a and 1-b are condensed in a suitable solvent (e.g., DMF, etc.) in the presence of catalyst (e.g., $Cs_2CO_3$, etc.) at an elevated temperature (e.g., about 40-50° C.) to provide 1-c. Compound 1-c is then converted to 1-d under thermal cyclization conditions (i.e., about 250° C.) or under microwave conditions. Chlorination of 1-d to provide 1-e is achieved using a suitable chlorinating agent (e.g., $POCl_3$, $SOCl_2$, etc.) at an elevated temperature (e.g., about 110-120° C.) in the presence of a base (e.g. pyridine, dimethylaniline, diethylaniline, etc.) or a catalyst (e.g., DMF, DEF, etc.) and in a suitable solvent (e.g. chlorobenzene, $CH_3CN$, etc.) or solvent-free conditions (i.e., neat).

Scheme 2 shows a synthesis of compounds of Formula 2-c and 2-d where m, $R^1$, $R^2$, $R^5$ and $R^{15}$ are as defined herein.

Scheme 2

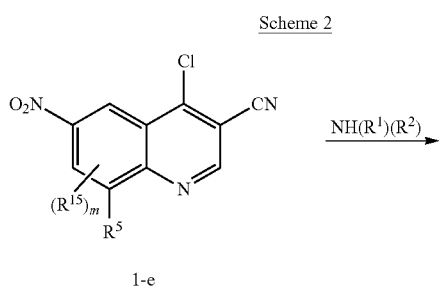

In Scheme 2, 1-e is reacted with a suitable amine under standard nucleophilic aromatic substitution conditions in the presence of a base (e.g., $NEt_3$, etc.) and at elevated temperature (e.g., 150° C.) to obtain 2-a. Compounds of Formula I where $R^5$ and/or $R^{15}$ is cyano are provided by reacting 2-a with a suitable cyanating agent (e.g., CuCN, $Zn(CN)_2$, etc.) in the presence of a catalyst (e.g., palladium, nickel, copper, etc.). Compounds 2-c and 2-d are then provided via reduction of the nitro group of compounds 2-a or 2-b, respectively (using e.g., Fe, $SnCl_2$, etc.).

Scheme 3 shows the synthesis of compounds 3-d and 3-e, where $R^4$ is as defined herein.

Scheme 3

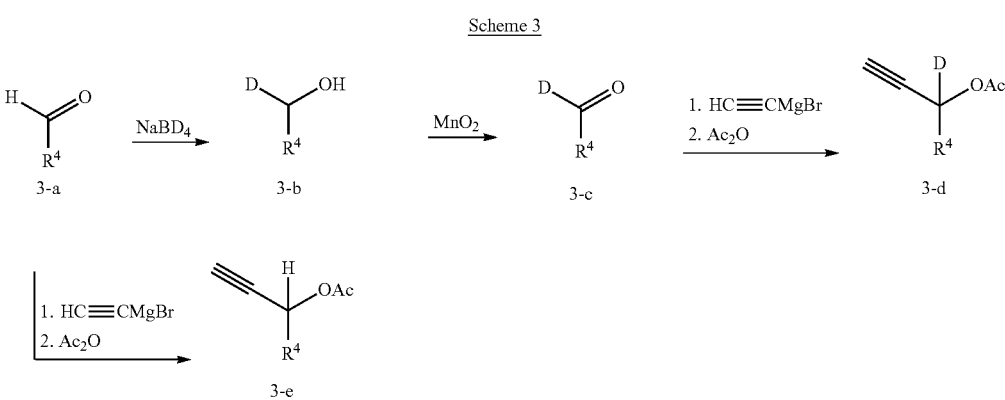

In Scheme 3, deuterated 3-c is provided by reducing suitably substituted aldehyde 3-a with a deuteride-containing reducing agent (e.g., NaBD$_4$), followed by oxidation of 3-b to the corresponding aldehyde 3-c under standard oxidizing conditions (e.g., MnO$_2$, Fe$_2$O$_3$, NiO, CuO, ZnO, ZrO$_2$, La$_2$O$_3$, Sm$_2$O$_3$, Eu$_2$O$_3$, Yb$_2$O$_3$, etc.). Compound 3-d is obtained in two steps by reaction of 3-c with ethynyl Grignard, followed by acylation of the resulting alcohol with acetic anhydride in the presence of a base (e.g., pyridine, TEA, etc.). Compound 3-e is provided in a similar two-step process by reacting suitably substituted aldehyde 3-a with ethynyl Grignard, followed by acylation of the resulting alcohol with acetic anhydride.

Scheme 4 shows a synthesis of suitably protected azide compounds of Formula 4-b, where Lg is a leaving group and $R^{3a}$ is as defined herein.

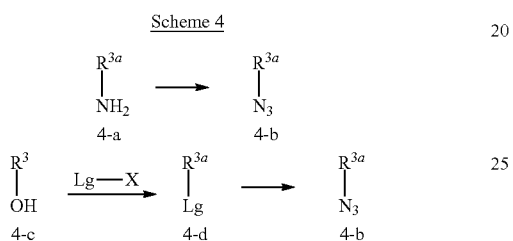

Scheme 4

In Scheme 4, suitably substituted amine 4-a is treated with a diazo transfer agent (e.g., imidazole-1-sulfonyl azide hydrochloride) to afford corresponding 4-b. Alternatively, 4-b may be obtained in two steps from alcohol 4-c by conversion of the hydroxyl moiety to a suitable leaving group (Lg) (e.g., TsO—, MsO—, NsO—, TfO—, etc.) followed by nucleophilic displacement with azide.

Scheme 5 shows a synthesis of intermediate compounds of Formula 5-c, where $R^{50}$ is alkyl and $R^{3a}$ is as defined herein.

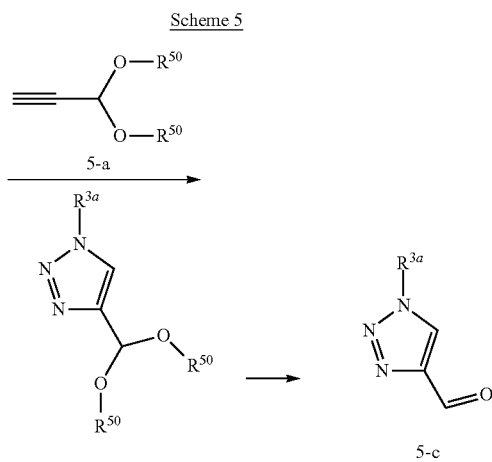

Scheme 5

In Scheme 5, suitably substituted triazole 5-b is obtained by reaction of 4-b with 5-a using standard 1,3-dipolar cycloaddition conditions. Acetal 5-b is converted to the corresponding aldehyde 5-c under standard carbonyl deprotection conditions (e.g., aqueous acid).

Scheme 6 shows an exemplary synthesis of compounds of 6b and 6c, where $R^{3a}$, m, $R^1$, $R^2$, $R^4$, $R^5$ and $R^{15}$ are as defined herein.

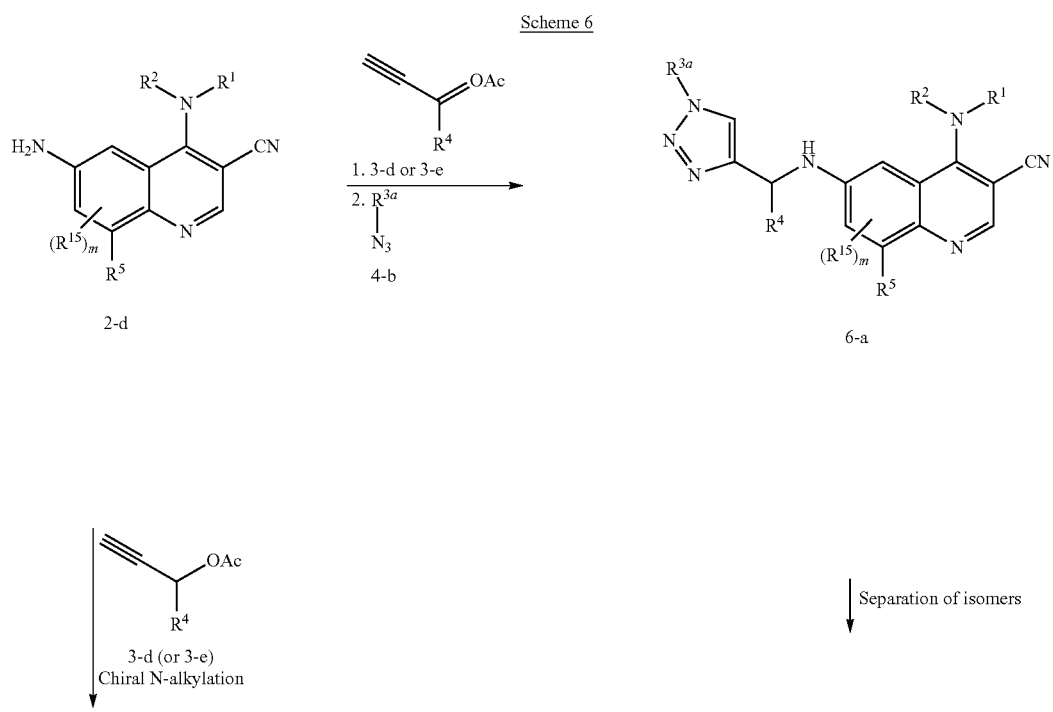

Scheme 6

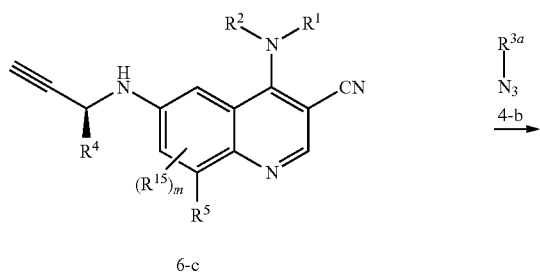

6-c

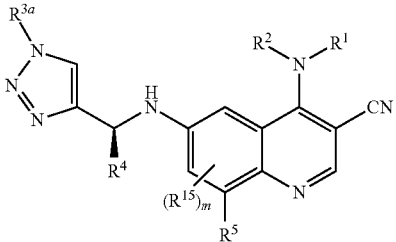

6-b

In Scheme 6, compounds of Formula 6-c can be provided via N-alkylation of amine 2-d with 3-d (or 3-e), followed by cyclization with azide 4-b under standard 1,3-dipolar cycloaddition conditions. Separation of the isomers of Formula 6-a to give compounds of Formula 6-b can be performed using standard chiral separation/resolution techniques (e.g., chiral chromatography, crystallization, etc.). Alternatively, compounds of Formula 6-b can be provided via enantioselective N-alkylation of 2-d with 3-d (or 3-e) using a chiral metal complex (e.g., [Cu(CH$_3$CN)$_4$]PF$_6$, CuOTf.benzene, Cu(OAc)$_2$, or Cu(I)I, etc., with a chiral ligand). Suitable reaction conditions and exemplary chiral ligands/complexes can be found in the literature (see, e.g., Detz, et al. Angew. Chem. Int. Ed. 2008, 47, 3777-3780). Contacting compound 6-c with azide 4-b under standard 1,3-dipolar cycloaddition conditions provide compound 6-b. 6-c may or may not be isolated prior to the addition of compound 4-b.

Scheme 7 shows an alternate synthesis, leading to compound 7-g via imine formation and subsequent nucleophilic addition, where $R^{3a}$, m, $R^1$, $R^2$, $R^3$, $R^4$, $R^5$ and $R^{15}$ are as defined herein.

Scheme 7

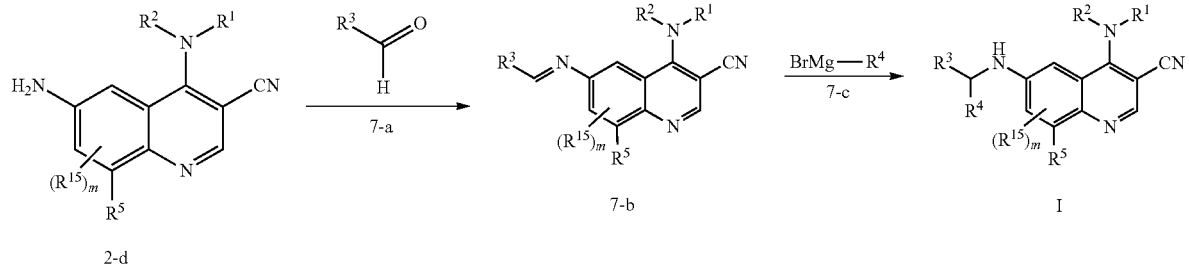

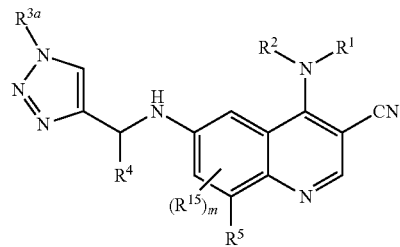

7-g

In Scheme 7, amine 2-d is reacted with aldehyde 7-a to afford the corresponding imine 7-b under standard imine-forming conditions. Compound 7-b is then reacted with Grignard reagent 7-c to provide Formula I. Alternatively, 2-d can be reacted with aldehyde 7-d to afford imine 7-e, which is then reacted with ethynyl Grignard to provide compound 7-f. Compound 7-f can then be converted to compound 7-g under standard 1,3-dipolar cycloaddition conditions with 4-b as shown in Scheme 6. Further, resolution of the isomers of Formula I or compound 7-g can be performed using standard chiral separation/resolution conditions (e.g., chiral chromatography, crystallization, etc.).

Scheme 8 shows another synthesis leading to compound 8-c, where m, $R^1$, $R^2$, $R^3$, $R^4$, $R^5$ and $R^{15}$ are as defined herein.

In Scheme 8, amine 2-d is reacted with appropriately substituted 8-a under nucleophilic substitution conditions, where Lg is a suitable leaving group, such as a halide (e.g., fluoro, chloro, bromo, iodo) or an activated alcohol (e.g., AcO—, TsO—, TfO—, MsO—, etc.) in the presence of a base, to provide compound of Formula I. Alternatively, amine 2-d is reacted with ketone 8-b to provide 8-c, which is subsequently reduced to provide compound of 8-c. Resolution of the isomers of Formula I can be performed using standard chiral separation/resolution conditions (e.g., chiral chromatography, crystallization, etc.).

Scheme 9 shows a synthesis leading to compound 9-e, where m, $R^1$, $R^2$, $R^3$, $R^4$, $R^5$ and $R^{15}$ are as defined herein.

Scheme 8

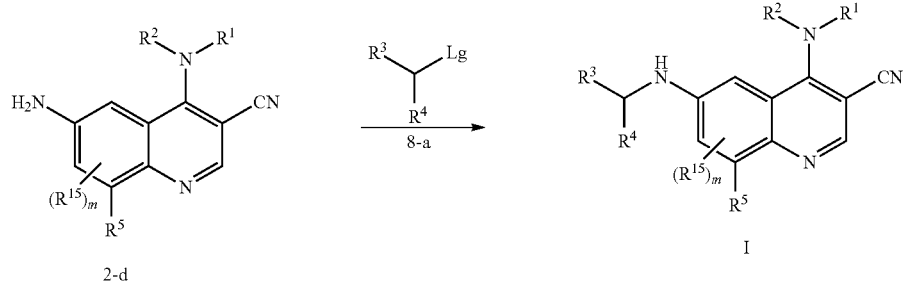

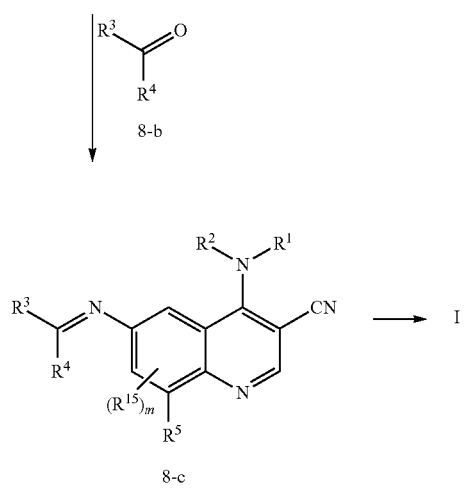

Scheme 9

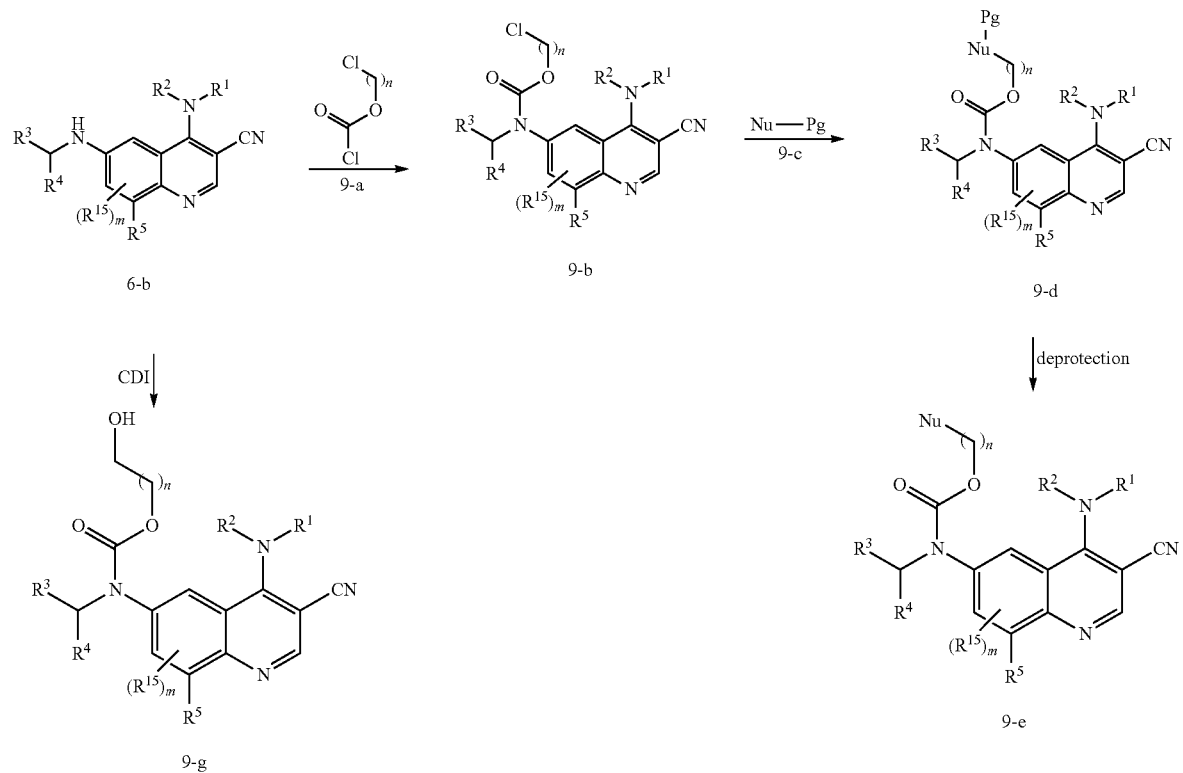

In Scheme 9, amine 6-b is reacted with appropriately substituted chloroformate 9-a, using a suitable solvent (e.g., DCM, etc.) and base (e.g., proton sponge, etc.) to give compound 9-b. Compound 9-b is then reacted with a suitable nucleophile 9-c (e.g., acetates, phosphates, etc.) and an iodide salt (e.g., tetrabutylammonium iodide, etc.), followed by a deprotection step if necessary to give compound 9-e. Amine 6-b can also be reacted with 1,1'-Carbonyldiimidazole in a suitable solvent (e.g., DMF, etc.), excess base (e.g., NaH, etc.), and an appropriately substituted alcohol to give compound 9-g.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| ° C. | Degree Celsius |
| Ac | Acetyl |
| aq. | Aqueous |
| ATP | Adenosine triphosphate |
| BOC | tert-Butoxycarbonyl |
| br | Broad |
| BSA | Bovine serum albumin |
| BLQ | Below limit of quantitation |
| Cbz | Carboxybenzyl |
| COD | Cyclooctadiene |
| COPD | Chronic obstructive pulmonary disease |
| Cp | Cyclopentadienyl |
| d | Doublet |
| DABCO | 1,4-Diazabicyclo[2.2.2]octane |
| DBU | 1,8-Diazabicyclo[5.4.0]undec-7-ene |
| DCE | Dichloroethene |
| DCM | Dichloromethane |
| dd | Doublet of doublets |
| DEF | N,N-Diethylformamide |
| DMF | Dimethylformamide |
| DMSO | Dimethylsulfoxide |
| dppf | 1,1'-Bis(diphenylphosphino)ferrocene |
| dt | Doublet-triplet |
| DTT | Dithiothreitol |
| $EC_{50}$ | The half maximal effective concentration |
| EGFR | Epidermal growth factor receptor |
| eq | Equivalents |
| ES/MS | Electro spray mass spectrometry |
| Et | Ethyl |
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hrs | Hours |
| Hz | Hertz |
| IBD | Inflammatory bowel disease |

| Abbreviation | Meaning |
| --- | --- |
| i-pr | Isopropyl |
| J | Coupling constant (MHz) |
| Kg/kg | Kilogram |
| LCMS | Liquid chromatography-mass spectrometry |
| LPS | Lipopolysaccharide |
| M | Molar |
| m | multiplet |
| M+ | Mass peak |
| M + H+ | Mass peak plus hydrogen |
| Me | Methyl |
| mg | Milligram |
| MHz | Megahertz |
| min | Minute |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |
| NMR | Nuclear magnetic resonance |
| NP-40 | Nonyl phenoxypolyethoxylethanol |
| Ns | Nosyl |
| Pd-C/Pd/C | Palladium on Carbon |
| pg | Pictogram |
| Ph | Phenyl |
| PPTS | Pyridinium p-toluenesulfonate |
| PS | Polystyrene |
| p-TSOH/pTSA | p-Toluenesulfonic acid |
| q | Quartet |
| q.s. | Quantity sufficient to achieve a stated function |
| RBF | Round bottom flask |
| RP | Reverse phase |
| RPMI | Roswell Park Memorial Institute medium |
| rt | Room temperature |
| s | Singlet |
| sat. | Saturated |
| t | Triplet |
| TBAF | Tetra-n-butylammonium fluoride |
| TBS | tert-Butyldimethylsilyl |
| t-Bu | tert-Butyl |
| TC | Thiophene-2-carboxylate |
| TEA | Triethanolamine |
| Tf | Trifluoromethanesulfonyl |
| TFA | Trifluoroacetic acid |
| THF | Tetrahydrofuran |
| Tpl-2 | Tumor Progression Locus 2 |
| TR-FRET | Time-resolved fluorescence energy transfer |
| Ts | Tosyl |
| δ | Chemical shift (ppm) |
| μL/μl | Microliter |
| μM | Micromolar |

Synthesis Cyanoquinoline Core

Ethyl (Z)-3-((2-chloro-4-nitrophenyl)amino)-2-cyanoacrylate

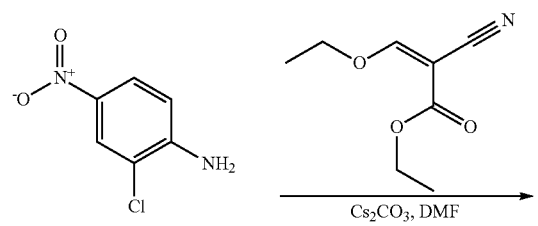

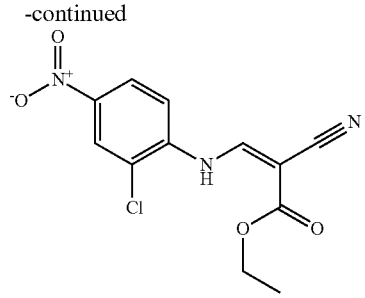

A mixture of 2-chloro-4-nitroaniline (1 eq), (Z)-ethyl 2-cyano-3-ethoxyacrylate (1.3 eq) and $Cs_2CO_3$ (1.3 eq) in DMF was heated at 45° C. overnight. After being cooled to room temperature, the mixture was poured into water. The formed solid was filtered and washed with water and dried to give the above-depicted resultant compound as a solid which was used for the next step without further purification. $^1$H NMR (DMSO-$d_6$, 300 MHz): δ 11.28 (d, J=12.9 Hz, 1H), 8.84 (d, J=12.9 Hz, 1H), 8.42 (d, J=2.4 Hz, 1H), 8.26-8.22 (m, 1H), 8.02 (d, J=9.3 Hz, 1H), 4.27 (q, J=7.2 Hz, 2H), 1.27 (t, J=7.2 Hz, 3H).

8-Chloro-6-nitro-4-oxo-1,4-dihydroquinoline-3-carbonitrile

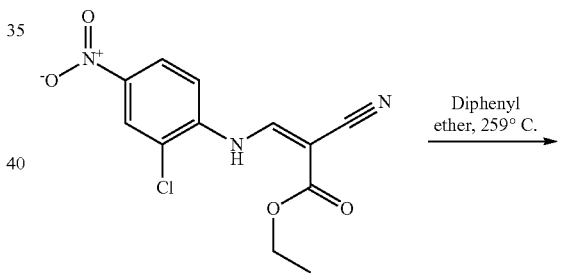

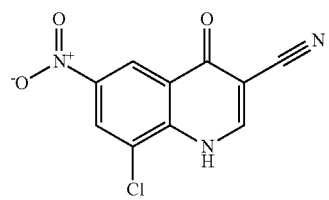

A suspension of (Z)-ethyl 3-((2-chloro-4-nitrophenyl)amino)-2-cyanoacrylate in diphenyl ether under nitrogen was heated to reflux with a sand bath in a heating mantle for 24 hours. After cooling to room temperature, the reaction mixture was poured into hexane and stirred for 2 hours. The mixture was filtered and the filter cake was washed with hexane twice to give titled compound as a solid. $^1$H NMR (DMSO-$d_6$, 300 MHz): δ 12.86 (br s, 1H), 8.73-8.71 (m, 3H).

4,8-Dichloro-6-nitroquinoline-3-carbonitrile

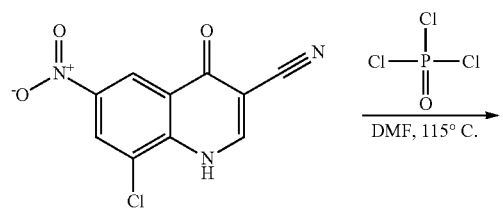

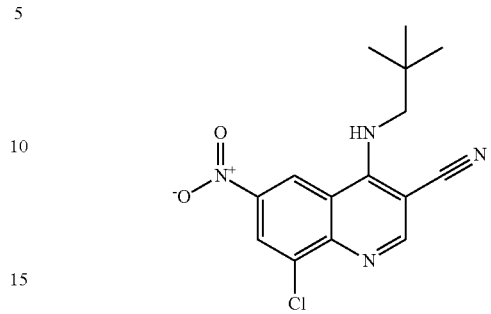

A suspension of 8-chloro-6-nitro-4-oxo-1,4-dihydroquinoline-3-carbonitrile and five drops of DMF in POCl₃ was heated at 115° C. overnight. The solution was cooled down to room temperature and the excess of POCl₃ was removed. The residue was dissolved in DCM, washed with sat. NaHCO₃, brine and dried over Na₂SO₄. The solution was filtered and concentrated to give a crude product. The residue was triturated with hexane and EtOAc to afford the title compound as a solid. $^1$H NMR (DMSO-$d_6$, 300 MHz): δ 9.50 (s, 1H), 8.98 (d, J=2.4 Hz, 1H), 8.89 (d, J=2.4 Hz, 1H).

8-chloro-4-(neopentylamino)-6-nitroquinoline-3-carbonitrile 4,8-dichloro-6-nitroquinoline-3-carbonitrile (615 mg, 2.29 mmol), neopentylamine (220 mg, 0.25 mmol) and triethylamine (278 mg, 2.75 mmol) in iso-propanol (4 mL) were heated under microwave conditions at 150° C. for 45 minutes. The reaction was cooled to room temperature. Water was added and the resulting precipitate was collected via filtration. The crude product was used in the next step without further purification. ES/MS 319.1 (M+H⁺).

Alternatively, 4,8-dichloro-6-nitroquinoline-3-carbonitrile (3000 mg, 11.2 mmol), neopentylamine (1073 mg, 12.3 mmol) and triethylamine (1246 mg, 12.3 mmol) in iso-propanol (60 mL) were heated at 80° C. for 4 hrs. The reaction was cooled to room temperature. Removed the solvents and purified the crude reaction product via chromatography on silica gel (eluent: EtOAc/hexanes) yielding the product. ES/MS (M+H⁺) 319.1.

Synthesis of (S)-8-chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile

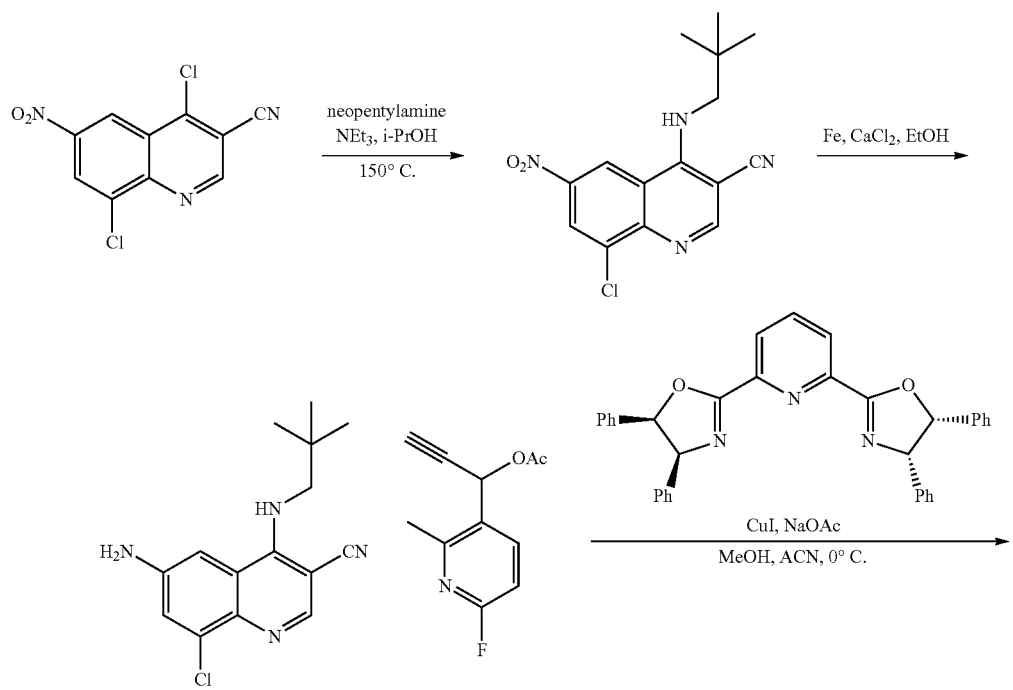

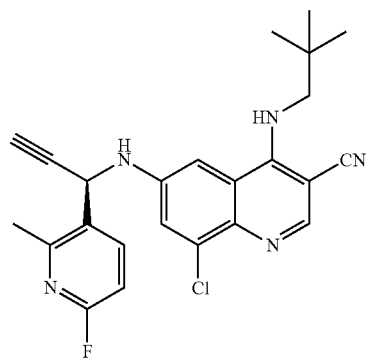

6-amino-8-chloro-4-(neopentylamino)quinoline-3-carbonitrile

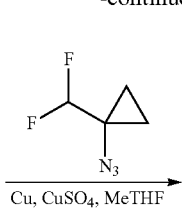

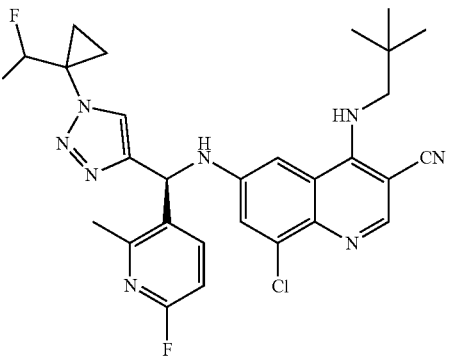

(R)-8-chloro-6-((1-(6-fluoro-2-methylpyridin-3-yl)prop-2-yn-1-yl)amino)-4-(neopentylamino)quinoline-3-carbonitrile

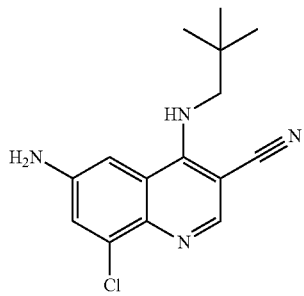 [SMILES: CC(C)(C)CNc1c(C#N)cnc2c(Cl)cc(N)cc12]

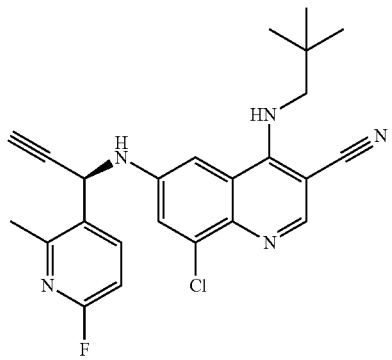 [SMILES: C#C[C@@H](Nc1cc(Cl)c2ncc(C#N)c(NCC(C)(C)C)c2c1)c1ccc(F)nc1C]

8-chloro-4-(neopentylamino)-6-nitroquinoline-3-carbonitrile (699 mg, 2.2 mmol), calcium chloride (483.6 mg, 3.28 mmol), and iron powder (612.3 mg, 10.96 mmol) were heated in ethanol (22 mL)/water (2.2 mL) at 60° C. for 1 hour. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product. ES/MS 289.1 (M+H$^+$).

Alternatively, 8-chloro-4-(neopentylamino)-6-nitroquinoline-3-carbonitrile (2,000 mg, 6.2 mmol) and tin chloride (7079 mg, 31.3 mmol) were heated at 70° C. for 4 hours. Additional tin chloride (2832 mg, 12.6 mmol) was added. After 5 hrs, the reaction was reaction was cooled to room temperature. Half of the ethanol was removed under reduced pressure. The mixture was added to NaHCO$_3$(200 mL) and diluted with EtOAc (500 mL). The organic phase was washed with brine (200 mL) and dried over sodium sulfate. The solvent was removed under reduced pressure, providing the desired material. 1H NMR (400 MHz, DMSO-d6) δ 8.19 (s, 1H), 7.32 (d, J=2.1 Hz, 1H), 7.29 (t, J=7.3 Hz, 1H), 7.18 (d, J=2.3 Hz, 1H), 5.74 (s, 2H), 3.66 (d, J=6.6 Hz, 2H), 0.96 (s, 9H).

A mixture of acetonitrile (800 ml) and methanol (800 ml), degassed with argon, was added to Cu(I)iodide (3.3 g, 17.3 mmol) and bis-oxazoline ligand (10.8 g, 20.7 mmol) and the mixture was stirred under inert atmosphere for 90 minutes at ambient temperature. The mixture was cooled to 5° C. To a 5 L rector was added 6-amino-8-chloro-4-(neopentylamino) quinoline-3-carbonitrile (100 g, 346 mmol), 1-(6-fluoro-2-methylpyridin-3-yl)prop-2-yn-1-yl acetate (86 g, 415 mmol), and sodium acetate (35.6 g, 434 mmol). The reactor was charged with a mixture of acetonitrile (800 ml) and methanol (800 ml) and degassed with argon. The reactor was cooled to −5° C. and charged with the solution containing Cu(I)iodide and bis-oxazoline ligand over 20 minutes via cannulation. After stirring at −5° C. for 48 hours, the mixture was warmed to 5° C. and to the mixture was added 4M NH$_4$Cl (2 L) over 1 hour. The mixture was warmed to 20° C. and the resulting solids were filtered and washed with water (500 mL). The wet cake was transferred to a reactor and heated with a 1:1 mixture of isopropyl acetate and ethyl acetate (3 L) and heated to 40° C. The solids were filtered through celite, the aqueous layer was removed from the filtrate, and the organic layer was concentrated under vacuum. The resulting solid was suspended in dichloromethane (1.5 L) and heated to reflux and hexane (750 mL) was slowly added. The resulting suspension was warmed to 5° C. over 4 hours. The precipitated solids were filtered (95 g) and recrystallized from dichloromethane and hexanes to give the title compound. 1H NMR (400 MHz, Methanol-d4) δ 8.27 (s, 1H), 8.24 (t, J=8.1 Hz, 1H), 7.50 (d, J=2.4 Hz, 1H), 7.17

(d, J=2.4 Hz, 1H), 6.97 (dd, J=8.4, 2.8 Hz, 1H), 5.76 (d, J=2.2 Hz, 1H), 3.94 (d, J=13.9 Hz, 1H), 3.71 (d, J=13.9 Hz, 1H), 3.06 (d, J=2.3 Hz, 1H), 2.60 (s, 3H), 1.02 (s, 9H). ES/MS 436.34 (M+H⁺).

(S)-8-chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile

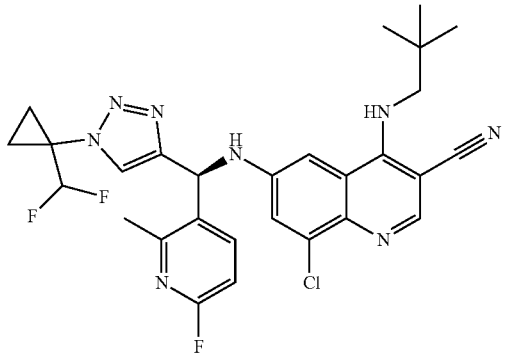 [SMILES: Cc1nc(F)ccc1[C@H](Nc1cc(Cl)c2ncc(C#N)c(NCC(C)(C)C)c2c1)c1cn(C2(C(F)F)CC2)nn1]

A 500 ml round bottom flask was charged with 1-(difluoromethyl)cyclopropanamine hydrochloride (8.2 g, 57.4 mmol). The round bottom flask was placed in a water bath and charged with acetonitrile (34 mL) followed by N,N-diisopropylethylamine (10.3 ml, 59.6 mmol). The mixture was stirred until homogeneous and to the mixture was added a solution of 2-azido-1,3-dimethylimidazolinium hexafluorophosphate (16.4 g, 57.4 mmol) in acetonitrile (32 ml) over 10 min. The mixture was stirred at 30° C. for 8 hours and N,N-diisopropylethylamine (1.98 ml, 11.47 mmol) was added and stirred at 30° C. for 18 hours. A jacketed 500 ml flask was charged with (R)-8-chloro-6-((1-(6-fluoro-2-methylpyridin-3-yl)prop-2-yn-1-yl)amino)-4-(neopentylamino)quinoline-3-carbonitrile (20 g, 45.9 mmol) and kept at 20° C. using a circulating chiller. The flask was charged with tetrahydrofuran (40 mL), copper(II) sulfate pentahydrate (1.2 g, 4.6 mmol), sodium ascorbate (2.7 g, 13.8 mmol), and water (16 mL). To the mixture was added the azide solution from above over 10 min in quarter portions. The mixture was stirred at 22° C. for 18 hours. The reaction was quenched with tributylphosphine (3.4 ml, 13.8 mmol). After stirring for 20 minutes, the mixture was diluted with ethyl acetate (160 mL) and washed with 0.5M aqueous HCl (160 mL). The organic layer was stirred with 0.5M ammonium hydroxide (160 mL) for 3 hours. The organic layer was dried with Na₂SO₄, filtered, and concentrated. The crude product was diluted with ethyl acetate (15 mL) and the mixture was heated to 50° C. To the mixture was added methyl tert-butyl ether (150 mL). The solution was cooled to 20° C. and stirred for 18 hours. The solids were filtered, washed with (10:1 MTBE:EtOAc) and dried under vacuum. The filtrate was concentrated, purified by silica chromatography, and the purified product was precipitated from ethyl acetate and methyl tert-butyl ether. The products were combined to give the titled compound.

(S)-6-6(((1-(1-(difluoromethyl)cyclopropyl)-1H-1,2,3-triazol-4-yl)(6-fluoro-2-methylpyridin-3-yl)methyl)amino)-4-(neopentylamino)quinoline-3,8-dicarbonitrile

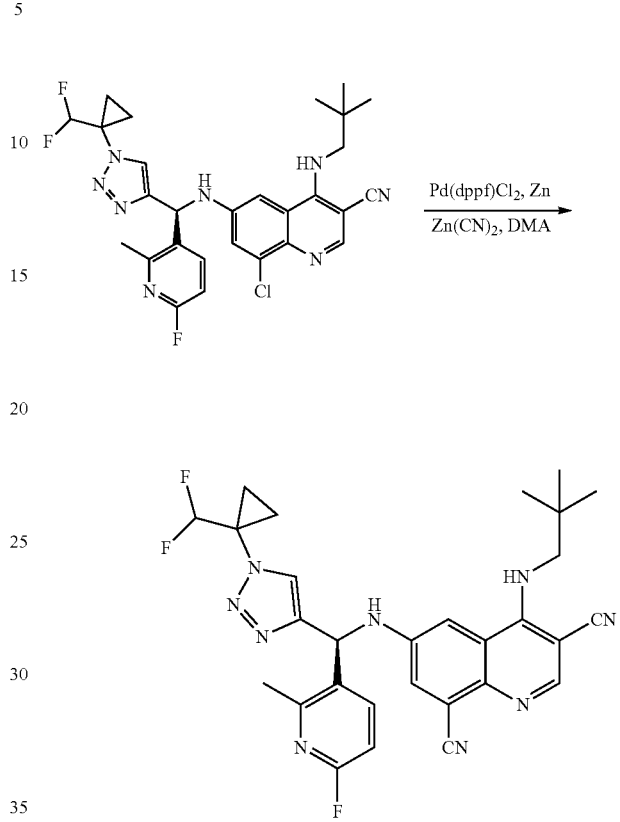

A mixture of (S)-8-chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile (95 mg, 0.14 mmol), zinc powder (1.2 mg, 0.02 mmol), Zn(CN)₂, and Pd(dppf)Cl₂ in N,N-dimethylacetamide was degassed with argon for 2 min. The mixture was heated in a microwave reactor at 200° C. for 15 minutes. The mixture was diluted with ethyl acetate (10 mL) and washed with saturated NaHCO₃(aq, 5 mL), and brine (5 mL). The organic phase was dried over sodium sulfate and treated with thiol functionalized silica to remove residual palladium. The solvent was removed under reduced pressure. The residue was subjected to flash chromatography using ethyl acetate and hexanes. The fractions containing product were combined and the solvent was removed under reduced pressure. The residue was taken up in methanol (1 mL) and water (1 mL) with 2 drops of TFA and purified by preparative HPLC using acetonitrile and water with 0.5% trifluoroacetic acid to give the title compound as the trifluoroacetic acid salt. 1H NMR (400 MHz, Methanol-d4) δ 8.36 (s, 1H), 8.05 (d, J=1.3 Hz, 1H), 7.84-7.75 (m, 2H), 7.11 (t, J=2.1 Hz, 1H), 6.86 (dd, J=8.5, 2.7 Hz, 1H), 6.24 (s, 1H), 5.94 (t, J=54.7 Hz, 1H), 3.89 (d, J=13.8 Hz, 1H), 3.70 (dd, J=13.8, 1.6 Hz, 1H), 2.50 (s, 3H), 1.55-1.50 (m, 4H), 0.89 (s, 9H). ES/MS 560.24 (M+H+).

Example 1

(Phosphonooxy)methyl (S)-41-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate

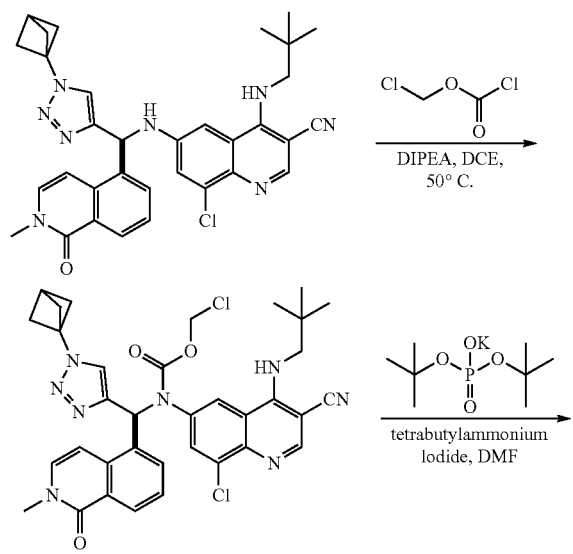

Synthesis of chloromethyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate To a DCE (1 mL) solution of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile hydrochloride salt (100 mg, 0.159 mmol) was added DIPEA (616 mg, 4.77 mmol) followed by chloromethyl carbonochloridate (1024 mg, 7.94 mmol) at room temperature. After heating at 50° C. overnight, the reaction was cooled to room temperature and extracted with ethyl acetate (100 mL). The extraction was washed with brine, dried over anhydrous sodium sulfate, and concentrated under vacuum. The residue was purified by silica gel chromatography to afford 85 mg of the desired product MS (m/z): 685.261 [M+H]$^+$.

Synthesis of ((di-tert-butoxyphosphoryl)oxy)methyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate To a DMF (5 mL) solution of chloromethyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (85 mg, 0.124 mmol) was added potassium di-tert-butyl phosphate (77 mg, 0.37 mmol) and tetrabutylammonium Iodide (22.9 mg, 0.06 mmol) at room temperature. After heating to 70° C. for 4 hrs, the reaction was cooled to room temperature and extracted with ethyl acetate (100 mL), the extraction was washed with brine, dried over anhydrous sodium sulfate and concentrated under vacuum. The residue was purified by silica gel chromatography to afford 93 mg of the desired product MS (m/z): 858.956 [M+H]$^+$.

Synthesis of (phosphonooxy)methyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate To an ACN:water (4 mL, 1:1) solution of ((di-tert-butoxyphosphoryl)oxy)methyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (93 mg, 0.108 mmol), was added AcOH (2 mL). After heating to 55° C. for 4 hrs, the reaction was concentrated under vacuum. The resulting residue was purified by RP-HPLC to yield 10 mg of (phosphonooxy)methyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate trifluoroacetic acid salt MS (m/z): 858.956 [M-FH]$^+$.

Example 2

((((S)-(1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamoyl)oxy)methyl L-alaninate

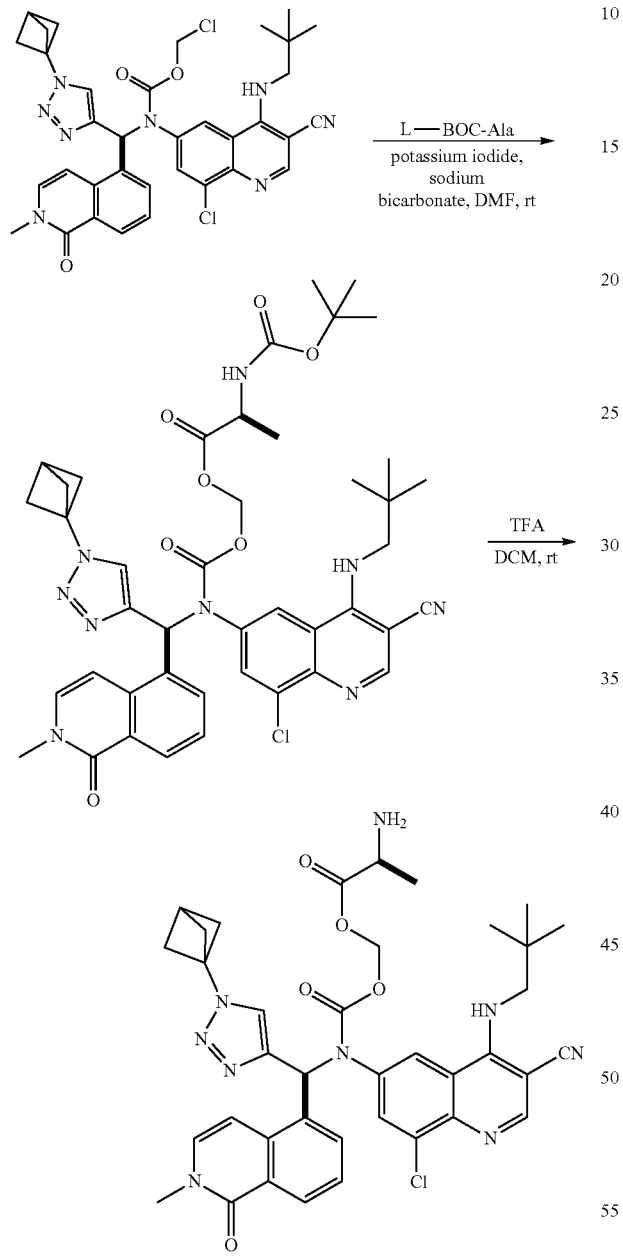

Synthesis of ((((S)-(1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamoyl)oxy)methyl (tert-butoxycarbonyl)-L-alaninate To a DMF (1 mL) solution of chloromethyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (73 mg, 0.43 mmol) was added potassium bicarbonate (37 mg, 0.43 mmol), potassium iodide (22.9 mg, 0.06 mmol), and BOC-L-alanine (55 mg, 0.29 mmol) and stirred at room temperature for 16 h. The reaction was poured onto a brine solution (~50 mL), extracted with ethyl acetate (30 mL), dried over anhydrous sodium sulfate, and concentrated under vacuum. The residue was purified by silica gel chromatography to afford 100 mg of the desired product MS (m/z): 839.0 [M+H]$^+$.

Synthesis of ((((S)-(1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamoyl)oxy) methyl L-alaninate A DCM:TFA (4 mL, 1:1) solution of ((((S)-(1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamoyl)oxy)methyl (tert-butoxycarbonyl)-L-alaninate (100 mg, 0.12 mmol), was stirred at rt for 2 h. The reaction was concentrated under vacuum and purified by RP-HPLC to yield 80 mg of the titled compound as a trifluoroacetic acid salt MS (m/z): 739.2 [M+H]$^+$.

Example 3

(((((8)-(1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamoyl)oxy)methyl L-valinate

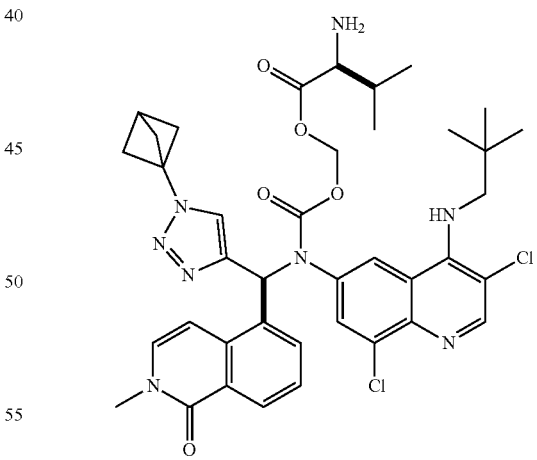

The titled compound was made similar to Example 2 using BOC-L-valine in place of BOC-L-alanine. MS (m/z): 767.1 [M+H]$^+$

Example 4

3-(Phosphonooxy)propyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate

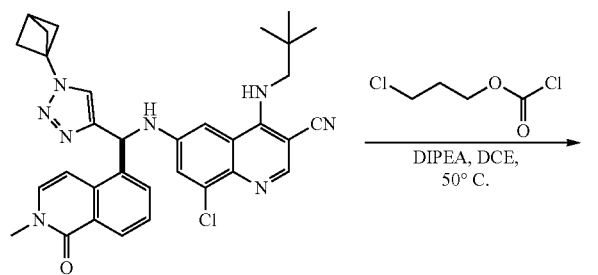

DIPEA, DCE, 50° C.

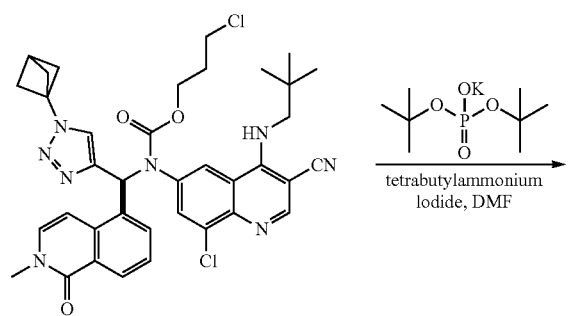

tetrabutylammonium iodide, DMF

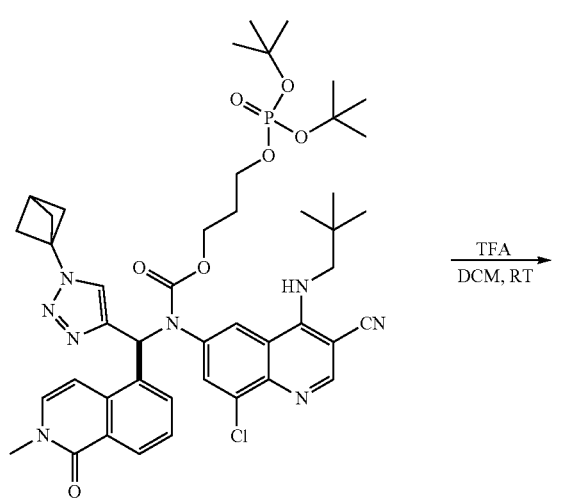

TFA
DCM, RT

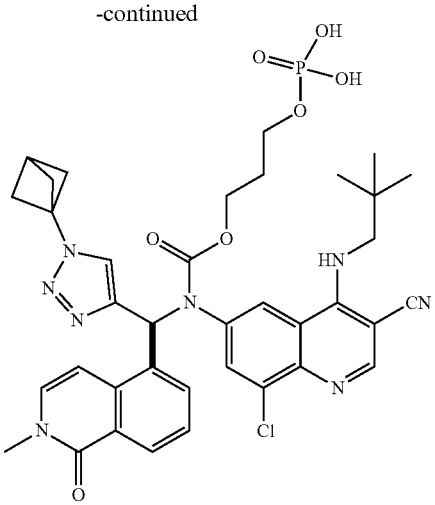

Synthesis of 3-chloropropyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate To a DCM (3 mL) solution of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile (630 mg, 1.1 mmol) was added proton sponge (683 mg, 3.2 mmol) followed by 3-chloropropyl carbonochloridate (417 mg, 2.6 mmol) at room temperature. After stirring at rt for 24 h, the reaction was concentrated under vacuum and residue was purified by silica gel chromatography to afford 233 mg of the desired product MS (m/z): 714.3 [M+H]$^+$.

Synthesis of 3-((di-tert-butoxyphosphoryl)oxy)propyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate To a THF (2 mL) solution of 3-chloropropyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (100 mg, 0.14 mmol) was added potassium di-tert-butyl phosphate (52 mg, 0.2 mmol) and tetrabutylammonium iodide (21 mg, 0.06 mmol) at room temperature. After heating to 50° C. for 16 hrs, the reaction was cooled to room temperature and extracted with ethyl acetate (100 mL), the extraction was washed with brine, dried over anhydrous sodium sulfate and concentrated under vacuum. The residue was purified by silica gel chromatography to afford 25 mg of the desired product MS. (m/z): 887.9 [M+H]$^+$.

Synthesis of 3-(Phosphonooxy)propyl (S)-(0-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate A DCM:TFA (4 mL, 1:1) solution of 3-((di-tert-butoxyphosphoryl)oxy)propyl (S)-((1-(bicyclo[1.1.1]pentan-1-yl)-

1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (25 mg, 0.28 mmol) was stirred for 2 h at rt. The reaction was concentrated under vacuum and the resulting residue was purified by RP-HPLC to yield 15 mg of the title compound as a trifluoroacetic acid salt. MS (m/z): 776.1 [M+H]⁺.

Example 5

3-Hydroxypropyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate

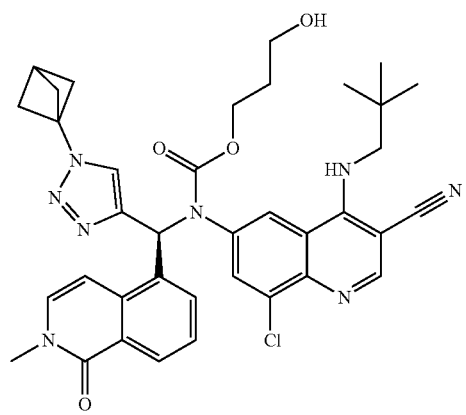 [SMILES: Cn1ccc2c([C@@H](c3cn(C45CC(C4)C5)nn3)N(C(=O)OCCCO)c3cc(Cl)c4ncc(C#N)c(NCC(C)(C)C)c4c3)cccc2c1=O]

To a suspension of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile in DMF (0.5 mL) was added NaH (60% in mineral oil) (60%, 12.14 mg, 0.3 mmol). After stirring for 10 mins, di(imidazol-1-yl)methanone (24.6 mg, 0.15 mmol) was added and the mixture was stirred at RT for 1 h. To the mixture was added 1,3-propanediol (0.25 mL) and the reaction was stirred for 1 h. The mixture was acidified with 5% TFA in water and the product was purified via RP-HPLC (eluent: water/MeCN 0.1% TFA) to yield the product as trifluoroacetate salt. ES/MS: 695.3 (M+H⁺).

Example 6

(Phosphonooxy)methyl (S)-((1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamate

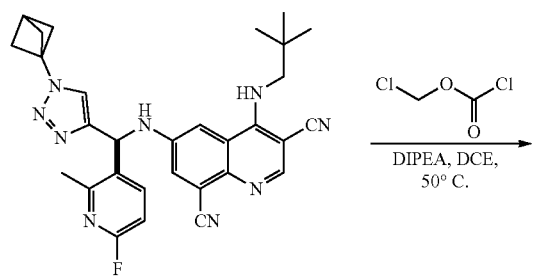

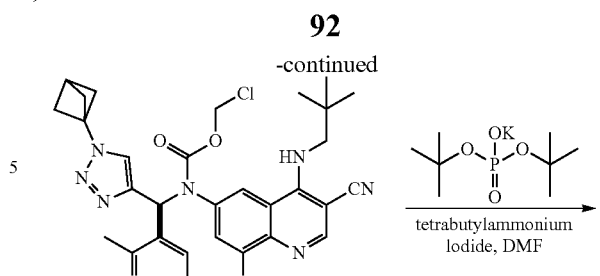

The titled compound was made similar to Example 1 using (S)-6-(((1-(bicyclo[1.1.1]pentan-1-yl)-1H-1,2,3-triazol-4-yl)(6-fluoro-2-methylpyridin-3-yl)methyl)amino)-4-(neopentylamino)quinoline-3,8-dicarbonitrile in place of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile hydrochloride salt. MS (m/z): 689.968 [M+H]⁺.

Example 7

(S)-((((1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamoyl)oxy)methyl acetate

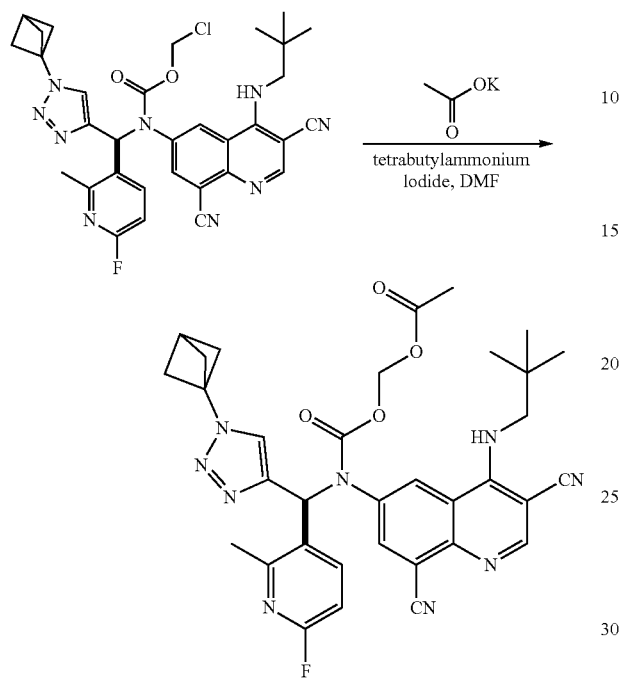

To a suspension of chloromethyl (S)-((1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamate (63 mg, 0.1 mmol) in DMF (3 mL) was added tetrabutylammonium iodide (18 mg, 0.05 mmol) followed by acetoxypotassium (20 mg, 0.2 mmol). After heating to 60° C. for 2 hrs, the reaction was cooled to room temperature and extracted with ethyl acetate (30 mL), the extraction was washed with brine, dried over anhydrous sodium sulfate and concentrated under vacuum. The mixture was acidified with 5% TFA in water and the product was purified via RP-HPLC (eluent: water/MeCN 0.1% TFA) to yield the product as trifluoroacetate salt. MS (m/z): 652.1 [M+H]$^+$

Example 8

(S)-((((1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamoyl)oxy)methyl 1-methylpiperidine-4-carboxylate

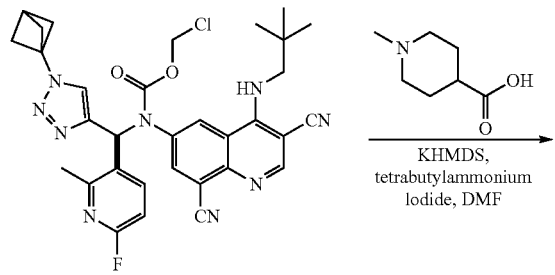

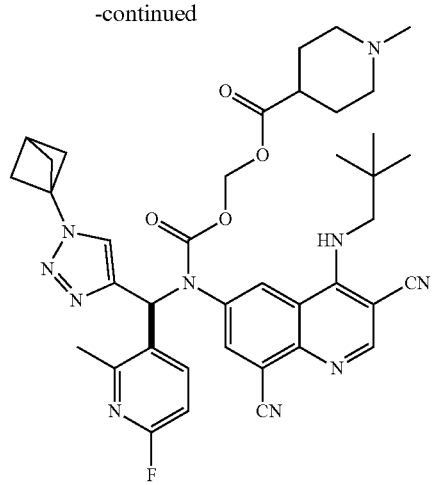

To a suspension of 1-methylpiperidine-4-carboxylic acid (13.68 mg, 0.096 mmol) in DMF (3 mL) was added KHMDS (1M solution in THF, 0.08 mL), after 15 min chloromethyl (S)-((1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamate (20 mg, 0.032 mmol) was added followed by tetrabutylammonium iodide (5.88 mg, 0.016 mmol). After 2 hrs heating at 60° C., the reaction was extracted with ethyl acetate, washed with brine and concentrated under vacuum. The resulting residue was purified by prep-HPLC to yield 13.2 mg of the title compound as the trifluoroacetic acid salt MS. (m/z): 735.29 [M+H]$^+$

Example 9

(R)-1-methoxypropan-2-yl ((S)-(1-(bicyclo[1.1.1]pentan-1-yl)-1H-1,2,3-triazol-4-yl)(6-fluoro-2-methylpyridin-3-yl)methyl)(3,8-dicyano-4-(neopentylamino)quinolin-6-yl)carbamate

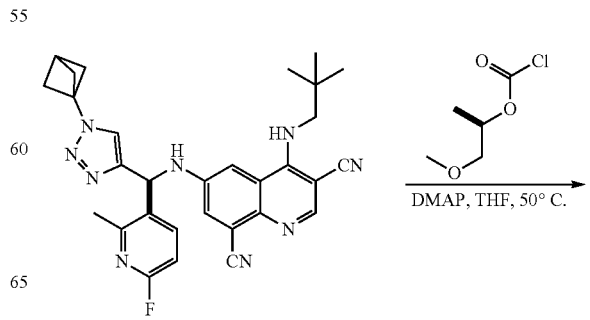

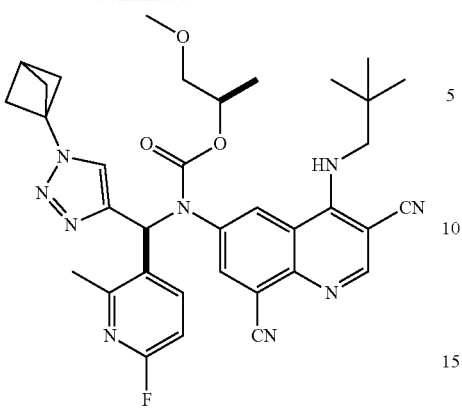

To a solution of (S)-6-(((1-(bicyclo[1.1.1]pentan-1-yl)-1H-1,2,3-triazol-4-yl)(6-fluoro-2-methylpyridin-3-yl)methyl)amino)-4-(neopentylamino)quinoline-3,8-dicarbonitrile (69 mg, 0.12 mmol) in pyridine (1 mL) was added (R)-1-methoxypropan-2-yl carbonochloridate (200 mg, 1 mmol) at 0° C. The reaction was warmed to rt and heated to 50° C. for 16 h. Upon cooling the reaction to room temperature the reaction was extracted with ethyl acetate (100 mL), washed with brine, dried over anhydrous sodium sulfate and concentrated under vacuum. The resulting residue was purified by prep-HPLC to yield 84 mg of the title compound as the trifluoroacetic acid salt. MS (m/z): 652.16 [M-t-Bu]$^+$ Example 10

(Phosphonooxy)methyl ((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)carbamate

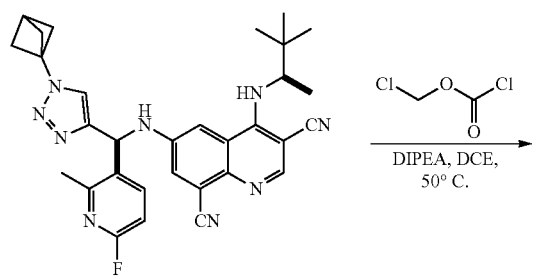

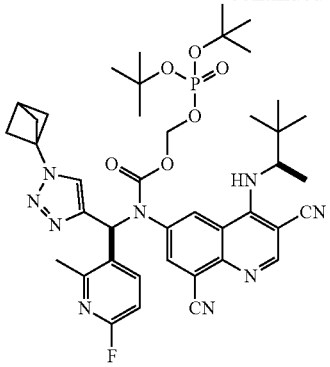

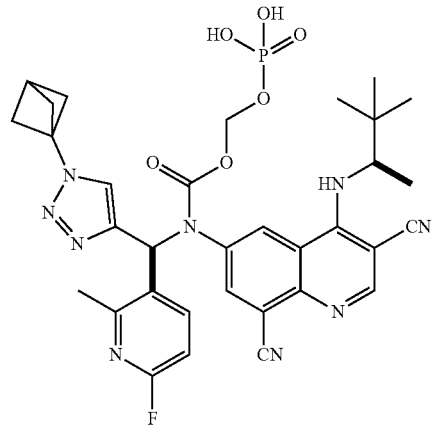

The titled compound was made similar to Example 1 using 6-(((S)-(1-(bicyclo[1.1.1]pentan-1-yl)-1H-1,2,3-triazol-4-yl)(6-fluoro-2-methylpyridin-3-yl)methyl)amino)-4-(((R)-3,3-dimethylbutan-2-yl)amino)quinoline-3,8-dicarbonitrile in place of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile hydrochloride salt. MS (m/z): 704.028 [M+H]$^+$.

Example 11

((((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)methyl dihydrogen phosphate

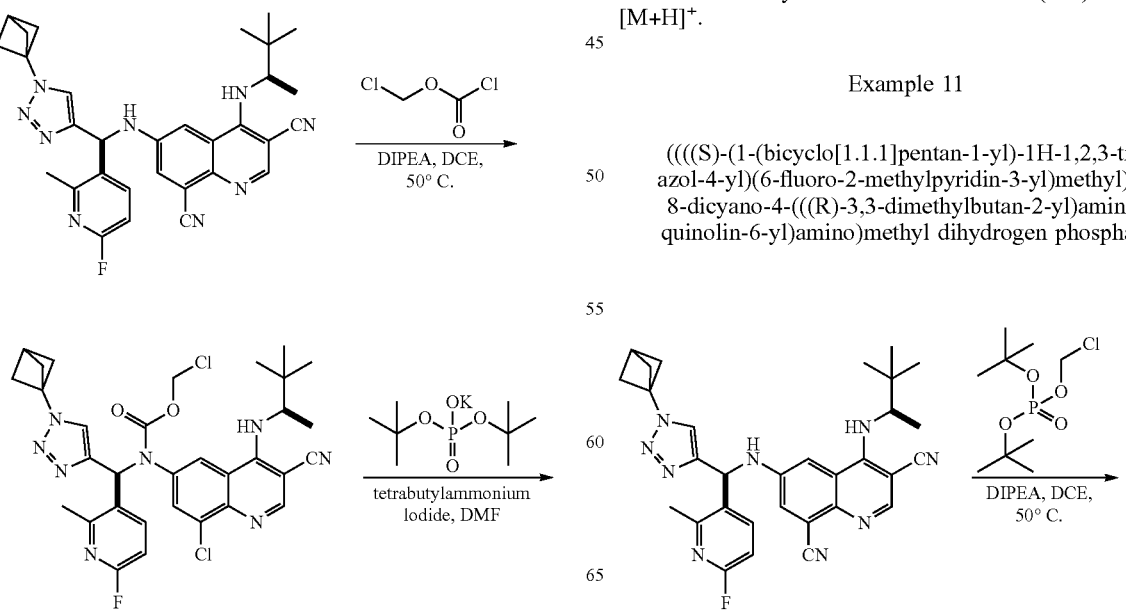

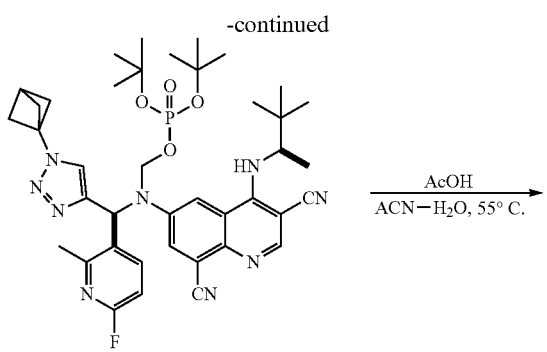

mmol) in a mixture of ACN (2 mL) and water (2 mL), was added AcOH (2 mL) was heated to 70° C. for 4 hrs. The reaction was cooled, concentrated under vacuum, and the resulting residue was purified by prep-HPLC to yield 28.5 mg of (((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl) amino)methyl dihydrogen phosphate trifluoroacetic acid salt MS (m/z): 659.935 [M+H]$^+$.

Example 12

(R)-1-methoxypropan-2-yl ((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)carbamate

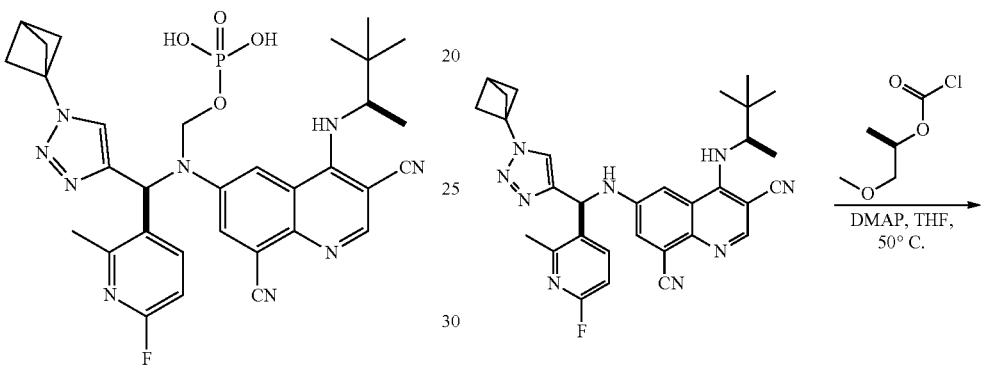

Synthesis of (((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)methyl di-tert-butyl phosphate To a solution of 6-(((S)-(1-(bicyclo[1.1.1]pentan-1-yl)-1H-1,2,3-triazol-4-yl)(6-fluoro-2-methylpyridin-3-yl)methyl)amino)-4-(((R)-3,3-dimethylbutan-2-yl)amino)quinoline-3,8-dicarbonitrile (60 mg, 0.109 mmol) in DCE (2 mL) was added DIPEA (141.8 mg, 1.09 mmol) and di-tert-butyl (chloromethyl) phosphate (112.96 g, 0.437 mmol) at room temperature. After heated to 50° C. for overnight, the reaction was cooled to room temperature and extracted with ethyl acetate (100 mL), the extraction was washed with brine, dried over anhydrous sodium sulfate and concentrated under vacuum. The residue was applied onto a silica gel column for purification, afford 22 mg of (((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)methyl di-tert-butyl phosphate. MS (m/z): 715.68 [M-t-Bu]$^+$.

Synthesis of (((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)methyl dihydrogen phosphate A solution of (((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)methyl di-tert-butyl phosphate (22 mg, 0.1

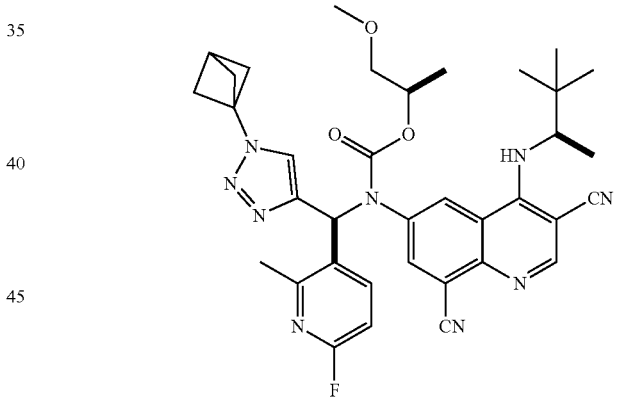

To a solution of 6-(((S)-(1-(bicyclo[1.1.1]pentan-1-yl)-1H-1,2,3-triazol-4-yl)(6-fluoro-2-methylpyridin-3-yl)methyl)amino)-4-(((R)-3,3-dimethylbutan-2-yl)amino)quinoline-3,8-dicarbonitrile (25 mg, 0.045 mmol) in DCE (1 mL) was added DIPEA (117.6 mg, 0.9 mmol) and (R)-1-methoxypropan-2-yl carbonochloridate (69.4 mg, 0.46 mmol) at room temperature. After heating to 50° C. for 16 h, the reaction was cooled to room temperature, extracted with ethyl acetate (100 mL), washed with brine, dried over anhydrous sodium sulfate and concentrated under vacuum. The residue was purified by RP-HPLC to afford 7.2 mg of the titled compound. MS (m/z): 666.17 [M-t-Bu]$^+$

Example 13

2-((((S)-(1-(bicyclo[1.1.1]pentan-1-yl)-1H-1,2,3-triazol-4-yl)(6-fluoro-2-methylpyridin-3-yl)methyl)(3,8-dicyano-4-(((R)-3,3-dimethylbutan-2-yl)amino)quinolin-6-yl)amino)-2-oxoacetic Acid

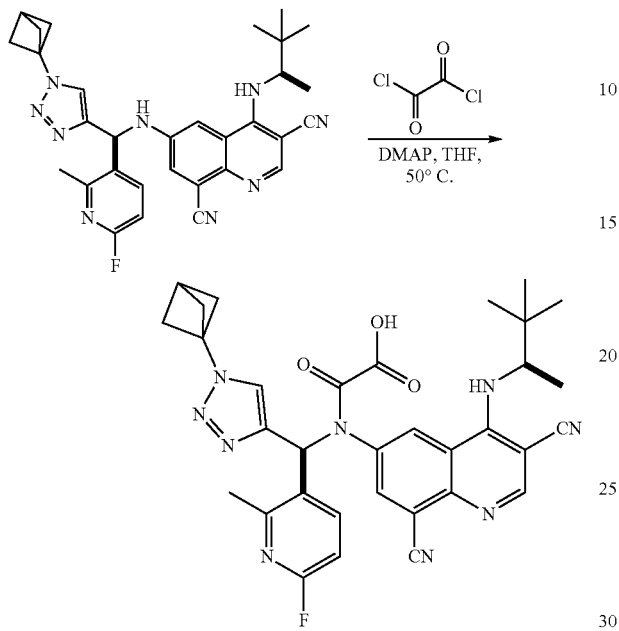

To a solution of 6-(((S)-(1-(bicyclo[1.1.1]pentan-1-yl)-1H-1,2,3-triazol-4-yl)(6-fluoro-2-methylpyridin-3-yl)methyl)amino)-4-(((R)-3,3-dimethylbutan-2-yl)amino)quinoline-3,8-dicarbonitrile (50 mg, 0.095 mmol) in THF (5 mL) was added DMAP (56 mg, 0.45 mmol) followed by oxalyl dichloride (23 mg, 0.18 mmol) at room temperature. After heating to 50° C. for 4 hrs, the reaction was cooled to room temperature and extracted with ethyl acetate (100 mL), washed with brine, dried over anhydrous sodium sulfate, and concentrated under vacuum. The residue was purified by RP-HPLC to afford 27 mg of the title compound. MS (m/z): 621.9 [M-t-Bu]+.

Example 14

3-hydroxypropyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate

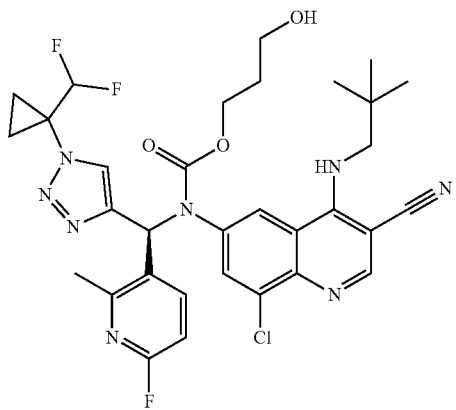 [SMILES: Cc1nc(F)ccc1[C@@H](c1cn(C2(C(F)F)CC2)nn1)N(C(=O)OCCCO)c1cc(Cl)c2ncc(C#N)c(NCC(C)(C)C)c2c1]

To a solution of (S)-8-chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile (150 mg, 0.26 mmol) and di(imidazol-1-yl)methanone (106.86 mg, 0.66 mmol) in DMF (1.0 mL) was added NaH (15.82 mg, 0.66 mmol) in 4 portions. After stirring for 30 minutes, 1,3-propanediol (0.5 mL) was added and the mixture was stirred at ambient temperature for 2 h. The mixture was extracted with EtOAc (3 mL) and washed 3 times with 5% LiCl (aq, 3 mL). The organic layer was dried with Na$_2$SO$_4$, filtered, and concentrated. The crude product was taken to next step without further purification. ES/MS: 671.20 (M+H+).

Example 15

3-(Phosphonooxy)propyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate

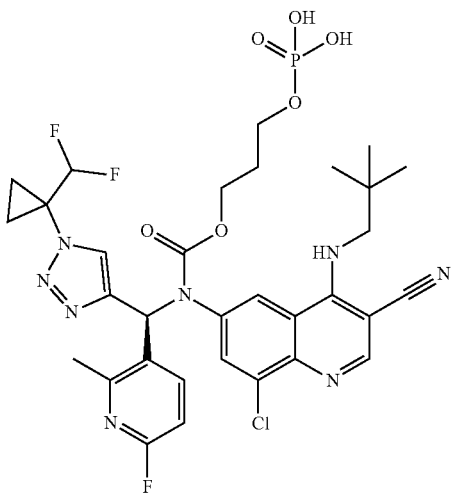 [SMILES: Cc1nc(F)ccc1[C@@H](c1cn(C2(C(F)F)CC2)nn1)N(C(=O)OCCCOP(=O)(O)O)c1cc(Cl)c2ncc(C#N)c(NCC(C)(C)C)c2c1]

To 3-hydroxypropyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate (0.11 g, 0.17 mmol) was added acetonitrile (2 mL) and EtN(i-Pr)$_2$ (145.48 µl, 0.84 mmol). To the stirring mixture was added phosphorus(V) oxychloride (47.13 µl, 0.5 mmol) and the mixture was stirred for 30 minutes. To the reaction was added 1M HCl (0.5 mL). After stirring for 1 min, the mixture was partially concentrated, diluted with DMF, and purified via RP-HPLC (eluent: water/MeCN*0.1% TFA) to yield the product as a trifluoro acetate salt (30 mg). ES/MS: 751.20 (M+H+).

Example 16

2-Hydroxyethyl (S)-41-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate

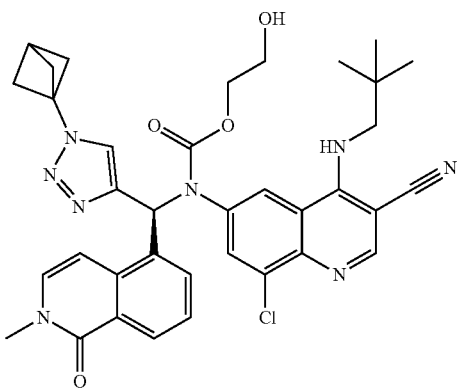 [SMILES: Cn1ccc2c([C@@H](c3cn(C45CC(C4)C5)nn3)N(C(=O)OCCO)c3cc(Cl)c4ncc(C#N)c(NCC(C)(C)C)c4c3)cccc2c1=O]

To a suspension of (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile (100 mg, 0.17 mmol) in DMF (0.5 mL) was added NaH (12.14 mg, 0.51 mmol). After stirring for 1 minute, di(imidazol-1-yl)methanone (41.01 mg, 0.25 mmol) in DMF (0.2 mL) was added dropwise and the mixture was stirred at ambient temperature for 1 h. Additional CDI (1 eq) and NaH (1 eq) was added and the reaction was stirred for 30 minutes. To the mixture was added ethylene glycol (0.2 mL) and the reaction was stirred for 1 h. The mixture was diluted with EtOAc (20 mL) and washed 3 times with 5% LiCl (aq, 15 mL). The organic layer was dried with $Na_2SO_4$, filtered, and concentrated. ES/MS: 681.22 (M+H$^+$).

Example 17

2-(Phosphonooxy)ethyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate

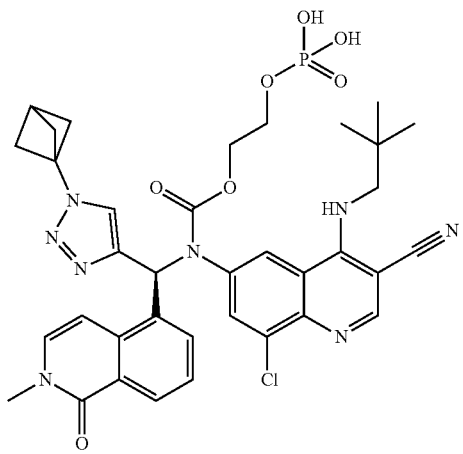 [SMILES: Cn1ccc2c([C@@H](c3cn(C45CC(C4)C5)nn3)N(C(=O)OCCOP(=O)(O)O)c3cc(Cl)c4ncc(C#N)c(NCC(C)(C)C)c4c3)cccc2c1=O]

To 2-hydroxyethyl (S)-((1-(bicyclo[1.1.1]pentan-1-yl)-1H-1,2,3-triazol-4-yl)(2-methyl-1-oxo-1,2-dihydroisoquinolin-5-yl)methyl)(8-chloro-3-cyano-4-(neopentylamino)quinolin-6-yl)carbamate (0.11 g, 0.17 mmol) was added acetonitrile (2 mL) and EtN(i-Pr)$_2$ (145.48 µl, 0.84 mmol). To the stirring mixture was added phosphorus(V) oxychloride (47.13 µl, 0.5 mmol) and the mixture was stirred for 30 minutes. To the reaction was added 1M HCl (0.5 mL). After stirring for 1 minute, the mixture was partially concentrated, diluted with DMF, and purified via RP-HPLC (eluent: water/MeCN*0.1% TFA) to yield the product as a trifluoro acetate salt (40 mg). ES/MS: 723.20 (M+H$^+$).

Example 18

Chloromethyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate

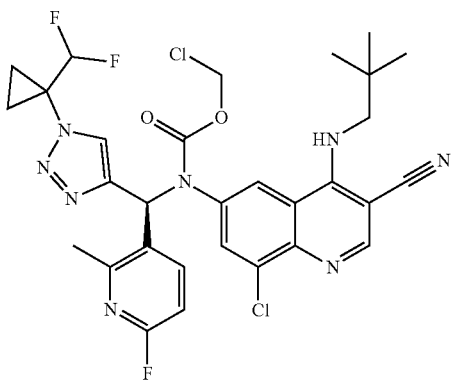 [SMILES: Cc1nc(F)ccc1[C@@H](c1cn(C2(C(F)F)CC2)nn1)N(C(=O)OCCl)c1cc(Cl)c2ncc(C#N)c(NCC(C)(C)C)c2c1]

A solution of (S)-8-chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile (0.3 g, 0.53 mmol), chloromethyl carbonochloridate (0.09 mL, 1.05 mmol), and proton sponge (0.25 g, 1.16 mmol) in dichloromethane (3 mL) was stirred for 15 hours at ambient temperature. The product was purified by silica chromatography using EtOAc in hexane (0-100%). ES/MS: 661.20 (M+H$^+$).

Example 19

((Di-tert-butoxyphosphoryl)oxy)methyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate

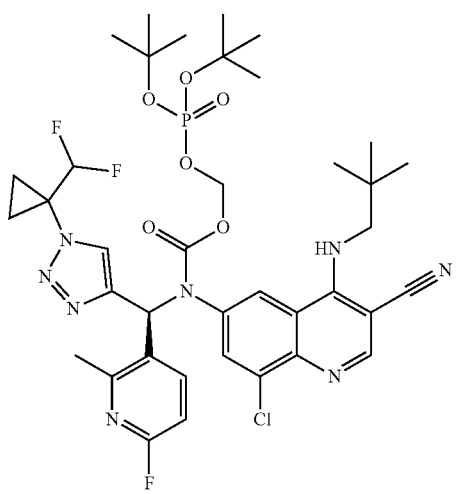 [SMILES: Cc1nc(F)ccc1[C@@H](c1cn(C2(C(F)F)CC2)nn1)N(C(=O)OCOP(=O)(OC(C)(C)C)OC(C)(C)C)c1cc(Cl)c2ncc(C#N)c(NCC(C)(C)C)c2c1]

A suspension of chloromethyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate (30.03 mg, 0.12 mmol), and tetrabutylammonium iodide (1 mg) in MeTHF (0.5 mL) was stirred at 60° C. for 1 hour. The mixture was diluted with EtOAc (3 mL) and extracted twice with water (3 mL) followed by 0.1M NaCl (aq, 10 mL). The organic layer was dried with $Na_2SO_4$, filtered, and concentrated. ES/MS: 661.20 ($M+H^+$).

Example 20

(Phosphonooxy)methyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate

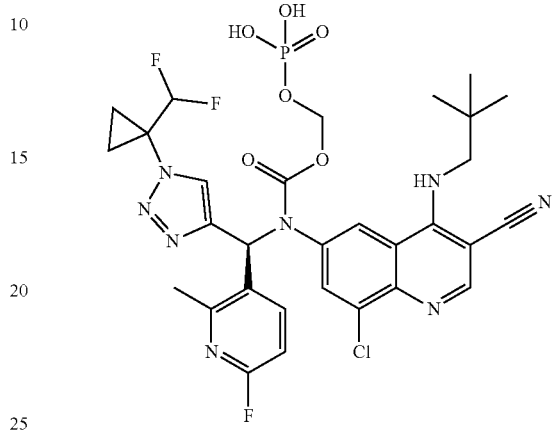

A solution of ((di-tert-butoxyphosphoryl)oxy)methyl (S)-(8-chloro-3-cyano-4-(neopentylamino)quinolin-6-yl)((1-(1-(difluoromethyl)cyclopropyl)-1H-1,2,3-triazol-4-yl)(6-fluoro-2-methylpyridin-3-yl)methyl)carbamate (50 mg, 0.06 mmol) in dichloromethane (0.1 mL) and trifluoroacetic acid (0.1 mL) was stirred at 20° C. for 1 hour. The mixture was concentrated and purified via RP-HPLC (eluent: water/MeCN*0.1% TFA) to yield the product as a trifluoro acetate salt. ES/MS: 761.20 ($M+H^+$).

Compound Examples

The following compounds were prepared according to the Examples and Procedures described herein (and indicated in Table 1 under Example/Procedure) using the appropriate starting material(s) and appropriate protecting group chemistry as needed.

TABLE 1

| Example | | $^1$H NMR |
|---|---|---|
| 1 | ![structure] | $^1$H NMR (400 MHz, Chloroform-d) δ 8.35 (s, 1H), 8.21 (s, 1H), 8.05 (s, 1H), 7.71 (s, 1H), 7.48 (d, J = 7.6 Hz, 1H), 7.43 (d, J = 7.5 Hz, 1H), 7.39 (s, 1H), 7.14 (t, J = 7.8 Hz, 1H), 6.80 (d, J = 7.6 Hz, 1H), 5.78 (s, 1H), 5.47 (s, 1H), 3.56 (s, 5H), 2.75 (s, 1H), 2.43 (s, 6H), 1.19-0.82 (m, 9H). |

TABLE 1-continued

| Example | ¹H NMR |
|---|---|
| 2 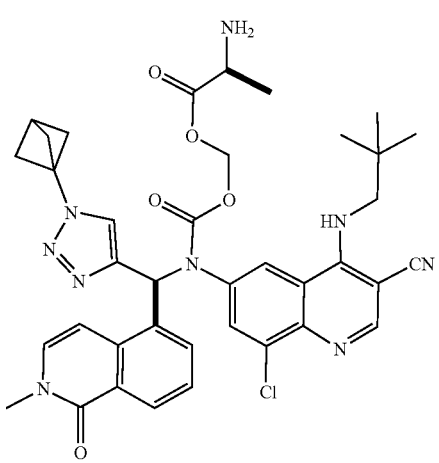 [SMILES: C[C@H](N)C(=O)OCOC(=O)N(c1cc(Cl)c2ncc(C#N)c(NCC(C)(C)C)c2c1)[C@H](c1cn(C23CC(C2)C3)nn1)c1cccc2c(=O)n(C)ccc12] | ¹H NMR (400 MHz, Methanol-d₄) δ 8.53 (s, 1H), 8.24 (dd, J = 8.1, 1.2 Hz, 1H), 8.08-7.75 (m, 3H), 7.57 (d, J = 7.6 Hz, 1H), 7.47 (s, 1H), 7.36 (dd, J = 7.5, 1.3 Hz, 1H), 7.24 (t, J = 7.8 Hz, 1H), 6.94 (d, J = 7.6 Hz, 1H), 6.04 (d, J = 5.9 Hz, 1H), 5.79 (s, 1H), 4.16 (q, J = 7.2 Hz, 1H), 3.95 (d, J = 13.8 Hz, 1H), 3.64 (s, 3H), 2.74 (s, 1H), 2.42 (s, 6H), 1.51 (d, J = 7.2 Hz, 3H), 0.99 (s, 7H). |
| 3 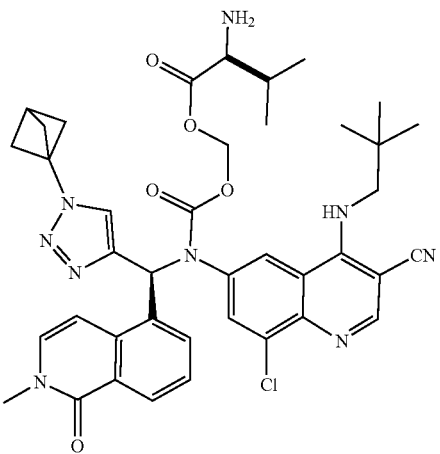 [SMILES: CC(C)[C@H](N)C(=O)OCOC(=O)N(c1cc(Cl)c2ncc(C#N)c(NCC(C)(C)C)c2c1)[C@H](c1cn(C23CC(C2)C3)nn1)c1cccc2c(=O)n(C)ccc12] | ¹H NMR (400 MHz, Methanol-d4) δ 8.53 (s, 1H), 8.24 (dd, J = 8.2, 1.1 Hz, 1H), 8.06 (s, 1H), 7.96 (s, 1H), 7.79 (s, 1H), 7.57 (d, J = 7.7 Hz, 1H), 7.47 (s, 1H), 7.41-7.34 (m, 1H), 7.25 (t, J = 7.8 Hz, 1H), 6.94 (d, J = 7.6 Hz, 1H), 6.12 (d, J = 5.8 Hz, 1H), 5.74 (s, 1H), 4.03-3.88 (m, 2H), 3.72 (d, J = 13.8 Hz, 1H), 3.65 (s, 3H), 2.74 (s, 1H), 2.43 (s, 6H), 2.31-2.18 (m, 1H), 2.06 (s, 1H), 0.99 (d, J = 16.3 Hz, 16H). |
| 4 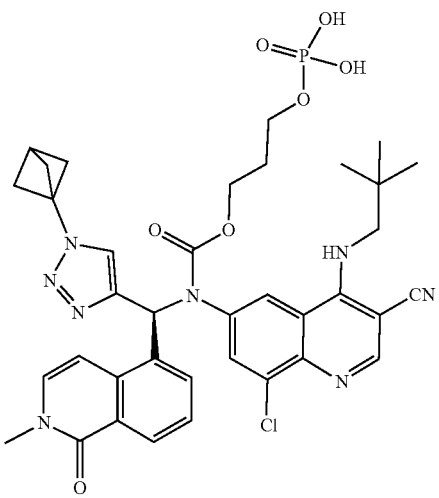 [SMILES: Cn1ccc2c([C@@H](c3cn(C45CC(C4)C5)nn3)N(C(=O)OCCCOP(=O)(O)O)c3cc(Cl)c4ncc(C#N)c(NCC(C)(C)C)c4c3)cccc2c1=O] | ¹H NMR (400 MHz, Methanol-d4) δ 8.57 (s, 1H), 8.21 (dd, J = 8.2, 1.1 Hz, 1H), 8.16-8.11 (m, 1H), 8.04 (s, 1H), 7.94 (s, 1H), 7.58 (d, J = 7.7 Hz, 1H), 7.47 (s, 1H), 7.38 (dd, J = 7.5, 1.3 Hz, 1H), 7.23 (t, J = 7.8 Hz, 1H), 6.99 (d, J = 7.6 Hz, 1H), 4.31 (qt, J = 11.1, 5.9 Hz, 2H), 4.04 (d, J = 13.9 Hz, 1H), 3.87 (q, J = 6.3 Hz, 2H), 3.78 (d, J = 13.9 Hz, 1H), 3.64 (s, 3H), 2.73 (s, 1H), 2.44 (s, 6H), 1.90 (t, J = 6.1 Hz, 2H), 1.01 (s, 9H). |

TABLE 1-continued
| Example | ¹H NMR |
|---|---|
| 5 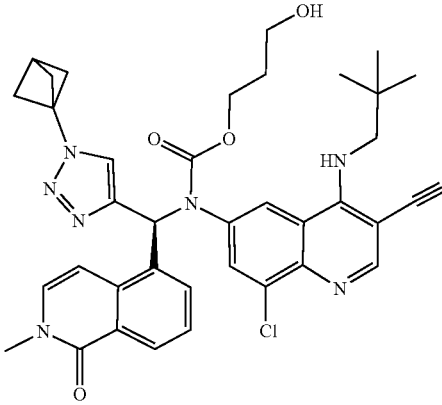 | ¹H NMR (400 MHz, CD₃OD) δ 8.62 (s, 1H), 8.22 (dd, J = 8.1, 1.1 Hz, 1H), 8.12 (d, J = 2.0 Hz, 1H), 8.02 (s, 1H), 7.93 (s, 1H), 7.58 (d, J = 7.7 Hz, 1H), 7.50-7.38 (m, 2H), 7.25 (t, J = 7.8 Hz, 1H), 6.97 (d, J = 7.6 Hz, 1H), 4.29 (t, J = 6.2 Hz, 2H), 4.01 (d, J = 13.9 Hz, 1H), 3.81 (d, J = 13.9 Hz, 1H), 3.64 (s, 3H), 3.48-3.40 (m, 1H), 2.74 (s, 1H), 2.43 (s, 6H), 1.76 (p, J = 6.2 Hz, 2H), 1.04 (s, 9H). |
| 6 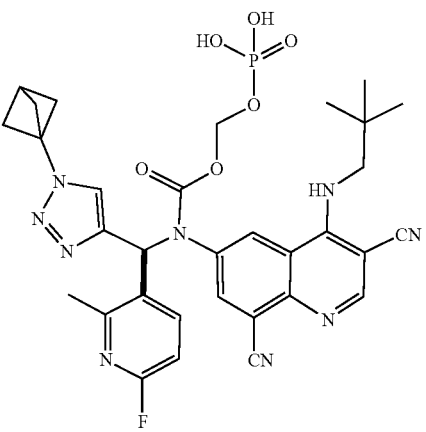 [SMILES: Cc1nc(F)ccc1[C@@H](c1cn(C23CC(C2)C3)nn1)N(C(=O)OCOP(=O)(O)O)c1cc(C#N)c2ncc(C#N)c(NCC(C)(C)C)c2c1] | ¹H NMR (400 MHz, Chloroform-d) δ 8.71 (s, 1H), 8.59 (s, 1H), 8.14 (s, 1H), 7.68 (d, J = 17.5 Hz, 2H), 7.05 (s, 1H), 6.54 (d, J = 6.8 Hz, 1H), 5.44 (d, J = 16.4 Hz, 1H), 5.29 (s, 1H), 3.90 (s, 2H), 2.71 (s, 1H), 2.54 (s, 3H), 2.37 (s, 6H), 1.06 (s, 9H). |
| 7 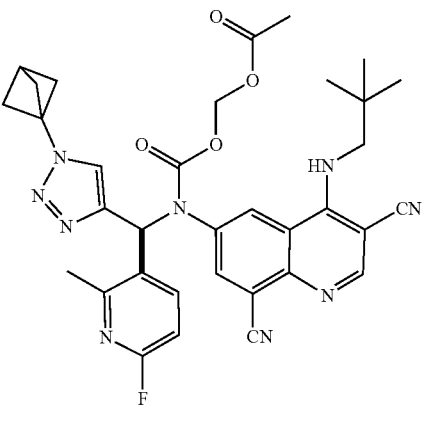 [SMILES: CC(=O)OCOC(=O)N(c1cc(C#N)c2ncc(C#N)c(NCC(C)(C)C)c2c1)[C@H](c1cn(C23CC(C2)C3)nn1)c1ccc(F)nc1C] | ¹H NMR (400 MHz, Chloroform-d) δ 8.82 (s, 1H), 8.65 (s, 1H), 7.72-7.53 (m, 2H), 7.01 (s, 1H), 6.45 (d, J = 8.5 Hz, 1H), 6.00-5.76 (m, 2H), 5.73-5.56 (m, 1H), 3.91-3.65 (m, 2H), 2.70 (d, J = 48.6 Hz, 4H), 2.41 (s, 5H), 2.09 (s, 3H), 1.21 (d, J = 27.5 Hz, 9H). |

TABLE 1-continued
| Example | | ¹H NMR |
|---|---|---|
| 8 | 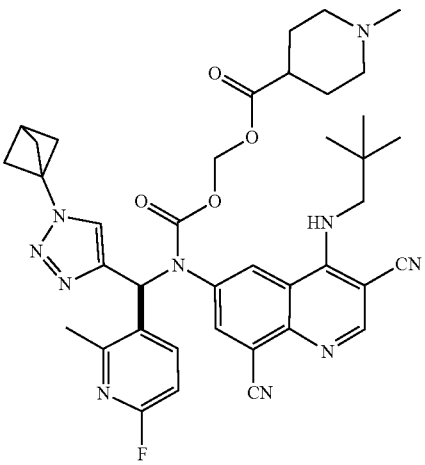 [SMILES: Cc1nc(F)ccc1[C@@H](c1cn(C23CC(C2)C3)nn1)N(C(=O)OCOC(=O)C1CCN(C)CC1)c1cc(C#N)c2ncc(C#N)c(NCC(C)(C)C)c2c1] | ¹H NMR (400 MHz, Chloroform-d) δ 8.66 (d, J = 7.1 Hz, 1H), 7.61 (d, J = 34.7 Hz, 2H), 7.47 (s, 1H), 7.04 (d, J = 14.4 Hz, 1H), 6.49-6.45 (m, 1H), 6.01 (s, 1H), 5.92 (d, J = 5.5 Hz, 1H), 5.75 (s, 1H), 3.86-3.61 (m, 4H), 3.46 (s, 1H), 2.80 (d, J = 6.3 Hz, 3H), 2.69 - 2.63 (m, 3H), 2.55 (s, 1H), 2.40 (t, J = 1.4 Hz, 6H), 2.32 (s, 1H), 2.17 (s, 3H), 1.16 (d, J = 1.7 Hz, 9H). |
| 9 | 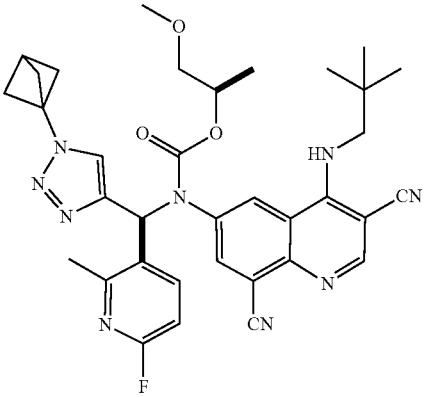 [SMILES: COC[C@@H](C)OC(=O)N(c1cc(C#N)c2ncc(C#N)c(NCC(C)(C)C)c2c1)[C@H](c1cn(C23CC(C2)C3)nn1)c1ccc(F)nc1C] | ¹H NMR (400 MHz, Chloroform-d) δ 8.66 (s, 2H), 7.77-7.66 (m, 2H), 7.59 (s, 1H), 6.98 (s, 1H), 6.55 (dd, J = 8.5, 3.2 Hz, 1H), 5.97 (s, 1H), 5.12-5.02 (m, 1H), 3.83 (d, J = 4.7 Hz, 1H), 3.73 (d, J = 3.8 Hz, 1H), 3.42-3.30 (m, 2H), 3.27 (s, 3H), 2.75 (s, 1H), 2.58 (s, 3H), 2.40 (d, J = 0.8 Hz, 6H), 1.25-1.10 (m, 12H). |
| 12 | 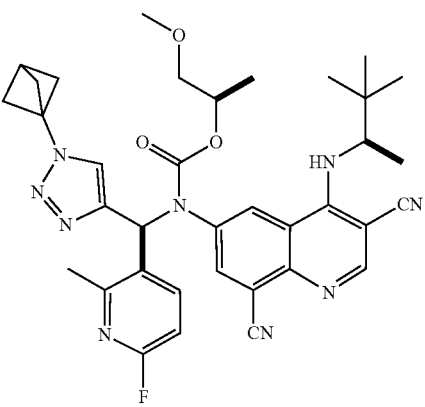 [SMILES: COC[C@@H](C)OC(=O)N(c1cc(C#N)c2ncc(C#N)c(N[C@H](C)C(C)(C)C)c2c1)[C@H](c1cn(C23CC(C2)C3)nn1)c1ccc(F)nc1C] | ¹H NMR (400 MHz, Chloroform-d) δ 8.68 (s, 1H), 8.51 (d, J = 2.2 Hz, 1H), 7.80-7.70 (m, 2H), 7.55 (s, 1H), 6.97 (s, 1H), 6.59 (dd, J = 8.6, 3.0 Hz, 1H), 5.95 (d, J = 10.0 Hz, 1H), 5.07 (d, J = 3.4 Hz, 1H), 4.64 (t, J = 8.2 Hz, 1H), 3.33 (dd, J = 10.6, 3.2 Hz, 1H), 3.27 (s, 3H), 2.75 (s, 1H), 2.57 (s, 3H), 2.39 (s, 6H), 1.39 (d, J = 6.3 Hz, 3H), 1.19 (d, J = 6.4 Hz, 3H), 1.09 (s, 9H). |

| Example | <sup>1</sup>H NMR |
|---|---|
| 13 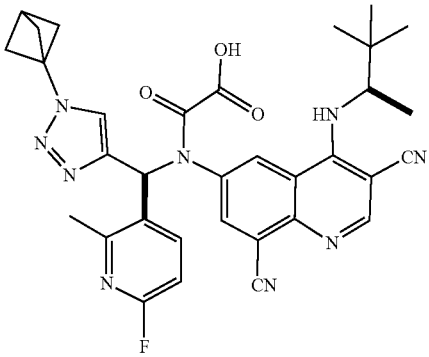 [SMILES: Cc1nc(F)ccc1[C@@H](c1cn(C23CC(C2)C3)nn1)N(C(=O)C(=O)O)c1cc(C#N)c2ncc(C#N)c(N[C@H](C)C(C)(C)C)c2c1] | <sup>1</sup>H NMR (400 MHz, Chloroform-d) δ 8.66 (d, J = 6.5 Hz, 1H), 7.69 (d, J = 8.1 Hz, 1H), 7.66 (d, J = 4.5 Hz, 1H), 7.32 (d, J = 11.0 Hz, 1H), 6.88 (d, J = 36.1 Hz, 1H), 6.50 (t, J = 10.2 Hz, 1H), 4.74 (s, 1H), 2.75 (d, J = 3.2 Hz, 1H), 2.62 (s, 3H), 2.40 (d, J = 6.4 Hz, 6H), 1.38 (d, J = 6.8 Hz, 3H), 1.04 (d, J = 33.2 Hz, 9H). |
| 14 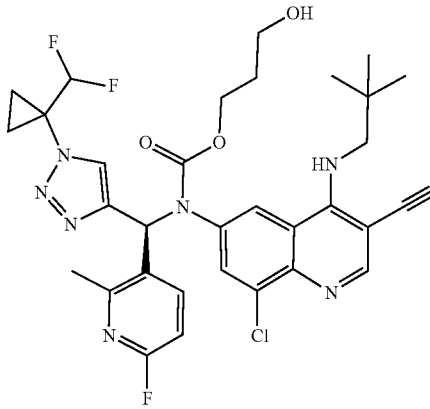 | <sup>1</sup>H NMR (400 MHz, Methanol-d4) S 8.62 (s, 1H), 8.22 (dd, J = 8.1, 1.1 Hz, 1H), 8.12 (d, J = 2.0 Hz, 1H), 8.02 (s, 1H), 7.93 (s, 1H), 7.58 (d, J = 7.7. Hz, 1H), 7.50-7.38 (m, 2H), 7.25 (t, J = 7.8 Hz, 1H), 6.97 (d, J = 7.6 Hz, 1H), 4.29 (t, J = 6.2 Hz, 2H), 4.01 (d, J = 13.9 Hz, 1H), 3.81 (d, J = 13.9 Hz, 1H), 3.64 (s, 3H), 3.48-3.40 (m, 1H), 2.74 (s, 1H), 2.43 (s, 6H), 1.76 (p, J = 6.2 Hz, 2H), 1.04 (s, 9H). |
| 15 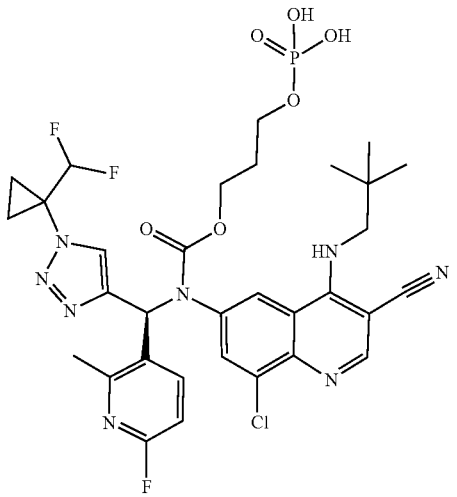 [SMILES: Cc1nc(F)ccc1[C@@H](c1cn(C2(C(F)F)CC2)nn1)N(C(=O)OCCCOP(=O)(O)O)c1cc(Cl)c2ncc(C#N)c(NCC(C)(C)C)c2c1] | <sup>1</sup>H NMR (400 MHz, CD<sub>3</sub>OD) δ 8.67 (s, 1H), 8.26-7.96 (m, 3H), 7.69 (t, J = 8.1 Hz, 1H), 7.12 (s, 1H), 6.71 (dd, J = 8.6, 2.9 Hz, 1H), 5.93 (t, J = 54.6 Hz, 1H), 4.38-4.19 (m, 2H), 4.13 (d, J = 14.0 Hz, 1H), 3.94-3.77 (m, 3H), 2.65 (s, 3H), 1.97-1.77 (m, 2H), 1.65-1.46 (m, 4H), 1.10 (s, 9H). |

TABLE 1-continued

| Example | | ¹H NMR |
|---|---|---|
| 17 | 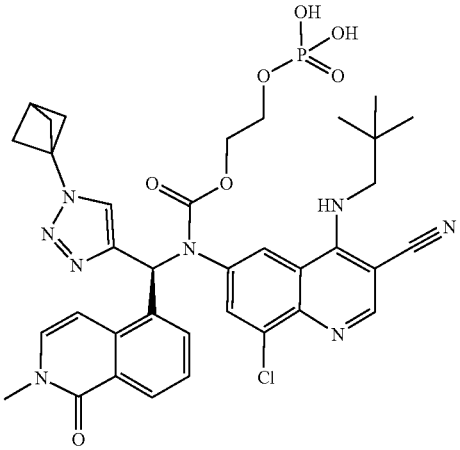 [SMILES: Cn1ccc2c([C@@H](c3cn(C45CC(C4)C5)nn3)N(C(=O)OCCOP(=O)(O)O)c3cc(Cl)c4ncc(C#N)c(NCC(C)(C)C)c4c3)cccc2c1=O] | ¹H NMR (400 MHz, CD₃OD) δ 8.62 (s, 1H), 8.44 (s, 1H), 8.20 (s, 1H), 8.03 (d, J = 2.0 Hz, 1H), 7.75 (t, J = 8.1 Hz, 1H), 7.15 (s, 1H), 6.74 (dd, J = 8.6, 2.9 Hz, 1H), 5.96 (t, J = 54.7 Hz, 2H), 5.61 (dd, J = 16.5, 5.5 Hz, 1H), 5.49 (dd, J = 13.8, 5.4 Hz, 1H), 4.14 (d, J = 13.9 Hz, 1H), 3.87 (d, J = 14.0 Hz, 1H), 2.61 (s, 3H), 1.63-1.45 (m, 4H), 1.11 (s, 9H). |
| 20 | 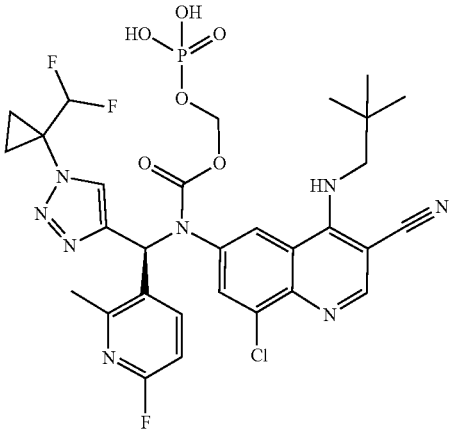 [SMILES: Cc1nc(F)ccc1[C@@H](c1cn(C2(C(F)F)CC2)nn1)N(C(=O)OCOP(=O)(O)O)c1cc(Cl)c2ncc(C#N)c(NCC(C)(C)C)c2c1] | ¹H NMR (400 MHz, CD₃OD) δ 8.62 (s, 1H), 8.30-8.12 (m, 3H), 8.09 (s, 1H), 7.60 (d, J = 7.6 Hz, 1H), 7.49 (s, 1H), 7.40 (dd, J = 7.7, 1.3 Hz, 1H), 7.23 (t, J = 7.8 Hz, 1H), 7.02 (d, J = 7.7 Hz, 1H), 4.63-4.46 (m, 1H), 4.35-4.01 (m, 4H), 3.76 (d, J = 13.9 Hz, 1H), 3.63 (s, 3H), 2.75 (s, 1H), 2.46 (s, 6H), 1.03 (s, 9H). |

Biological Assays

Example 21

Human and Dog GI S9 Stability

GI S9 stability assays were performed. Generally, a substrate concentration of 2 μM was used, a protein concentration of 1.0 mg/mL intestinal S9 was used, and a reaction buffer of 1× phosphate buffered saline (PBS) was used. Intestinal S9 was provided by BioIVT (dog) or Xenotech (human). Reaction compositions contained 5 μL of compound of interest (prepared as 100 μM stock solution, 1:1 ACN:H₂O) and 245 μL of intestinal S9 solution (S9 was diluted with 1×PBS to a protein concentration of 1.02 mg/ML) and were provided as 250 μL total volume per well. At time points of 0 min, 10 min, 20 min, 30 min, 60 min, and 120 min, 25 μL at each timepoint was added to a plate with 225 μL quenching solution (10% MeOH, 90% ACN, and 200 nM Labetalol as internal standard). Plates were vortexed, and then centrifuged at 3000×G for 30 minutes. 150 μL of supernatant was transferred to new plates and 150 μL water was added. New plates were vortexed to mix.

Samples were analyzed with a Leap HTC Autosampler and a Dionex UltiMate 3000 HPLC system interfaced to a Thermo Q-Exactive mass spectrometer operation in positive ion electrospray mode. A Thermo Scientific Hypersil GOLD (1.9 μM particle size, 50×2.1 mm) HPLC column was used and mobile phase was pumped at 0.5 mL/min. Elution of analytes was achieved by a series of linear gradients of acetonitrile in water containing 0.1% (v/v) formic acid. Quantification was by analyte/internal standard peak area ratio (PAR). Results are shown in Table 2 below.

TABLE 2

| Example | Human GI S9 T½ (min) | Dog GI S9 T½ (min) |
|---|---|---|
| 1 | 43 | 26 |
| 2 | <1 | 1 |
| 4 | 21 | 12 |
| 6 | 25 | 14 |
| 7 | 3 | |
| 8 | 165 | |
| 9 | 789 | |
| 10 | 26 | 20 |
| 11 | ND | ND |
| 12 | 477 | 528 |
| 13 | 789 | 789 |

Example 22

Solubility in FaSSIF and FeSSIF

The aqueous solubility of compounds over a time of 2.5 hours was assessed. Solubility was determined at ambient temperature in buffered fasted-state simulated intestinal fluid (FaSSIF, pH 6.5) and buffered fed-state simulated intestinal fluid (FeSSIF, pH 5.0) prepared in-house using BioRelevant Simulated Intestinal Fluid (SIF) powder. Solids were added to FaSSIF or FeSSIF in 1.5-mL Eppendorf tubes, sonicated for 1 minute, then agitated for 2.5 hours in an Eppendorf ThermoMixer C. To determine concentration in solution, the suspensions were centrifuged for 10 min at 14,800 rpm and supernatants were diluted to a volume of 1 mL with 1:1 v/v acetonitrile:water. All diluted supernatants were analyzed by UPLC using a Waters Acquity UPLC with a PDA UV detector. Results are depicted in Table 3.

TABLE 3

| Example | FaSSIF (pH 6.5) (µg/mL) | FeSSIF (pH 5.0) (µg/mL) |
|---|---|---|
| 1 | >1580 | >2170 |
| 2 | >1881 | >1908 |
| 4 | 4 | 210 |
| 7 | 12 | 42 |
| 8 | 77 | 450 |
| 9 | 12 | 52 |

Example 23

Human and Dog Plasma Stability

Plasma stability assays were performed in human and dog. Duplicate sets were performed with a tecan liquid handler or with cluster tubes in a heat block. Generally, a substrate concentration of 2 µM was used. Plasma in sodium EDTA was provided by BioIVT as whole plasma with K2 EDA as anti-coagulent. Reaction compositions were prepared by combining 6 µL compound (compound (100 µM stock solution, 1:1 ACN:H2O) with 294 µL plasma in an incubation well of a plate. Samples were assessed at time points of 3 minutes, 30 minutes, 1 hour, 2 hours, 3 hours, and 4 hours. At each time point, 25 µL was added to a plate with 225 µL quenching solution (100% ACN with 200 nM propranolol as internal standard). After the plates were vortexed, they were centrifuged at 3000 rpm for 30 minutes. 150 µL of supernatant was transferred to a new plate and 150 µL water was added. New plates were vortexed to mix.

Samples were analyzed with a Leap HTC Autosampler and a Dionex UltiMate 3000 HPLC system interfaced to a Thermo Q-Exactive mass spectrometer operation in positive ion electrospray mode. A Thermo Scientific Hypersil GOLD (1.9 µM particle size, 50×2.1 mm) HPLC column was used and mobile phase was pumped at 0.5 mL/min. Elution of analytes was achieved by a series of linear gradients of acetonitrile in water containing 0.1% (v/v) formic acid. Quantification was by analyte/internal standard peak area ratio (PAR). Results are shown in Table 4 below.

TABLE 4

| Example | Human Plasma T½ (min) | Dog Plasma T½ (min) |
|---|---|---|
| 1 | 369 | 278 |
| 2 | 14 | 3 |
| 8 | 237 | |
| 9 | 1584 | |

Example 24

In Vivo Dog Pharmacokinetics Experiments

In vivo dog pharmacokinetic experiments of compound B and C were assessed as follows.

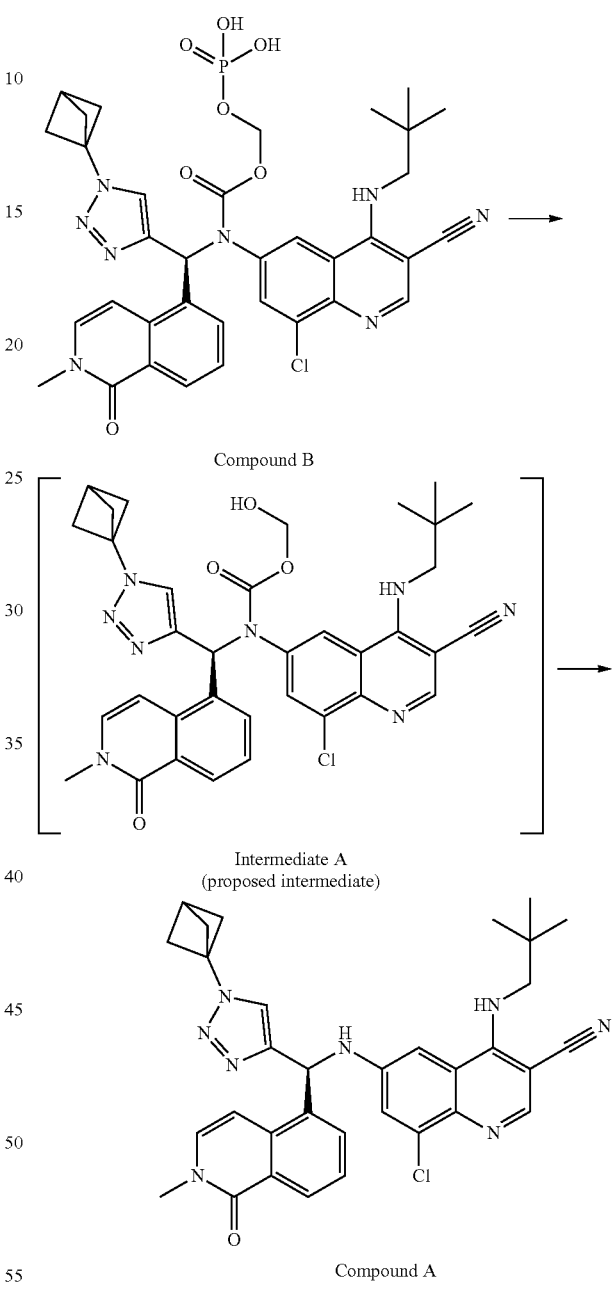

Compound B

Intermediate A
(proposed intermediate)

Compound A

Compound B was dosed as a powder in capsule to beagle dogs (N=3) using the following formulation: 57.5% by weight of amorphous compound B (9.7 mg-eq/kg), 4.7% crospovidone; 18.7% Lactose, monohydrate; 0.4% Magnesium stearate; 18.7% microcrystalline cellulose. Compound A was dosed separately as a powder in capsule to beagle dogs (N=3) using the following formulation: 20% of amorphous compound A, 0.75% magnesium stearate, 3% hydroxypropylcellulose, 5% tocopheryl polyethylene glycol succinate, 20% hydroxypropyl methylcellulose, and 51.25% microcrystalline cellulose. Samples were assessed for the presence of Compound B, proposed Intermediate A, and Compound A. FIG. 1 shows plasma concentrations of Compound A (nM) during a 72 hour time period after dosing with either Compound B or Compound A using the previously described powder in capsule formulation. As is shown in Table 5, the $AUC_{0-72\,h}$ measured for Compound A in plasma was higher after dosing with Compound B than the value measured after dosing with an equivalent dose of Compound A.

TABLE 5

| Dose | Compound | $AUC_{0-72\,h}$ (nM · h) |
| --- | --- | --- |
| Compound B (9.7 mg-eq/kg) | Compound B | BLQ |
|  | Intermediate A | BLQ |
|  | Compound A | 149000 |
| Compound A (9.7 mg/kg) | Compound A | 65100 |

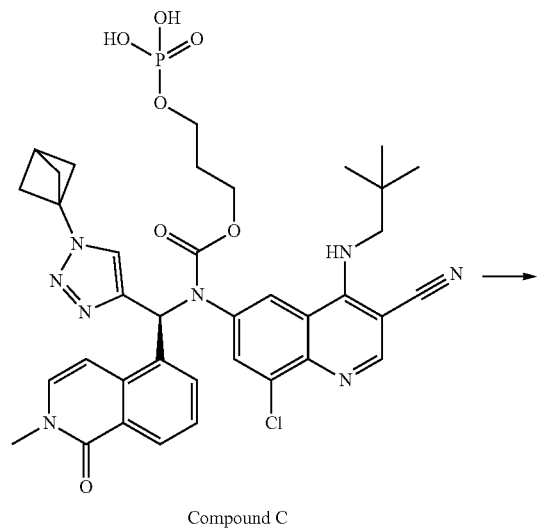

Compound C

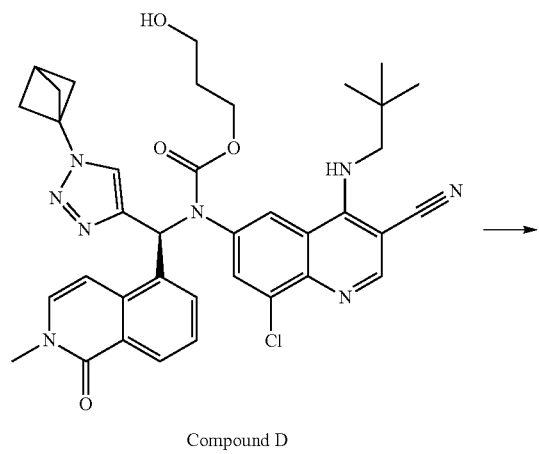

Compound D

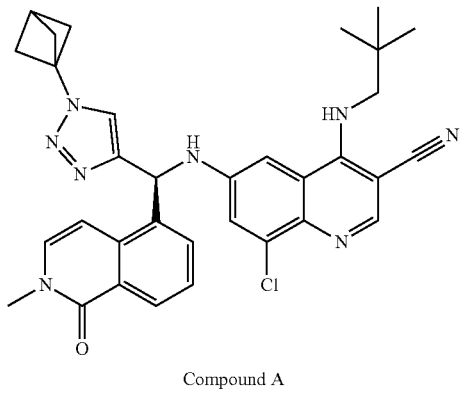

Compound A

Figure 2:
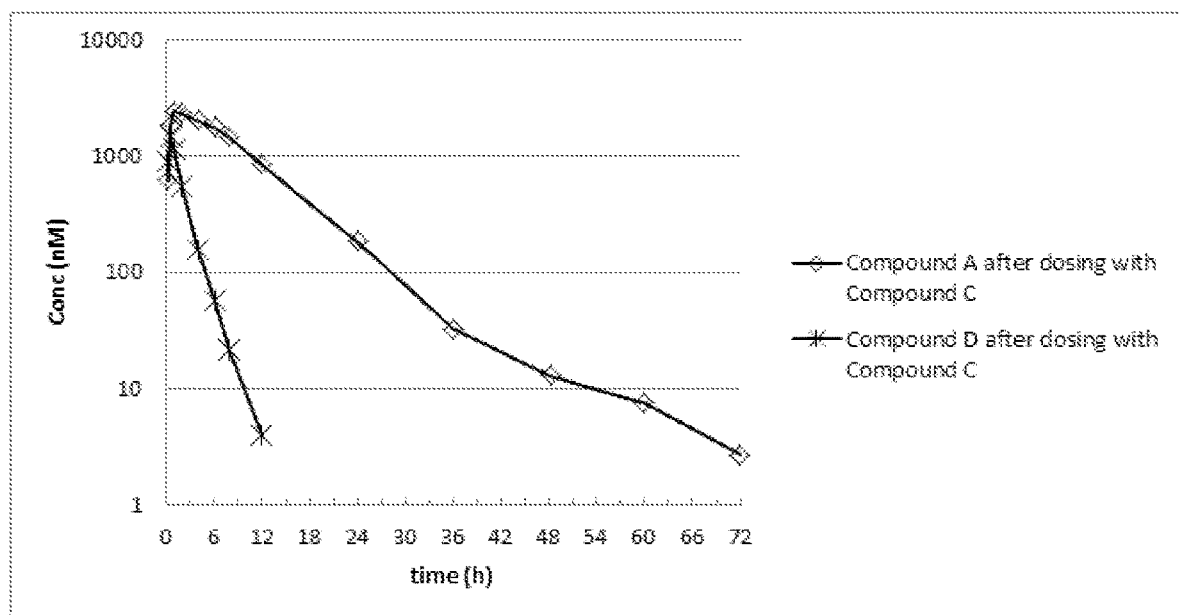
FIG. 2 depicts plasma concentration over time of Compound A and Compound D following oral administration of Compound C to dogs over time.

Compound C was dosed as 3 mg/mL solution to beagle dogs (N=3) using the following formulation: 3 mg/kg Compound C, 5% ethanol, 55% polyethylene glycol 300, and 40% (5% dextrose in water). Samples were assessed for the presence of Compound C, intermediate Compound D, and Compound A. FIG. 2 shows plasma concentrations of Compound A and Compound D (nM) during a 72 hour time period after dosing with Compound C using the previously described solution formulation. As can be seen in FIG. 2 and reported in Table 6, Compound C converted in vivo to both Compound D and Compound A in measurable amounts.

TABLE 6

| Dose | Species | $AUC_{0-72\,h}$ (nM · h) |
| --- | --- | --- |
| Compound C (3 mg-eq/kg) | Compound C | BLQ |
|  | Compound D | 2984 |
|  | Compound A | 27360 |

The invention claimed is:

1. A compound having the formula:

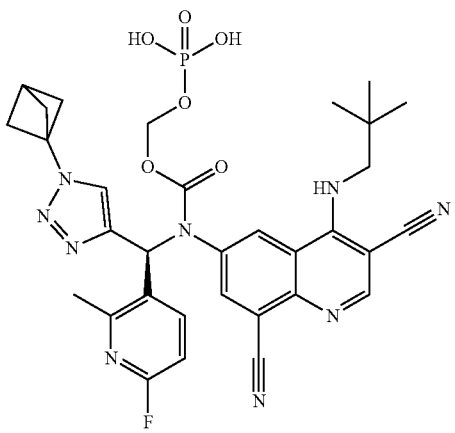 [SMILES: Cc1nc(F)ccc1[C@@H](c1cn(C23CC(C2)C3)nn1)N(C(=O)OCOP(=O)(O)O)c1cc(C#N)c2ncc(C#N)c(NCC(C)(C)C)c2c1]

or a pharmaceutically acceptable salt thereof.

2. A composition comprising the compound according to claim 1 or a pharmaceutically acceptable salt thereof, and a pharmaceutically acceptable carrier.

3. A compound having the formula:
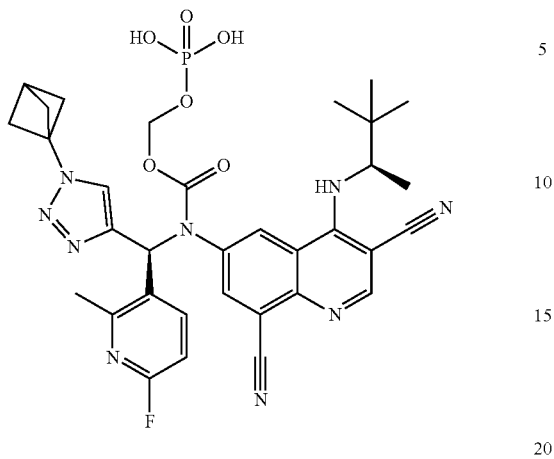
or a pharmaceutically acceptable salt thereof.
4. A composition comprising the compound according to claim 3 or a pharmaceutically acceptable salt thereof, and a pharmaceutically acceptable carrier.
* * * * *